United States Patent
Bleicher et al.

(10) Patent No.: US 11,505,573 B2
(45) Date of Patent: Nov. 22, 2022

(54) PEPTIDE MACROCYCLES AGAINST *ACINETOBACTER BAUMANNII*

(71) Applicant: Hoffmann-La Roche Inc., Little Falls, NJ (US)

(72) Inventors: Konrad Bleicher, Basel (CH); Daniella Cheang, Basel (CH); Patrick Di Giorgio, Basel (CH); Taishan Hu, Basel (CH); Patrizio Mattei, Basel (CH); Petra Schmitz, Basel (CH); Theodor Stoll, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/358,371

(22) Filed: Mar. 19, 2019

(65) Prior Publication Data

US 2019/0300569 A1  Oct. 3, 2019

(30) Foreign Application Priority Data

Mar. 28, 2018 (WO) ................ PCT/CN2018/080820

(51) Int. Cl.
| | |
|---|---|
| *C07K 5/09* | (2006.01) |
| *C07K 5/00* | (2006.01) |
| *C07K 5/08* | (2006.01) |
| *C07K 5/083* | (2006.01) |
| *C07K 5/093* | (2006.01) |
| *A61K 38/00* | (2006.01) |
| *C07K 5/087* | (2006.01) |
| *C07K 5/02* | (2006.01) |
| *C07K 5/097* | (2006.01) |
| *C07K 7/50* | (2006.01) |
| *A61K 38/12* | (2006.01) |

(52) U.S. Cl.
CPC ............. *C07K 5/0815* (2013.01); *C07K 5/00* (2013.01); *C07K 5/08* (2013.01); *C07K 5/081* (2013.01); *C07K 5/0806* (2013.01); *C07K 5/0819* (2013.01); *C07K 5/0827* (2013.01); *A61K 38/00* (2013.01); *A61K 38/12* (2013.01); *C07K 5/02* (2013.01); *C07K 5/0808* (2013.01); *C07K 5/0812* (2013.01); *C07K 5/0821* (2013.01); *C07K 7/50* (2013.01)

(58) Field of Classification Search
CPC .......... A61K 38/00; A61K 38/12; C07K 5/00; C07K 5/02; C07K 5/08; C07K 5/0806; C07K 5/0808; C07K 5/081; C07K 5/0812; C07K 5/0815; C07K 5/0819; C07K 5/0821; C07K 5/0827; C07K 7/50
See application file for complete search history.

(56) References Cited

U.S. PATENT DOCUMENTS

| | | | |
|---|---|---|---|
| 7,521,420 | B2 | 4/2009 | Fraser et al. |
| 11,066,443 | B2 | 7/2021 | Alanine et al. |
| 11,098,080 | B2 | 8/2021 | Alanine et al. |
| 2005/0256037 | A1 | 11/2005 | Lampe et al. |
| 2006/0025566 | A1 | 2/2006 | Hoveyda et al. |
| 2006/0258571 | A1 | 11/2006 | Lampe et al. |
| 2007/0021331 | A1 | 1/2007 | Fraser et al. |
| 2008/0275018 | A1 | 11/2008 | Endermann et al. |
| 2017/0233437 | A1 | 8/2017 | Alanine et al. |
| 2019/0321440 | A1 | 10/2019 | Bleicher et al. |
| 2020/0040031 | A1 | 2/2020 | Alanine et al. |

FOREIGN PATENT DOCUMENTS

| | | |
|---|---|---|
| CL | 200402547 | 9/2005 |
| CN | 103387601 A | 11/2013 |
| EP | 1 498 422 A1 | 1/2005 |
| EP | 3 388 444 A1 | 10/2018 |

(Continued)

OTHER PUBLICATIONS

Hiroki Azuma et al., "A publication of reliable methods for the preparation of organic compounds" Organic Syntheses, pp. 152-161, 2011.

(Continued)

*Primary Examiner* — Julie Ha
*Assistant Examiner* — Erinne R Dabkowski
(74) *Attorney, Agent, or Firm* — Andre T. Krammer

(57) ABSTRACT

The present invention provides compounds of formula (I)

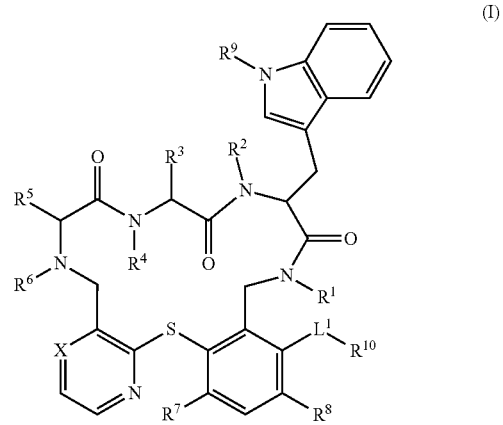

wherein X, $L^1$ and $R^1$ to $R^{10}$ are as described herein, as well as pharmaceutically acceptable salts thereof. Further the present invention is concerned with the manufacture of the compounds of formula (I), pharmaceutical compositions comprising them and their use as medicaments for the treatment of diseases and infections caused by *Acinetobacter baumannii*.

26 Claims, No Drawings

(56) References Cited

FOREIGN PATENT DOCUMENTS

| | | | |
|---|---|---|---|
| WO | 01/14346 | A1 | 3/2001 |
| WO | 03/106480 | A1 | 12/2003 |
| WO | 2004/012816 | A1 | 2/2004 |
| WO | 2004/018478 | A2 | 3/2004 |
| WO | 2004/111077 | A1 | 12/2004 |
| WO | 2005/012331 | A1 | 2/2005 |
| WO | 2005/012332 | A1 | 2/2005 |
| WO | 2005/090388 | A1 | 9/2005 |
| WO | 2005/118613 | A2 | 12/2005 |
| WO | 2005/118613 | A3 | 12/2005 |
| WO | 2006/009645 | A1 | 1/2006 |
| WO | 2006/009645 | A8 | 1/2006 |
| WO | 2006/009674 | A1 | 1/2006 |
| WO | 2006/009674 | A8 | 1/2006 |
| WO | 2006/074964 | A1 | 7/2006 |
| WO | 2006/103015 | A1 | 10/2006 |
| WO | 2007/131966 | A1 | 11/2007 |
| WO | 2008/095999 | A1 | 8/2008 |
| WO | 2009/099677 | A2 | 8/2009 |
| WO | 2010/022249 | A2 | 2/2010 |
| WO | 2010/022249 | A3 | 2/2010 |
| WO | 2011/050270 | A2 | 4/2011 |
| WO | 2011/050270 | A3 | 4/2011 |
| WO | 2011/050276 | A1 | 4/2011 |
| WO | 2011/053821 | A1 | 5/2011 |
| WO | 2012/021874 | A1 | 2/2012 |
| WO | 2013/033645 | A1 | 3/2013 |
| WO | 2013/123266 | A1 | 8/2013 |
| WO | 2014/081886 | A1 | 5/2014 |
| WO | 2014/110420 | A1 | 7/2014 |
| WO | 2016/016291 | A1 | 2/2016 |
| WO | 2018/189065 | A1 | 10/2018 |
| WO | 2019/206853 | A1 | 10/2019 |

OTHER PUBLICATIONS

International Search Report for PCT/EP2016/075499 dated Jan. 5, 2017, 6 pages.
International Search Report for PCT/EP2019/060272 dated Jul. 9, 2019, 4 pages.
Ballatore et al., "Carboxylic Acid (Bio)Isosteres in Drug Design" ChemMedChem 8(3):385-395 ( 2013).
International Search Report and Written Opinion of the Internationa341 Search Authority for PCT/EP2019/057489 (dated May 17, 2019).
Marsault et al., "Efficient parallel synthesis of macrocyclic peptidomimetics" Bioorganic & Medicinal Chemistry Letters 18:4731-4735 ( 2008).
Balraju, V. et al., "Synthesis for cyclic peptides constrained with biarylamine linkers using Buchwald-Hartwig C—N coupling," J. Org. Chem. 71(23): 8954-8956 (2006).
Belikov, V.G., "Pharmaceutical Chemistry," Tutorial, $4^{th}$, revised and expanded edition, Moscow, MEDPress-Inform, 2007, pp. 27-29 (including English Translation).
International Search Report and Written Opinion for PCT/EP2018/058957, dated May 28, 2018, 10 pages.
Webster, A.M. et al., "Synthesis of biaryl-linked cyclic peptoids," Tetrahedron Lett. 58:1010-14(2017).
Written Opinion of the International Searching Authority for PCT/EP2019/060272, dated Jul. 9, 2019, 10 pages.
Written Opinion of the International Searching Authority for PCT/EP2016/075499, dated Jan. 5, 2017, 6 pages.
Notice of Allowances for U.S. Appl. No. 16/006,564, dated Jul. 17, 2019; Feb. 5, 2020; Jun. 16, 2020; and Apr. 16, 2021, 29 pages.
Office action for U.S. Appl. No. 16/006,564, dated Apr. 11, 2019, 8 pages.
Office action for U.S. Appl. No. 16/389,292, dated Aug. 25, 2021, 8 pages.
Office action for U.S. Appl. No. 16/389,292, dated Mar. 28, 2022, 20 pages.

PEPTIDE MACROCYCLES AGAINST ACINETOBACTER BAUMANNII

CROSS-REFERENCE TO RELATED APPLICATIONS

This application claims the right of priority to International Application No. PCT/CN2018/080820, filed on Mar. 28, 2018, the entire contents of which is hereby incorporated by reference herein.

FIELD OF THE INVENTION

The present invention provides compounds which exhibit activity against *Acinetobacter baumannii*, their manufacture, pharmaceutical compositions comprising them and their use as medicaments for the treatment of diseases and infections caused by *Acinetobacter baumannii*.

In particular, the present invention relates to compounds of formula (I)

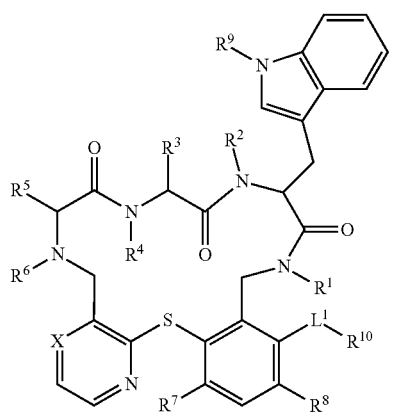

(I)

wherein X, $L^1$ and $R^1$ to $R^{10}$ are as described herein, and pharmaceutically acceptable salts thereof.

BACKGROUND OF THE INVENTION

*Acinetobacter baumannii* is a Gram-negative, aerobic, nonfermenting bacterium recognized over the last decades as an emerging pathogen with very limited treatment options.

*A. baumannii* is considered to be a serious threat by the US Centers for Disease Control and Prevention and belongs to the so called 'ESKAPE' pathogens (*Enterococcus faecium, Staphylococcus aureus, Klebsiella pneumoniae, Acinetobacter baumannii, Pseudomonas aeruginosa* and *Enterobacter* species & *E. coli*) that currently cause the majority of nosocomial infections and effectively "escape" the activity of antimicrobial agents.

*A. baumannii* is most often encountered in intensive care units and surgical wards, where extensive antibiotic use has enabled selection for resistance against all known antimicrobials and where it causes infections that include bacteremia, pneumonia, meningitis, urinary tract infection, and wound infection.

*A. baumannii* has an exceptional ability to upregulate and acquire resistance determinants and shows an environmental persistence that allows its survival and spread in the nosocomial setting, making this organism a frequent cause of outbreaks of infection and an endemic, health care-associated pathogen.

Due to increasing antibiotic resistance to most if not all available therapeutic options, Multi-Drug Resistant (MDR) *A. baumanniii* infections, especially those caused by Carbapenem resistant *A. baumannii*, are extremely difficult or even impossible to treat with high mortality rate as well as increased morbidity and length of stay in intensive care unit.

*Acinetobacter baumannii* has been defined and still remains "a prime example of a mismatch between unmet medical needs and the current antimicrobial research and development pipeline" according to the Antimicrobial Availability Task Force (AATF) of the Infectious Diseases Society of America (IDSA). Thus, there is a high demand and need to identify compounds suitable for the treatment of diseases and infections caused by *Acinetobacter baumannii*.

WO2017/072062 discloses peptide macrocycles that are active against *Acinetobacter baumannii*. However, there is still a high unmet medical need for further, in particular more potent, compounds that are suitable for the treatment of diseases and infections caused by *Acinetobacter baumannii*.

SUMMARY OF THE INVENTION

In a first aspect, the present invention provides compounds of formula (I)

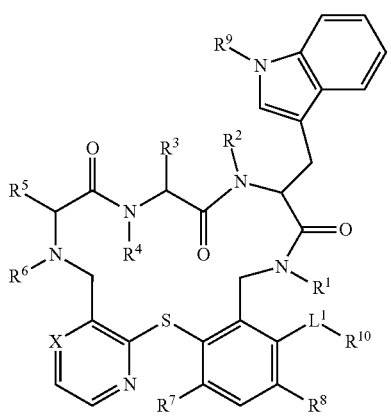

(I)

wherein:
X is $C-L^2-R^{11}$ or N;
$R^1$, $R^2$, $R^4$, $R^6$ and $R^9$ are each individually selected from hydrogen and $C_{1-7}$-alkyl;
$R^3$ and $R^5$ are each independently selected from $C_{1-7}$-alkyl, hydroxy-$C_{1-7}$-alkyl, $-(CH_2)_m-NR^{20}R^{21}$ and $-(CH_2)_n-C(O)-NR^{22}R^{23}$;
$R^7$, $R^8$, $R^{10}$ and $R^{11}$ are each individually selected from hydrogen, halogen, $C_{1-7}$-alkyl, $C_{1-7}$-alkoxy and a carboxylic acid bioisostere, wherein at least one of $R^7$, $R^8$, $R^{10}$ and $R^{11}$ is a carboxylic acid bioisostere;
$R^{20}$, $R^{21}$, $R^{22}$ and $R^{23}$ are each individually selected from hydrogen, $C_{1-7}$-alkyl, $C_{1-7}$-haloalkyl and carboxy-$C_{1-7}$-alkyl;
$L^1$ and $L^2$ are each individually selected from a covalent bond, a group

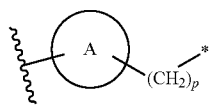

and a group

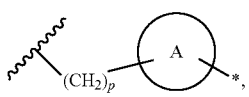

wherein:

A is selected from aryl, heteroaryl, cycloalkyl and heterocycloalkyl;

p is 0, 1, 2, 3, or 4;

the wavy line indicates the point of attachment of $L^1$ to the rest of formula (I) or of $L^2$ to "C" in "C-$L^2$-$R^{11}$"; and

* indicates the point of attachment of $L^1$ to $R^{10}$ or of $L^2$ to $R^{11}$; and m and n are each independently an integer selected from 1, 2, 3, and 4;

or a pharmaceutically acceptable salt thereof.

In a further aspect, the present invention provides a process for the manufacture of the compounds of formula (I) described herein, comprising the steps of:

a) reductive amination of a compound of formula (III), wherein X, $L^1$, $R^1$, $R^7$, $R^8$, $R^{10}$ and PG are as defined herein, with a compound of formula (IV), wherein $R^2$, $R^3$, $R^4$, $R^5$, $R^6$, $R^9$ and resin are as defined herein, to provide a compound of formula (II), wherein X, $L^1$, $R^1$, $R^2$, $R^3$, $R^4$, $R^5$, $R^6$, $R^7$, $R^8$, $R^9$, $R^{10}$, PG and resin are as defined herein;

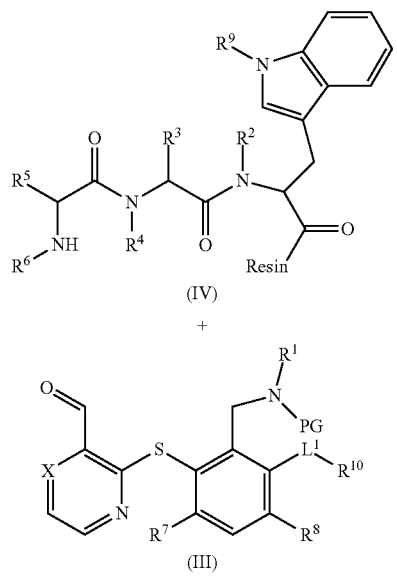

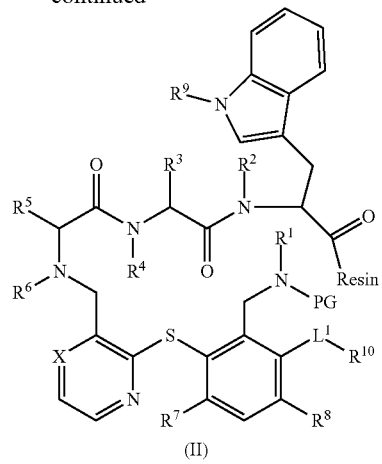

b) removal of the protective group (PG) and the resin from the compound of formula (II) to provide a compound of formula (IIA), wherein X, $L^1$, $R^1$, $R^2$, $R^3$, $R^4$, $R^5$, $R^6$, $R^7$, $R^8$, $R^9$ and $R^{10}$ are as defined herein;

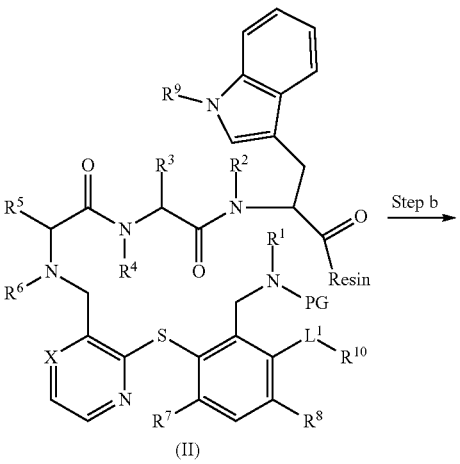

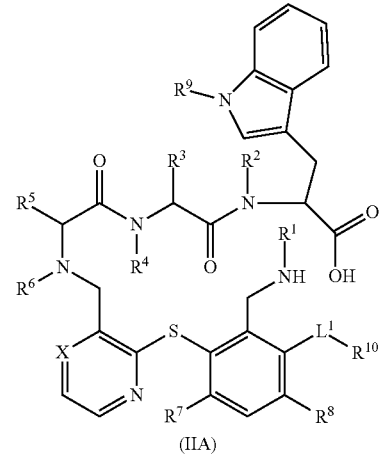

c) cyclisation of the compound of formula (IIA) using a coupling reagent in the presence of a base

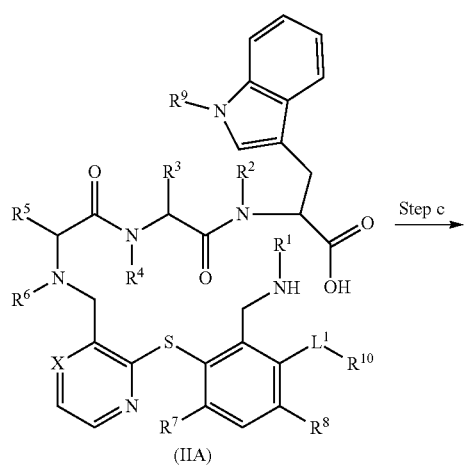

(IIA)

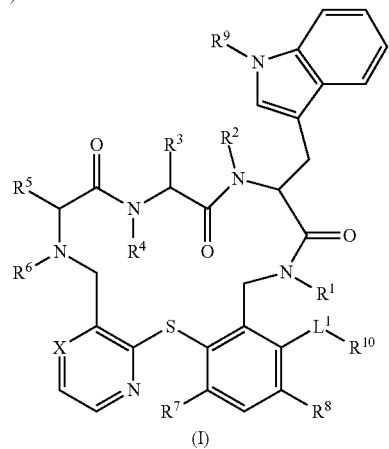

(I)

to afford said compound of formula (I).

In a further aspect, the present invention provides a compound of formula (I) described herein, obtainable by a process described herein.

In a further aspect, the present invention provides a pharmaceutical composition comprising a compound of formula (I) described herein or a pharmaceutically acceptable salt thereof and one or more pharmaceutically acceptable excipients.

In a further aspect, the present invention provides a compound of formula (I) described herein or a pharmaceutically acceptable salt thereof for use as therapeutically active substance.

In a further aspect, the present invention provides a compound of formula (I) described herein or a pharmaceutically acceptable salt thereof or a pharmaceutical composition described herein for use as an antibiotic.

In a further aspect, the present invention provides a compound of formula (I) described herein or a pharmaceutically acceptable salt thereof or a pharmaceutical composition described herein for use in the treatment or prevention of infections and resulting diseases caused by *Acinetobacter baumannii*.

In a further aspect, the present invention provides a method for the treatment or prevention of infections and resulting diseases caused by *Acinetobacter baumannii*, which method comprises administering a compound of formula (I) described herein or a pharmaceutically acceptable salt thereof or a pharmaceutical composition described herein to a human being or an animal.

In a further aspect, the present invention provides the use of a compound of formula (I) described herein or a pharmaceutically acceptable salt thereof or a pharmaceutical composition described herein for the treatment or prevention of infections and resulting diseases caused by *Acinetobacter baumannii*.

In a further aspect, the present invention provides the use of a compound of formula (I) described herein or a pharmaceutically acceptable salt thereof or a pharmaceutical composition described herein for the manufacture of a medicament for the treatment or prevention of infections and resulting diseases caused by *Acinetobacter baumannii*.

DETAILED DESCRIPTION OF THE INVENTION

Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

All publications, patent applications, patents, and other references mentioned herein are incorporated by reference in their entirety.

The nomenclature used in this Application is based on IUPAC systematic nomenclature, unless indicated otherwise.

OpenEye Lexichem version 1.2.0 or Insight for Excel 2017 R2 were employed to generate IUPAC chemical names.

Any open valency appearing on a carbon, oxygen, sulfur or nitrogen atom in the structures herein indicates the presence of a hydrogen atom, unless indicated otherwise.

The term "moiety" refers to an atom or group of chemically bonded atoms that is attached to another atom or molecule by one or more chemical bonds thereby forming part of a molecule. For example, the variables $R^1$, $R^2$ and $R^3$ of formula (I) refer to moieties that are attached to the core structure of formula (I) by a covalent bond.

When indicating the number of substituents, the term "one or more" refers to the range from one substituent to the highest possible number of substitution, i.e. replacement of one hydrogen atom up to replacement of all hydrogen atoms by substituents.

The term "optional" or "optionally" denotes that a subsequently described event or circumstance can but need not occur, and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. If nothing else is indicated, a specified group is understood to be unsubstituted, which means that said specified group bears no substituents. When indicating the number of substituents, the term "one or more" means from one substituent to the highest possible number of substitution, i.e. replacement of one hydrogen atom up to replacement of all hydrogen atoms by substituents.

The term "compound(s) of this invention" and "compound(s) of the present invention" refers to compounds as disclosed herein and stereoisomers, tautomers, solvates, and salts (e.g., pharmaceutically acceptable salts) thereof.
When the compounds of the invention are solids, it is understood by those skilled in the art that these compounds, and their solvates and salts, may exist in different solid forms, particularly different crystal forms, all of which are intended to be within the scope of the present invention and specified formulas.

The term "pharmaceutically acceptable salts" denotes salts which are not biologically or otherwise undesirable. Pharmaceutically acceptable salts include both acid and base addition salts.
The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.
The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511). The prefixes D and L or (+) and (−) are employed to designate the sign of rotation of plane-polarized light by the compound, with (−) or L designating that the compound is levorotatory. A compound prefixed with (+) or D is dextrorotatory.

The term "bioisostere" refers to a surrogate structure that exhibits broadly similar biological properties as an atom, or group of atoms of a biologically active compound. Thus, the term "carboxylic acid bioisostere" refers to a surrogate structure that exhibits broadly similar biological properties as a carboxylic acid moiety of a biologically active compound. Non-limiting examples of carboxylic acid bioisosteres are the carboxylic acid bioisosteres described in C. Ballatore et al., ChemMedChem 2013, 8, 385-395 (DOI: 10.1002/cmdc.201200585) and in P. Lassalas et al., J. Med. Chem. 2016, 59, 3183-3203 (DOI: 10.1021/acs.jmedchem.5b01963). Preferred, yet non-limiting examples of carboxylic acid bioisosteres are 3H-benzotriazol-5-yl, methylsulfonylcarbamoyl, acetylsulfamoyl, 1H-tetrazol-5-yl, 2-oxo-1H-pyrimidin-5-yl, 5-oxo-4H-1,2,4-thiadiazol-3-yl, 5-oxo-4H-1,2,4-oxadiazol-3-yl, HO—S(O)$_2$—, —P(O)(OH)$_2$ and 2-hydroxypyrimidin-5-yl. Particularly preferred, yet non-limiting examples of carboxylic acid bioisosteres are 1H-tetrazol-5-yl and HO—S(O)$_2$—.

The term "halo", "halogen", and "halide" are used interchangeably herein and denote fluoro, chloro, bromo, or iodo. Particular examples of halo are fluoro and chloro.

The term "cyano" refers to a group —CN (nitrile).

The term "carboxy" refers to a group —C(O)OH.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl. Particular examples of alkyl are methyl, ethyl, isopropyl, n-butyl, sec-butyl and tert-butyl, most particularly methyl and ethyl.

The term "alkoxy" denotes a group of the formula —O—R', wherein R' is an alkyl group. Examples of alkoxy moieties include methoxy, ethoxy, isopropoxy, and tert-butoxy. A particular example of alkoxy is methoxy (—OCH$_3$).

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms. Particular examples of haloalkyl is trifluoromethyl.

The term "haloalkoxy" denotes an alkoxy group wherein at least one of the hydrogen atoms of the alkoxy group has been replaced by same or different halogen atoms, particularly fluoro atoms. Examples of haloalkoxyl include monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, or trifluoromethoxy. The term "perhaloalkoxy" denotes an alkoxy group where all hydrogen atoms of the alkoxy group have been replaced by the same or different halogen atoms.

The term "hydroxyalkyl" denotes an alkyl group wherein at least one of the hydrogen atoms of the alkyl group has been replaced by a hydroxy group. Examples of hydroxyalky include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl. Particular cycloalkyl is cyclopropyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-azabicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, dihydropyranyl, oxopyridinyl (in particular 2-oxo-1H-pyridin-4-yl). Particular examples of heterocycloalkyl are pyrrolidinyl, piperidinyl, piperazinyl, morpholinyl, 2-oxa-5-aza-bicyclo[2.2.1]heptyl and dihydropyranyl. Particular examples of saturated heterocycloalkyl are pyrrolidinyl, piperidinyl, piperazinyl, morpholinyl and 2-oxa-5-aza-bicyclo[2.2.1]heptyl. A particular example of a partly unsaturated heterocycloalkyl is 2-oxo-1H-pyridin-4-yl.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "aryl" denotes a monovalent aromatic carbocyclic mono- or bicyclic ring system comprising 6 to 10 carbon ring atoms. Examples of aryl moieties include phenyl and naphthyl, most particularly phenyl. Particular aryl substituted by aryl is biphenyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl. Particular examples of heteroaryl are imidazolyl, pyrazolyl, pyrrolyl, isoxazolyl, pyridinyl, pyrazinyl, pyridazinyl, pyrimidinyl, indolyl and quinolyl. Most particular examples of heteroaryl are pyridinyl and indolyl.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups.

The term "amino-protecting group" denotes groups intended to protect an amino group and includes benzyl, benzyloxycarbonyl (carbobenzyloxy, CBZ), Fmoc (9-Fluorenylmethyloxycarbonyl), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups.

The term "deprotection" or "deprotecting" denotes the process by which a protective group is removed after the selective reaction is completed. Deprotecting reagents include acids, bases or hydrogen, in particular potassium or sodium carbonates, lithium hydroxide in alcoholic solutions, zinc in methanol, acetic acid, trifluoroacetic acid, palladium catalysts, or boron tribromide.

The term "coupling reagent" refers to a reagent that is used in peptide synthesis to facilitate amide bond formations. Coupling reagents for use in peptide synthesis are well-known in the art. Some non-limiting examples of coupling reagents are 2-chloro-1-methylpyridinium iodide (Mukaiyama's reagent), carbodiimides such as dicyclohexylcarbodiimide (DCC), diisopropylcarbodiimide (DIC) and 1-Ethyl-3-(3-dimethylaminopropyl)carbodiimide (EDC) and aminium/uronium and phosphonium salts, such as O-(7-azabenzotriazol-1-yl)-N,N,N',N'-tetramethyluronium-hexafluorophosphate (HATU), 2-(1H-benzotriazol-1-yl)-1,1,3,3-tetramethyluronium hexafluorophosphate (HBTU), 2-(1H-Benzotriazole-1-yl)-1,1,3,3-tetramethylaminium tetrafluoroborate (TBTU), O-(1H-6-Chlorobenzotriazole-1-yl)-1,1,3,3-tetramethyluronium hexafluorophosphate (HCTU), benzotriazol-1-yl-oxytripyrrolidinophosphonium hexafluorophosphate (PyBOP) and (7-Azabenzotriazol-1-yloxy)tripyrrolidinophosphonium hexafluorophosphate (PyAOP). Particular examples of coupling reagents are Mukaiyama's reagent and HATU.

The term "resin" refers to a solid support for peptide synthesis that consists of a polymeric matrix functionalized with reactive "linker" groups (such as amino or hydroxyl groups), onto which peptide chains can be built. Resins for solid phase peptide synthesis are well-known in the art. A non-limiting example of a suitable polymeric matrix is poly(styrene-co-divinylbenzene), also known as polystyrene crosslinked with divinylbenzene, styrene divinylbenzene or styrene-DVB copolymer (100-200 mesh). Non-limiting examples of linker groups are 2-chloro-tritylchloride, amino and hydroxy groups.

The terms "pharmaceutical composition" and "pharmaceutical formulation" (or "formulation") are used interchangeably and denote a mixture or solution comprising a therapeutically effective amount of an active pharmaceutical ingredient together with pharmaceutically acceptable excipients to be administered to a mammal, e.g., a human in need thereof.

The term "active pharmaceutical ingredient" (or "API") denotes the compound or molecule in a pharmaceutical composition that has a particular biological activity.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The term "treating" or "treatment" of a disease state includes inhibiting the disease state, i.e., arresting the development of the disease state or its clinical symptoms, or relieving the disease state, i.e., causing temporary or permanent regression of the disease state or its clinical symptoms.

The term "preventing" or "prevention" of a disease state denotes causing the clinical symptoms of the disease state not to develop in a subject that can be exposed to or predisposed to the disease state, but does not yet experience or display symptoms of the disease state.

The term "amino acid" as used herein denotes an organic molecule possessing an amino moiety located at α-position to a carboxylic group. Examples of amino acids include: arginine, glycine, ornithine, 2,4-diaminobutyric acid, lysine, histidine, glutamic acid, glutamine, aspartic acid, isoleucine, leucine, alanine, phenylalanine, tyrosine, tryptophan, methionine, serine and proline. The amino acid employed is optionally in each case the L-form.

Compounds of the Invention

In a first aspect, the present invention provides compounds of formula (I)

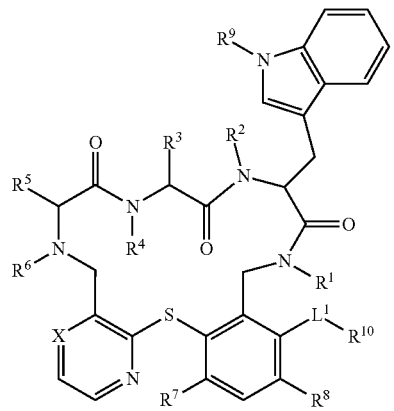

wherein:
X is $C-L^2-R^1$ or N;
$R^1$, $R^2$, $R^4$, $R^6$ and $R^9$ are each individually selected from hydrogen and $C_{1-7}$-alkyl;
$R^3$ and $R^5$ are each independently selected from $C_{1-7}$-alkyl, hydroxy-$C_{1-7}$-alkyl, $-(CH_2)_m-NR^{20}R^{21}$ and $-(CH_2)_n-C(O)-NR^{22}R^{23}$;
$R^7$, $R^8$, $R^{10}$ and $R^{11}$ are each individually selected from hydrogen, halogen, $C_{1-7}$-alkyl, $C_{1-7}$-alkoxy and a carboxylic acid bioisostere, wherein at least one of $R^7$, $R^8$, $R^{10}$ and $R^{11}$ is a carboxylic acid bioisostere;
$R^{20}$, $R^{21}$, $R^{22}$ and $R^{23}$ are each individually selected from hydrogen, $C_{1-7}$-alkyl, $C_{1-7}$-haloalkyl and carboxy-$C_{1-7}$-alkyl;
$L^1$ and $L^2$ are each individually selected from a covalent bond, a group

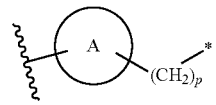

and a group

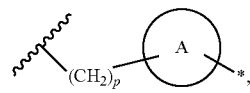

wherein:
A is selected from aryl, heteroaryl, cycloalkyl and heterocycloalkyl;
p is 0, 1, 2, 3, or 4;
the wavy line indicates the point of attachment of $L^1$ to the rest of formula (I) or of $L^2$ to "C" in "$C-L^2-R^{11}$"; and
* indicates the point of attachment of $L^1$ to $R^{10}$ or of $L^2$ to $R^{11}$; and
m and n are each independently an integer selected from 1, 2, 3, and 4;
or a pharmaceutically acceptable salt thereof.

It is to be understood that every embodiment relating to a specific X, $L^1$, $L^2$, A, $R^1$ to $R^{11}$, $R^{20}$ to $R^{23}$, m, n and p as disclosed herein may be combined with any other embodiment relating to another X, $L^1$, $L^2$, A, $R^1$ to $R^{11}$, $R^{20}$ to $R^{23}$, m, n and p as disclosed herein.

In one embodiment, there is provided a compound of formula (I) as described herein, wherein X is C-L$^2$-R$^{11}$ or N, wherein:
L$^2$ is a covalent bond; and
R$^{11}$ is hydrogen.

In a preferred embodiment, there is provided a compound of formula (I) as described herein, wherein X is C-L$^2$-R$^{11}$, wherein:
L$^2$ is a covalent bond; and
R$^{11}$ is hydrogen.

In one embodiment, there is provided a compound of formula (I) as described herein, wherein X is N.

In one embodiment, there is provided a compound of formula (I) as described herein, wherein R$^1$ is hydrogen.

In one embodiment, there is provided a compound of formula (I) as described herein, wherein R$^2$ is C$_{1-7}$-alkyl.

In a preferred embodiment, there is provided a compound of formula (I) as described herein, wherein R$^2$ is methyl.

In one embodiment, there is provided a compound of formula (I) as described herein, wherein R$^3$ is —(CH$_2$)$_m$—NR$^{20}$R$^{21}$, wherein:
R$^{20}$ is selected from hydrogen, C$_{1-7}$-alkyl and C$_{1-7}$-haloalkyl;
R$^{21}$ is hydrogen; and
m is 3 or 4.

In a preferred embodiment, there is provided a compound of formula (I) as described herein, wherein R$^3$ is —(CH$_2$)$_m$—NR$^{20}$R$^{21}$, wherein:
R$^{20}$ and R$^{21}$ are both hydrogen; and
m is 3 or 4 (i.e. R$^3$ is 4-aminobutyl or 3-aminopropyl).

In one embodiment, there is provided a compound of formula (I) as described herein, wherein R$^4$ is hydrogen.

In one embodiment, there is provided a compound of formula (I) as described herein, wherein R$^5$ is selected from C$_{1-7}$-alkyl, hydroxy-C$_{1-7}$-alkyl, —(CH$_2$)$_m$—NR$^{20}$R$^{21}$ and —(CH$_2$)$_n$—C(O)—NR$^{22}$R$^{23}$, wherein:
R$^{20}$ is hydrogen or carboxy-C$_{1-7}$-alkyl;
each of R$^{21}$, R$^{22}$ and R$^{23}$ is hydrogen;
m is 2 or 3; and
n is 2.

In a preferred embodiment, there is provided a compound of formula (I) as described herein, wherein R$^5$ is —(CH$_2$)$_m$—NR$^{20}$R$^{21}$, wherein:
R$^{20}$ and R$^{21}$ are both hydrogen; and
m is 2 or 3 (i.e. R$^5$ is 2-aminoethyl or 3-aminopropyl).

In one embodiment, there is provided a compound of formula (I) as described herein, wherein R$^5$ is —(CH$_2$)$_m$—NR$^{22}$R$^{23}$, wherein m, R$^{22}$ and R$^{23}$ are as described herein.

In one embodiment, there is provided a compound of formula (I) as described herein, wherein R$^6$ is hydrogen.

In one embodiment, there is provided a compound of formula (I) as described herein, wherein R$^7$ is selected from hydrogen, halogen, C$_{1-7}$-alkyl and C$_{1-7}$-alkoxy.

In a preferred embodiment, there is provided a compound of formula (I) as described herein, wherein R$^7$ is selected from hydrogen, chloro, fluoro, methyl and methoxy.

In one embodiment, there is provided a compound of formula (I) as described herein, wherein R$^8$ is selected from hydrogen and a carboxylic acid bioisostere.

In a preferred embodiment, there is provided a compound of formula (I) as described herein, wherein R$^8$ is hydrogen.

In one embodiment, there is provided a compound of formula (I) as described herein, wherein R$^9$ is hydrogen.

In one embodiment, there is provided a compound of formula (I) as described herein, wherein R$^{10}$ is hydrogen or a carboxylic acid bioisostere.

In a preferred embodiment, there is provided a compound of formula (I) as described herein, wherein R$^{10}$ is a carboxylic acid bioisostere.

In a particularly preferred embodiment, there is provided a compound of formula (I) as described herein, wherein R$^{10}$ is a carboxylic acid bioisostere selected from 1H-tetrazol-5-yl and HO—S(O)$_2$—.

In one embodiment, there is provided a compound of formula (I) as described herein, wherein L$^1$ is a covalent bond or a group wherein:
A is aryl or heterocycloalkyl;
p is 0 or 1;
the wavy line indicates the point of attachment of L$^1$ to the rest of formula (I); and
* indicates the point of attachment of L$^1$ to R$^{10}$.

In a preferred embodiment, there is provided a compound of formula (I) as described herein, wherein L$^1$ is a group wherein:
A is aryl;
p is 0;
the wavy line indicates the point of attachment of L$^1$ to the rest of formula (I); and
* indicates the point of attachment of L$^1$ to R$^{10}$.

In a particularly preferred embodiment, there is provided a compound of formula (I) as described herein, wherein L$^1$ is a group wherein the wavy lines indicate the points of attachment.

In a further particularly preferred embodiment, there is provided a compound of formula (I) as described herein, wherein L$^1$ is a group wherein the wavy lines indicate the points of attachment.

In one embodiment, there is provided a compound of formula (I) as described herein, wherein L$^1$ is selected from a covalent bond,

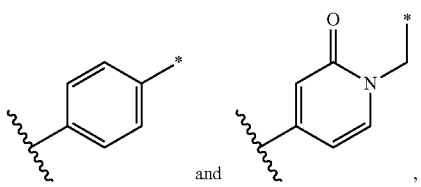 [SMILES: *c1ccc(*)cc1 ; *Cn1ccc(*)cc1=O] and , wherein:
each wavy line indicates the point of attachment of $L^1$ to the rest of formula (I); and
each * indicates the point of attachment of $L^1$ to $R^{10}$.

In one embodiment, there is provided a compound of formula (I) as described herein, wherein:
$L^1$ is a covalent bond or a group

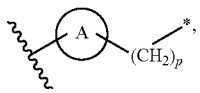

wherein:
A is aryl or heterocycloalkyl;
p is 0 or 1;
the wavy line indicates the point of attachment of $L^1$ to the rest of formula (I); and
* indicates the point of attachment of $L^1$ to $R^{10}$; and
$R^{10}$ is hydrogen or a carboxylic acid bioisostere.

In a preferred embodiment, there is provided a compound of formula (I) as described herein, wherein:
$L^1$ is a group

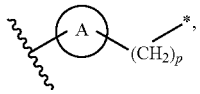

wherein:
A is aryl or heterocycloalkyl;
p is 0 or 1;
the wavy line indicates the point of attachment of $L^1$ to the rest of formula (I); and
* indicates the point of attachment of $L^1$ to $R^{10}$; and
$R^{10}$ is a carboxylic acid bioisostere.

In a particularly preferred embodiment, there is provided a compound of formula (I) as described herein, wherein:
$L^1$ is a group

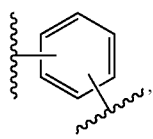

wherein the wavy lines indicate the points of attachment; and
$R^{10}$ is a carboxylic acid bioisostere selected from 1H-tetrazol-5-yl and HO—S(O)$_2$—.

In a further particularly preferred embodiment, there is provided a compound of formula (I) as described herein, wherein:

$L^1$ is a group

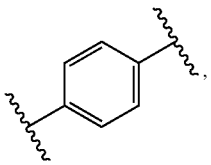 [SMILES: *c1ccc(*)cc1]

wherein the wavy lines indicate the points of attachment; and
$R^{10}$ is a carboxylic acid bioisostere selected from 1H-tetrazol-5-yl or HO—S(O)$_2$—.

In one embodiment, there is provided a compound of formula (I) as described herein, wherein:
X is C-$L^2$-$R^{11}$ or N;
$R^1$ is hydrogen;
$R^2$ is $C_{1-7}$-alkyl;
$R^3$ is —(CH$_2$)$_m$—NR$^{20}$R$^{21}$, wherein:
  $R^{20}$ is selected from hydrogen, $C_{1-7}$-alkyl and $C_{1-7}$-haloalkyl;
  $R^{21}$ is hydrogen; and
  m is 3 or 4;
$R^4$ is hydrogen;
$R^5$ is selected from $C_{1-7}$-alkyl, hydroxy-$C_{1-7}$-alkyl, —(CH$_2$)$_m$—NR$^{20}$R$^{21}$ and —(CH$_2$)$_n$—C(O)—NR$^{22}$R$^{23}$, wherein:
  $R^{20}$ is hydrogen or carboxy-$C_{1-7}$-alkyl;
  each of $R^{21}$, $R^{22}$ and $R^{23}$ is hydrogen;
  m is 2 or 3; and
  n is 2;
$R^6$ is hydrogen;
$R^7$ is selected from hydrogen, halogen, $C_{1-7}$-alkyl and $C_{1-7}$-alkoxy;
$R^8$ is selected from hydrogen and a carboxylic acid bioisostere;
$R^9$ is hydrogen;
$R^{10}$ is hydrogen or a carboxylic acid bioisostere;
$R^{11}$ is hydrogen;
$L^1$ is a covalent bond or a group

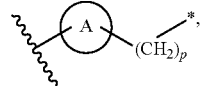

wherein:
A is aryl or heterocycloalkyl;
p is 0 or 1;
the wavy line indicates the point of attachment of $L^1$ to the rest of formula (I); and
*indicates the point of attachment of $L^1$ to $R^{10}$; and
$L^2$ is a covalent bond;
provided that at least one of $R^8$ and $R^{10}$ is a carboxylic acid bioisostere;
or a pharmaceutically acceptable salt thereof.

In a preferred embodiment, there is provided a compound of formula (I) as described herein, wherein:
X is C-$L^2$-$R^{11}$;
$R^1$ is hydrogen;
$R^2$ is $C_{1-7}$-alkyl;
$R^3$ is —(CH$_2$)$_m$—NR$^{20}$R$^{21}$, wherein:
  $R^{20}$ and $R^{21}$ are both hydrogen; and
  m is 3 or 4;
$R^4$ is hydrogen;
$R^5$ is —(CH$_2$)$_m$—NR$^{20}$R$^{21}$, wherein:

$R^{20}$ and $R^{21}$ are both hydrogen; and
m is 2 or 3;
$R^6$ is hydrogen;
$R^7$ is selected from hydrogen, halogen, $C_{1-7}$-alkyl and $C_{1-7}$-alkoxy;
$R^8$ is hydrogen;
$R^9$ is hydrogen;
$R^{10}$ is a carboxylic acid bioisostere;
$R^{11}$ is hydrogen;
$L^1$ is a group

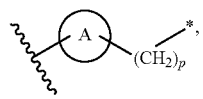

wherein:
A is aryl;
p is 0;
the wavy line indicates the point of attachment of $L^1$ to the rest of formula (I); and
* indicates the point of attachment of $L^1$ to $R^{10}$; and
$L^2$ is a covalent bond;
or a pharmaceutically acceptable salt thereof.

In a particularly preferred embodiment, there is provided a compound of formula (I) as described herein, wherein:
X is $C-L^2-R^{11}$;
$R^1$ is hydrogen;
$R^2$ is methyl;
$R^3$ is $-(CH_2)_m-NR^{20}R^{21}$, wherein:
$R^{20}$ and $R^{21}$ are both hydrogen; and
m is 3 or 4;
$R^4$ is hydrogen;
$R^5$ is $-(CH_2)_m-NR^{20}R^{21}$, wherein:
$R^{20}$ and $R^{21}$ are both hydrogen; and
m is 2 or 3;
$R^6$ is hydrogen;
$R^7$ is selected from hydrogen, chloro, fluoro, methyl and methoxy;
$R^8$ is hydrogen;
$R^9$ is hydrogen;
$R^{10}$ is a carboxylic acid bioisostere selected from 1H-tetrazol-5-yl and $HO-S(O)_2-$;
$R^{11}$ is hydrogen;
$L^1$ is a group

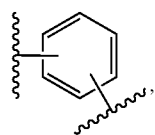

wherein the wavy lines indicate the points of attachment; and
$L^2$ is a covalent bond;
or a pharmaceutically acceptable salt thereof.

In one embodiment, there is provided a compound of formula (I) as described herein, wherein each carboxylic acid bioisostere is selected from the carboxylic acid bioisosteres described in C. Ballatore et al., *ChemMedChem* 2013, 8, 385-395 (DOI: 10.1002/cmdc.201200585) and in P. Lassalas et al., *J. Med. Chem.* 2016, 59, 3183-3203 (DOI: 10.1021/acs.jmedchem. 5b01963).

In a preferred embodiment, there is provided a compound of formula (I) as described herein, wherein each carboxylic acid bioisostere is selected from 3H-benzotriazol-5-yl, methylsulfonylcarbamoyl, acetylsulfamoyl, 1H-tetrazol-5-yl, 2-oxo-1H-pyrimidin-5-yl, 5-oxo-4H-1,2,4-thiadiazol-3-yl, 5-oxo-4H-1,2,4-oxadiazol-3-yl, $HO-S(O)_2-$, $-P(O)(OH)_2$ and 2-hydroxypyrimidin-5-yl.

In a particularly preferred embodiment, there is provided a compound of formula (I) as described herein, wherein each carboxylic acid bioisostere is 1H-tetrazol-5-yl or $HO-S(O)_2-$.

In one embodiment, there is provided a compound of formula (I) as described herein, wherein the compound has a structure of formula (Ia)

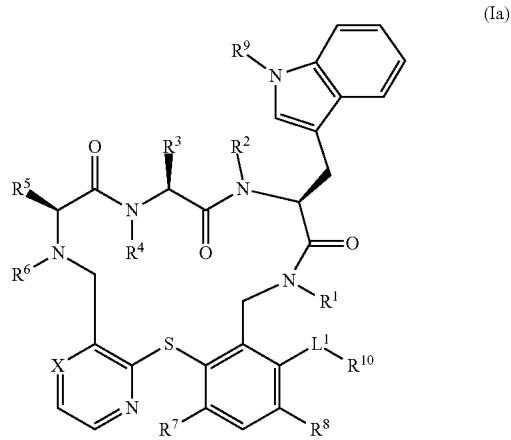

(Ia)

wherein X, $L^1$ and $R^1$ to $R^{10}$ are as described herein;
or a pharmaceutically acceptable salt thereof.

In one embodiment, there is provided a compound of formula (I) as described herein, wherein the compound has a structure of formula (Ib)

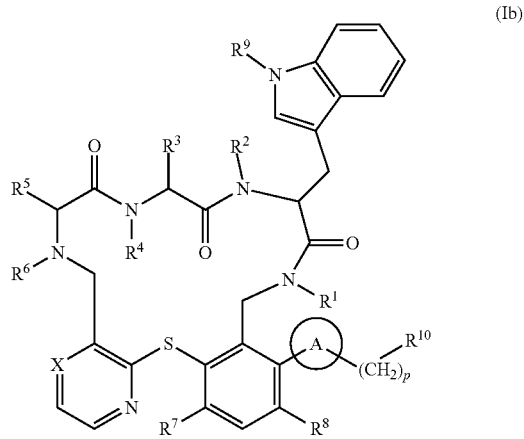

(Ib)

wherein X, A, p and $R^1$ to $R^9$ are as described herein; and
$R^{10}$ is a carboxylic acid bioisostere;
or a pharmaceutically acceptable salt thereof.

In a preferred embodiment, there is provided a compound of formula (I) as described herein, wherein the compound has a structure of formula (Ic)

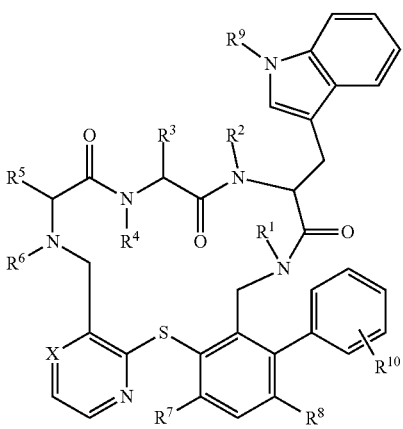

(Ic)

wherein X and $R^1$ to $R^9$ are as described herein; and $R^{10}$ is a carboxylic acid bioisostere;
or a pharmaceutically acceptable salt thereof.

In a further preferred embodiment, there is provided a compound of formula (I) as described herein, wherein the compound has a structure of formula (Id)

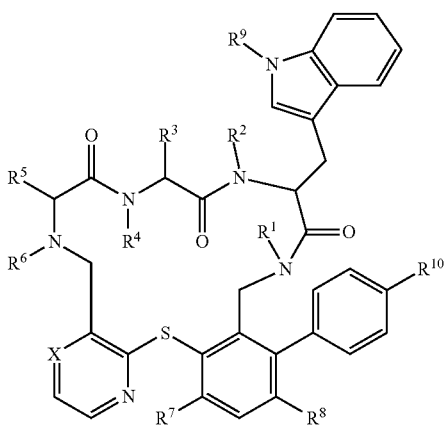

(Id)

wherein X and $R^1$ to $R^9$ are as described herein; and $R^{10}$ is a carboxylic acid bioisostere;
or a pharmaceutically acceptable salt thereof.

In a particularly preferred embodiment, there is provided a compound of formula (I) as described herein, selected from Examples 1 to 23, i.e. selected from:

4-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(25),3,5,7,21,23-hexaen-22-yl]benzenesulfonic acid;

(11S,14S,17S)-14-(4-aminobutyl)-11-(3-aminopropyl)-22-(3H-benzotriazol-5-yl)-25-chloro-17-(1H-indol-3-ylmethyl)-16-methyl-2-thia-4,10,13,16,19-pentazatricyclo[19.4.0.03,8]pentacosa-1(25),3,5,7,21,23-hexaene-12,15,18-trione;

(11S,14S,17S)-14-(4-aminobutyl)-11-(3-aminopropyl)-25-chloro-17-(1H-indol-3-ylmethyl)-16-methyl-22-[4-(1H-tetrazol-5-yl)phenyl]-2-thia-4,10,13,16,19-pentazatricyclo[19.4.0.03,8]pentacosa-1(25),3,5,7,21,23-hexaene-12,15,18-trione;

(11S,14S,17S)-14-(4-aminobutyl)-11-(3-aminopropyl)-25-chloro-17-(1H-indol-3-ylmethyl)-16-methyl-22-[3-(1H-tetrazol-5-yl)phenyl]-2-thia-4,10,13,16,19-pentazatricyclo[19.4.0.03,8]pentacosa-1(25),3,5,7,21,23-hexaene-12,15,18-trione;

N-[4-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]phenyl]sulfonylacetamide;

(11S,14S,17S)-14-(4-aminobutyl)-11-(3-aminopropyl)-25-chloro-17-(1H-indol-3-ylmethyl)-16-methyl-22-(2-oxo-1H-pyrimidin-5-yl)-2-thia-4,10,13,16,19-pentazatricyclo[19.4.0.03,8]pentacosa-1(25),3,5,7,21,23-hexaene-12,15,18-trione;

(11S,14S,17S)-14-(4-aminobutyl)-11-(3-aminopropyl)-25-chloro-17-(1H-indol-3-ylmethyl)-16-methyl-22-[2-oxo-1-(1H-tetrazol-5-ylmethyl)-4-pyridyl]-2-thia-4,10,13,16,19-pentazatricyclo[19.4.0.03,8]pentacosa-1(25),3(8),4,6,21,23-hexaene-12,15,18-trione;

(11S,14S,17S)-14-(4-aminobutyl)-11-(3-aminopropyl)-25-chloro-17-(1H-indol-3-ylmethyl)-16-methyl-22-[4-(5-oxo-4H-1,2,4-thiadiazol-3-yl)phenyl]-2-thia-4,10,13,16,19-pentazatricyclo[19.4.0.03,8]pentacosa-1(25),3(8),4,6,21,23-hexaene-12,15,18-trione;

(11S,14S,17S)-14-(4-aminobutyl)-11-(3-aminopropyl)-25-chloro-17-(1H-indol-3-ylmethyl)-16-methyl-22-[4-(5-oxo-4H-1,2,4-oxadiazol-3-yl)phenyl]-2-thia-4,10,13,16,19-pentazatricyclo[19.4.0.03,8]pentacosa-1(25),3(8),4,6,21,23-hexaene-12,15,18-trione;

(11S,14S,17S)-14-(4-aminobutyl)-11-(3-aminopropyl)-17-(1H-indol-3-ylmethyl)-16-methyl-22-[4-(1H-tetrazol-5-yl)phenyl]-2-thia-4,10,13,16,19-pentazatricyclo[19.4.0.03,8]pentacosa-1(25),3(8),4,6,21,23-hexaene-12,15,18-trione;

4-[(11S,14S,17S)-14-(4-aminobutyl)-11-(3-aminopropyl)-25-chloro-17-(1H-indol-3-ylmethyl)-16-methyl-12,15,18-trioxo-2-thia-4,7,10,13,16,19-hexazatricyclo[19.4.0.03,8]pentacosa-1(25),3(8),4,6,21,23-hexaen-22-yl]benzenesulfonic acid;

4-[(11S,14S,17S)-14-(4-aminobutyl)-11-(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzenesulfonic acid;

(11S,14S,17S)-14-(4-aminobutyl)-11-(3-aminopropyl)-25-fluoro-17-(1H-indol-3-ylmethyl)-16-methyl-22-[4-(1H-tetrazol-5-yl)phenyl]-2-thia-4,10,13,16,19-pentazatricyclo[19.4.0.03,8]pentacosa-1(25),3(8),4,6,21,23-hexaene-12,15,18-trione;

N-[4-[(11S,14S,17S)-14-(4-aminobutyl)-11-(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]phenyl]sulfonylacetamide;

4-[(11S,14S,17S)-14-(4-aminobutyl)-11-(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]-N-methylsulfonyl-benzamide;

4-[(11S,14S,17S)-11,14-bis(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]benzenesulfonic acid;

(11S,14S,17S)-11,14-bis(3-aminopropyl)-25-chloro-17-(1H-indol-3-ylmethyl)-16-methyl-22-[4-(1H-tetrazol-5- yl)phenyl]-2-thia-4,10,13,16,19-pentazatricyclo [19.4.0.03,8]pentacosa-1(21),3,5,7,22,24-hexaene-12,15, 18-trione;

(11S,14S,17S)-11,14-bis(3-aminopropyl)-25-chloro-17-(1H-indol-3-ylmethyl)-16-methyl-22-(2-oxo-1H-pyrimidin-5-yl)-2-thia-4,10,13,16,19-pentazatricyclo[19.4.0.03, 8]pentacosa-1(21),3,5,7,22,24-hexaene-12,15,18-trione;

4-[(11S,14S,17S)-11,14-bis(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1 (25),3(8),4,6,21,23-hexaen-22-yl]benzenesulfonic acid;

(11S,14S,17S)-11,14-bis(3-aminopropyl)-25-fluoro-17-(1H-indol-3-ylmethyl)-16-methyl-22-[4-(1H-tetrazol-5-yl)phenyl]-2-thia-4,10,13,16,19-pentazatricyclo [19.4.0.03,8]pentacosa-1(25),3(8),4,6,21,23-hexaene-12, 15,18-trione;

[4-[(11S,14S,17S)-11,14-bis(3-aminopropyl)-25-fluoro-17-(1H-indol-3-ylmethyl)-6-methyl-12,15,18-trioxo-2-thia-4,10,13,16,19-pentazatricyclo[19.4.0.03,8]pentacosa-1 (25),3(8),4,6,21,23-hexaen-22-yl]phenyl]phosphonic acid;

[4-[(11S,14S,17S)-14-(4-aminobutyl)-11-(3-amino-3-oxopropyl)-25-chloro-17-(1H-indol-3-ylmethyl)-16-methyl-12,15,18-trioxo-2-thia-4,10,13,16,19-pentazatricyclo [19.4.0.03,8]pentacosa-1(21),3,5,7,22,24-hexaen-22-yl] phenyl]phosphonic acid;

[4-[(11S,14S,17S)-14-(4-aminobutyl)-11-(3-aminopropyl)-25-chloro-17-(1H-indol-3-ylmethyl)-16-methyl-12,15, 18-trioxo-2-thia-4,10,13,16,19-pentazatricyclo[19.4.0.03, 8]pentacosa-1(21),3,5,7,22,24-hexaen-22-yl]phenyl] phosphonic acid;

4-[(11S,14S,17S)-14-(4-aminobutyl)-11-(3-aminopropyl)-17-(1H-indol-3-ylmethyl)-16,25-dimethyl-12,15,18-trioxo-2-thia-4,10,13,16,19-pentazatricyclo[19.4.0.03,8] pentacosa-1(25),3 (8),4,6,21,23-hexaen-22-yl] benzenesulfonic acid;

(11S,14S,17S)-14-(4-aminobutyl)-11-(3-aminopropyl)-17-(1H-indol-3-ylmethyl)-16,25-dimethyl-22-[4-(1H-tetrazol-5-yl)phenyl]-2-thia-4,10,13,16,19-pentazatricyclo [19.4.0.03,8]pentacosa-1(25),3(8),4,6,21,23-hexaene-12, 15,18-trione;

4-[(11S,14S,17S)-14-(4-aminobutyl)-11-(2-aminoethyl)-25-chloro-17-(1H-indol-3-ylmethyl)-16-methyl-12,15,18-trioxo-2-thia-4,10,13,16,19-pentazatricyclo[19.4.0.03,8] pentacosa-1(25),3(8),4,6,21,23-hexaen-22-yl] benzenesulfonic acid;

4-[(11S,14S,17S)-11-(2-aminoethyl)-14-(3-aminopropyl)-25-chloro-17-(1H-indol-3-ylmethyl)-16-methyl-12,15, 18-trioxo-2-thia-4,10,13,16,19-pentazatricyclo[19.4.0.03, 8]pentacosa-1(25),3(8),4,6,21,23-hexaen-22-yl] benzenesulfonic acid;

4-[(11S,14S,17S)-14-(3-aminopropyl)-25-chloro-17-(1H-indol-3-ylmethyl)-11,16-dimethyl-12,15,18-trioxo-2-thia-4,10,13,16,19-pentazatricyclo[19.4.0.03,8]pentacosa-1(25),3(8),4,6,21,23-hexaen-22-yl]benzenesulfonic acid;

4-[(11S,14S,17S)-14-(4-aminobutyl)-11-(3-aminopropyl)-17-(1H-indol-3-ylmethyl)-25-methoxy-16-methyl-12,15, 18-trioxo-2-thia-4,10,13,16,19-pentazatricyclo[19.4.0.03, 8]pentacosa-1(25),3(8),4,6,21,23-hexaen-22-yl] benzenesulfonic acid;

(11S,14S,17S)-14-(4-aminobutyl)-11-(3-aminopropyl)-17-(1H-indol-3-ylmethyl)-25-methoxy-16-methyl-22-[4-(1H-tetrazol-5-yl)phenyl]-2-thia-4,10,13,16,19-pentazatricyclo[19.4.0.03,8]pentacosa-1(25),3(8),4,6,21,23-hexaene-12,15,18-trione;

N-[4-[(11S,14S,17S)-14-(4-aminobutyl)-25-chloro-11-(3-hydroxypropyl)-17-(1H-indol-3-ylmethyl)-16-methyl-12, 15,18-trioxo-2-thia-4,10,13,16,19-pentazatricyclo [19.4.0.03,8]pentacosa-1(21),3,5,7,22,24-hexaen-22-yl] phenyl]sulfonylacetamide;

(11S,14S,17S)-14-(4-aminobutyl)-25-chloro-11-(3-hydroxypropyl)-22-(2-hydroxypyrimidin-5-yl)-17-(1H-indol-3-ylmethyl)-16-methyl-2-thia-4,10,13,16,19-pentazatricyclo[19.4.0.03,8]pentacosa-1(21),3,5,7,22,24-hexaene-12,15,18-trione;

N-[4-[(11S,14S,17S)-25-chloro-14-[4-(2,2-difluoroethylamino)butyl]-11-(3-hydroxypropyl)-17-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]phenyl]sulfonylacetamide;

N-[4-[(11S,14S,17S)-25-chloro-1-(3-hydroxypropyl)-17-(1H-indol-3-ylmethyl)-16-methyl-14-[4-(methylamino) butyl]-12,15,18-trioxo-2-thia-4,10,13,16,19-pentazatricyclo[19.4.0.03,8]pentacosa-1(21),3,5,7,22,24-hexaen-22-yl]phenyl]sulfonylacetamide;

(11S,14S,17S)-11-(3-aminopropyl)-25-chloro-14-[4-(2,2-difluoroethylamino)butyl]-22-(2-hydroxypyrimidin-5-yl)-17-(1H-indol-3-ylmethyl)-16-methyl-2-thia-4,10,13, 16,19-pentazatricyclo[19.4.0.03,8]pentacosa-1(21),3,5,7, 22,24-hexaene-12,15,18-trione;

3-[3-[(11S,14S,17S)-22-[4-(acetylsulfamoyl)phenyl]-14-(4-aminobutyl)-25-chloro-7-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-11-yl]propylamino]propanoic acid;

(11S,14S,17S)-14-(4-aminobutyl)-11-(3-aminopropyl)-25-chloro-17-(1H-indol-3-ylmethyl)-16-methyl-23-(1H-tetrazol-5-yl)-2-thia-4,10,13,16,19-pentazatricyclo [19.4.0.03,8]pentacosa-1(21),3,5,7,22,24-hexaene-12,15, 18-trione; and (11S,14S,17S)-14-(4-aminobutyl)-11-(3-aminopropyl)-25-chloro-17-(1H-indol-3-ylmethyl)-16-methyl-23-(1H-triazol-5-yl)-2-thia-4,10,13,16,19-pentazatricyclo [19.4.0.03,8]pentacosa-1(21),3,5,7,22,24-hexaene-12,15, 18-trione;

or a pharmaceutically acceptable salt thereof.

In a further particularly preferred embodiment, there is provided a compound of formula (I) as described herein, selected from Examples 1.02, 5, 7, 8, 11, 12, 13 and 15, i.e. selected from:

(11S,14S,17S)-14-(4-aminobutyl)-11-(3-aminopropyl)-25-chloro-17-(1H-indol-3-ylmethyl)-16-methyl-22-[4-(1H-tetrazol-5-yl)phenyl]-2-thia-4,10,13,16,19-pentazatricyclo[19.4.0.03,8]pentacosa-1(25),3,5,7,21,23-hexaene-12, 15,18-trione (11S,14S,17S)-14-(4-aminobutyl)-11-(3-aminopropyl)-17-(1H-indol-3-ylmethyl)-16-methyl-22-[4-(1H-tetrazol-5-yl)phenyl]-2-thia-4,10,13,16,19-pentazatricyclo [19.4.0.03,8]pentacosa-1(25),3(8),4,6,21,23-hexaene-12, 15,18-trione 4-[(11S,14S,17S)-14-(4-aminobutyl)-11-(3-aminopropyl)-25-fluoro-17-(1H-indol-3-ylmethyl)-16-methyl-12,15, 18-trioxo-2-thia-4,10,13,16,19-pentazatricyclo[19.4.0.03, 8]pentacosa-1(25),3(8),4,6,21,23-hexaen-22-yl] benzenesulfonic acid;

4-[(11S,14S,17S)-11,14-bis(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1 (21),3,5,7,22,24-hexaen-22-yl]benzenesulfonic acid;

4-[(11S,14S,17S)-14-(4-aminobutyl)-11-(3-aminopropyl)-17-(1H-indol-3-ylmethyl)-16,25-dimethyl-12,15,18-trioxo-2-thia-4,10,13,16,19-pentazatricyclo[19.4.0.03,8]
pentacosa-1(25),3(8),4,6,21,23-hexaen-22-yl]
benzenesulfonic acid;
4-[(11S,14S,17S)-14-(4-aminobutyl)-11-(2-aminoethyl)-25-chloro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]
benzenesulfonic acid;
4-[(11S,14S,17S)-11-(2-aminoethyl)-14-(3-aminopropyl)-25-chloro-7-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]
benzenesulfonic acid; and
4-[(11S,14S,17S)-14-(4-aminobutyl)-11-(3-aminopropyl)-17-(1H-indol-3-ylmethyl)-25-methoxy-16-methyl-12,15,18-trioxo-2-thia-4,10,13,16,19-pentazatricyclo[19.4.0.03,8]pentacosa-1(25),3(8),4,6,21,23-hexaen-22-yl]
benzenesulfonic acid;
or a pharmaceutically acceptable salt thereof.

In a particular embodiment, the present invention provides pharmaceutically acceptable salts of the compounds according to formula (I) as described herein, especially hydrochloride salts. In a further particular embodiment, the present invention provides compounds according to formula (I) as described herein.

Manufacturing Processes

Compounds of formula (I), (Ia), (Ib), (Ic) and (Id) and pharmaceutically acceptable salts thereof as defined above can be prepared following standard methods known in the art.

1. General Synthesis of the Tether

The tether intermediate of formula (III) can be prepared following standard methods known in the art, particularly according to methods as described in the examples.

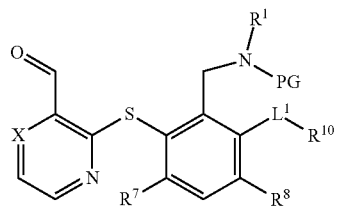
(III)

Alternatively tethers (IIIA) or (IIIB) may be used as intermediates of the macrocycles of formula (I)

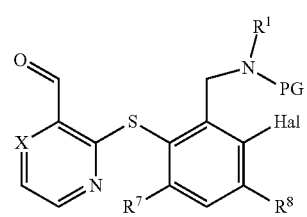
(IIIA)

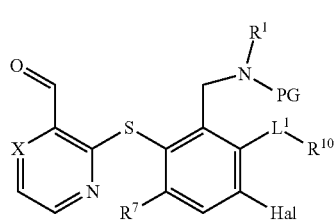
(IIIB)

In compounds (III), (IIIA) and (IIIB), PG is a suitable protective group, such as 9-fluorenylmethoxycarbonyl, and X, $R^1$, $R^7$, $R^8$ and $R^{10}$ are as defined herein. In compounds (IIIA) and (IIIB), Hal is a halogen, preferably Br or I.

2. General Synthesis of the Tripeptide

The tripeptide of formula (IV), wherein $R^2$, $R^3$, $R^4$, $R^5$ and $R^6$ are as defined herein, can be prepared following standard methods known in the art.

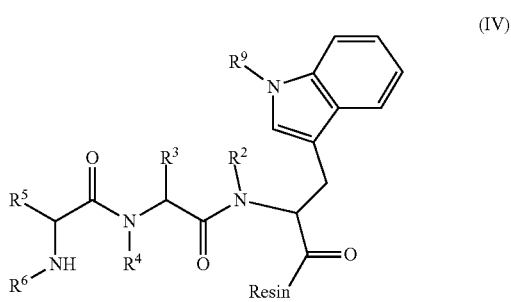
(IV)

The tripeptide sequence (IV) can for example be synthesized via state-of-the-art solid-phase peptide synthesis protocols as follows:

a) A resin (e.g. 2-chloro-trityl resin) as solid support is loaded with the first N-protected amino acid and diisopropylethylamine (N,N-diisopropylethylamine or N,N-diisopropylethylamine) followed by cleavage of the protecting group.

b) A second N-protected amino acid is coupled with a coupling reagent and diisopropylethylamine followed by cleavage of the protecting group (e.g. 9-fluorenylmethoxycarbonyl).

c) A third N-protected amino acid is coupled with a coupling reagent and diisopropylethylamine followed by cleavage of the protecting group.

In a particular embodiment, the N-protected amino acids are protected with 9-fluorenylmethyloxycarbonyl.

In a particular embodiment, the resin is loaded in step a) with 0.1-1.0 equivalents of the first amino acid and excess diisopropylethylamine in dichloromethane.

In a particular embodiment, the resin is thoroughly washed after the coupling reaction in step a) with dimethylformamide (N,N-dimethylformamide) and dichloromethane (dichloromethane).

In a particular embodiment, the 9-fluorenylmethoxycarbonyl protecting group is cleaved off in step a) with a mixture of 50% piperidine in dichloromethane/N,N-dimethylformamide (1:1).

In a particular embodiment, the resin is thoroughly washed after the deprotection in step a) with N,N-dimethylformamide, dichloromethane and methanol followed by drying under vacuum and weighing.

In a particular embodiment, the coupling reagent in step b) is 2-chloro-1-methylpyridinium iodide.

In a particular embodiment, the second amino acid in step b) is coupled with 4 equivalents of 2-chloro-1-methylpyridinium iodide as coupling reagent and 6 equivalents of diisopropylethylamine in N,N-dimethylformamide/dichloromethane (1:1).

In a particular embodiment, the resin is thoroughly washed after the coupling reaction in step b) with dimethylformamide (N,N-dimethylformamide) and dichloromethane (dichloromethane).

In a particular embodiment, the 9-fluorenylmethoxycarbonyl protecting group is cleaved off in step b) with a mixture of 50% piperidine in dichloromethane/N,N-dimethylformamide (1:1).

In a particular embodiment, the resin is thoroughly washed after the deprotection in step b) with N,N-dimethylformamide and dichloromethane followed by drying under vacuum and weighing.

In a particular embodiment, the coupling reagent in step c) is O-(7-azabenzotriazol-1-yl)-N,N,N',N'-tetramethyluronium-hexafluorophosphate.

In a particular embodiment, the third amino acid in step c) is coupled with 4 equivalents of O-(7-azabenzotriazol-1-yl)-N,N,N',N'-tetramethyluronium-hexafluorophosphate as coupling reagent and 6 equivalents of diisopropylethylamine in N,N-dimethylformamide/dichloromethane (1:1).

In a particular embodiment, the resin is thoroughly washed after the coupling reaction in step c) with N,N-dimethylformamide (DMF) and dichloromethane (DCM).

In a particular embodiment, the 9-fluorenylmethoxycarbonyl protecting group is cleaved off in step c) with a mixture of 20% piperidine in N,N-dimethylformamide.

In a particular embodiment, the resin is thoroughly washed after the deprotection in step c) with N,N-dimethylformamide and dichloromethane followed by drying under vacuum and weighing.

3. General Synthesis for the Coupling of the Tripeptide to the Tether

The compound of formula (I) can be obtained, for example starting from the compounds of formula (III) and of formula (IV) according to Scheme 1.

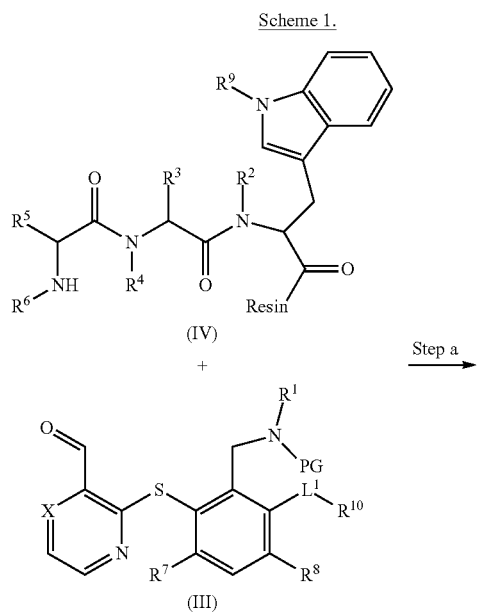

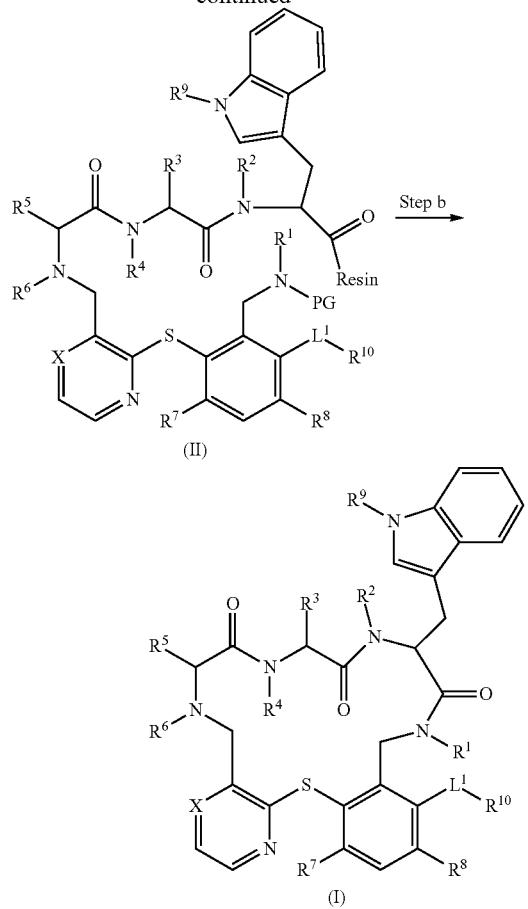

Coupling of the tether aldehyde or ketone of formula (III) with the tripeptide of formula (IV) (Scheme 1, step a) may be achieved, for example, by dissolving said tether aldehyde or ketone of formula (III) in a mixture of 1-methyl-2-pyrrolidone, trimethyl orthoformate (trimethyl orthoformate) and acetic acid and adding the resin comprising the tripeptide of formula (IV) to the solution. After agitation of the mixture, a reducing agent such as sodium cyanoborohydride may be added to provide a compound of formula (II).

In Scheme 1, step b, the protecting group (PG) of the tether is cleaved off, e.g. with a mixture of 20% piperidine in N,N-dimethylformamide. The resin on the tripeptide can be cleaved e.g. by addition of 20% hexafluoroisopropanol in dichloromethane and filtered off. The compound of formula (I) is finally obtained through cyclisation of the cleaved compound of formula (II) using e.g. 0-(7-azabenzotriazol-1-yl)-N,N,N',N'-tetramethyluronium-hexafluorophosphate and diisopropylethylamine, followed by global deprotection of remaining protected functional groups.

Accordingly, in one aspect, the present invention provides a process for the manufacture of the compounds of formula (I) described herein, comprising the steps of:
 a) reductive amination of a compound of formula (III), wherein X, $L^1$, $R^1$, $R^7$, $R^8$, $R^{10}$ and PG are as defined herein, with a compound of formula (IV), wherein $R^2$, $R^3$, $R^4$, $R^5$, $R^6$, $R^9$ and resin are as defined herein, to provide a compound of formula (II), wherein X, $L_1$, $R^1$, $R^2$, $R^3$, $R^4$, $R^5$, $R^6$, $R^7$, $R^8$, $R^9$, $R^{10}$, PG and resin are as defined herein;

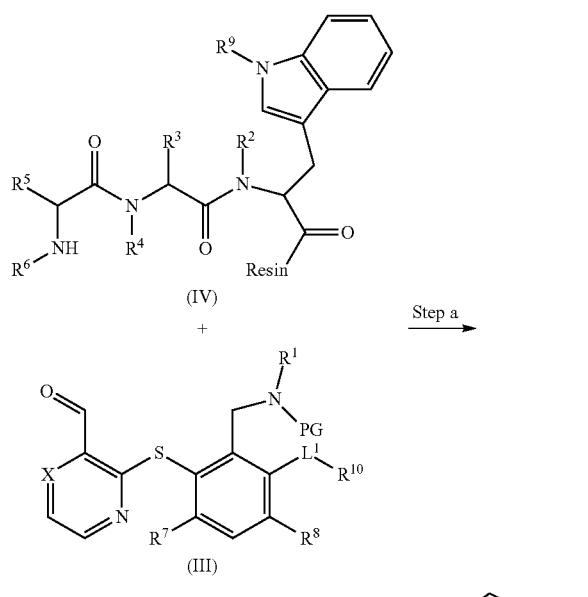

(IV)

+

(III)

Step a →

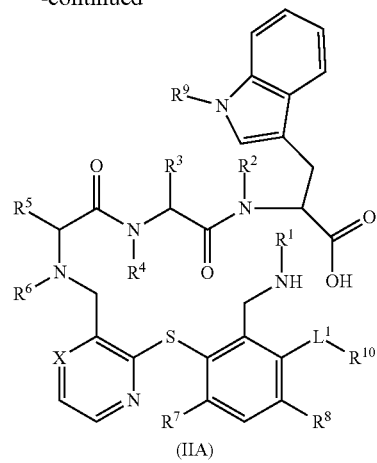

(IIA)

c) cyclisation of the compound of formula (IIA) using a coupling reagent in the presence of a base

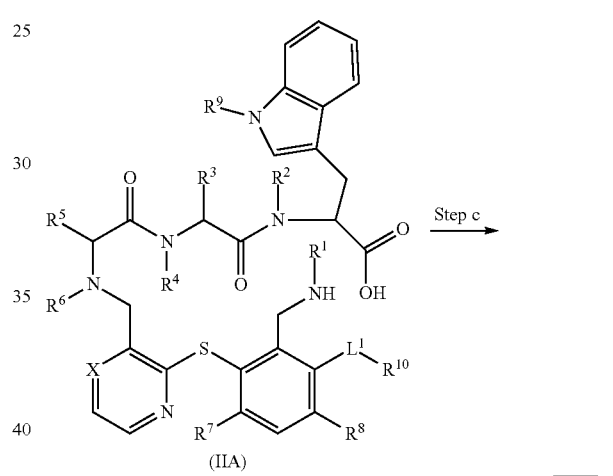

(II)

(IIA)

Step c → b) removal of the protective group (PG) and the resin from the compound of formula (II) to provide a compound of formula (IIA), wherein X, $L^1$, $R^1$, $R^2$, $R^3$, $R^4$, $R^5$, $R^6$, $R^7$, $R^8$, $R^9$ and $R^{19}$ are as defined herein;

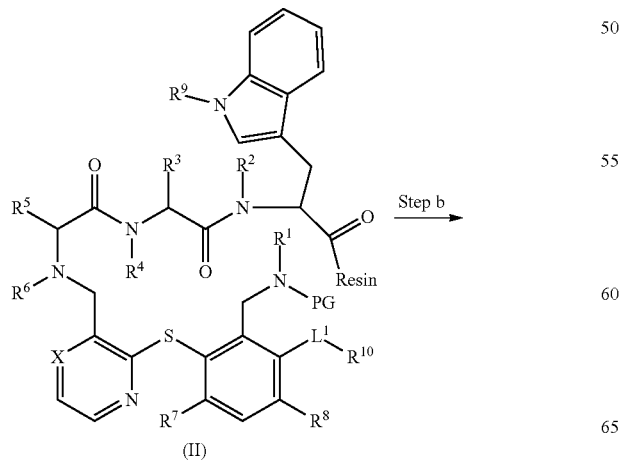

(II)

Step b →

(I)

to afford said compound of formula (I).

Cleavage of protective groups is accomplished using methods and reagents known in the art (exemplary protective groups and their application in organic synthesis are described, for example, in "Greene's Protective Groups in Organic Chemistry" by P. G. M. Wuts, 5th Ed., 2014, John Wiley & Sons, N.Y.).

In a particular embodiment, primary or secondary amines are produced from the tert-butylcarbamate derivates by reaction with a suitable acid, e.g., trifluoroacetic acid or hydrogen chloride, in solvents such as dichloromethane, water, 1,4-dioxane, 2-propanol, acetonitrile or mixtures thereof, optionally in the presence of a carbocation scavenger, e.g., triisopropylsilane or triethylsilane. Under these conditions, N-(tert-butoxycarbonyl)indoles, N-(trimethylphenyl)-amides, N-(trimethyltetrazoles), and O-tert-butyl-dimethylsilylethers are concomitantly converted to free indoles, amides, tetrazoles and alcohols, respectively.

In a particular embodiment, carboxylic acids are produced from their alkyl ester derivatives by saponification using a base such as lithium hydroxide, sodium hydroxide, or potassium hydroxide, in a solvent system such as water/ethanol or water/tetrahydrofuran.

In a particular embodiment, phosphonic acids are produced from their dialkyl ester derivatives by reaction with bromotrimethylsilane in dichloromethane.

In a particular embodiment, a compound of general structure (IIIA) is used as the tether for the macrocyclisation, as illustrated in Scheme 2. In analogy to the sequence shown in Scheme 1, reductive amination (step a) produces intermediate (IIB), which undergoes cleavage of the resin, deprotection and macrocyclisation (step b) to produce halo-macrocycle (VA).

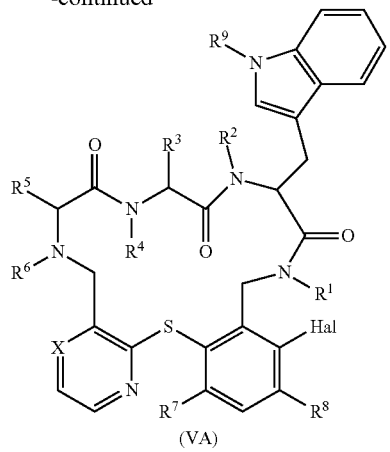

(VA)

Alternatively, a compound of general structure (IIIB) is used as the tether for the macrocyclisation, as illustrated in Scheme 3. In analogy to the sequence shown in Scheme 1, reductive amination, followed by cleavage of the resin (step a) produces intermediate (IIC), which undergoes deprotection and macrocyclisation (step b) to produce halo-macrocycle (VB).

Scheme 2

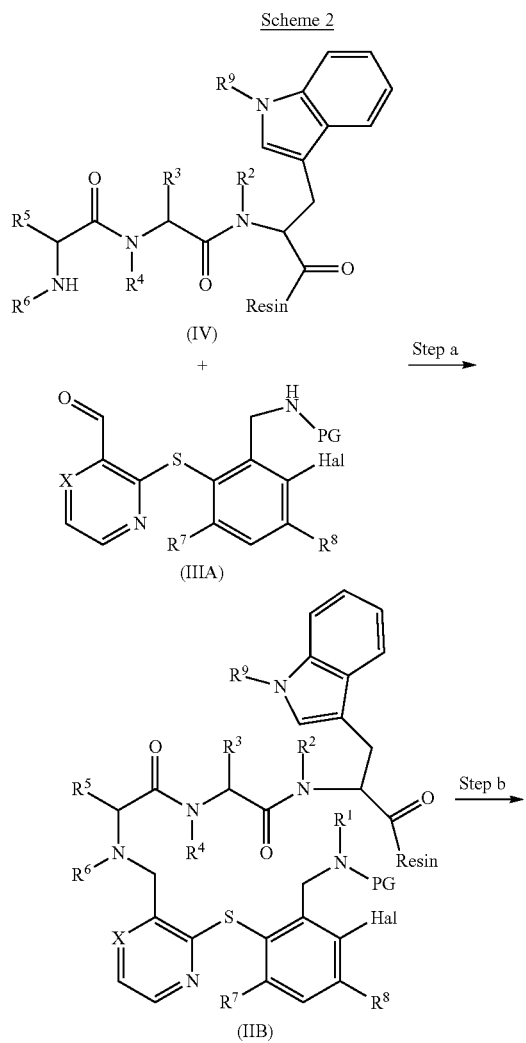

Scheme 3

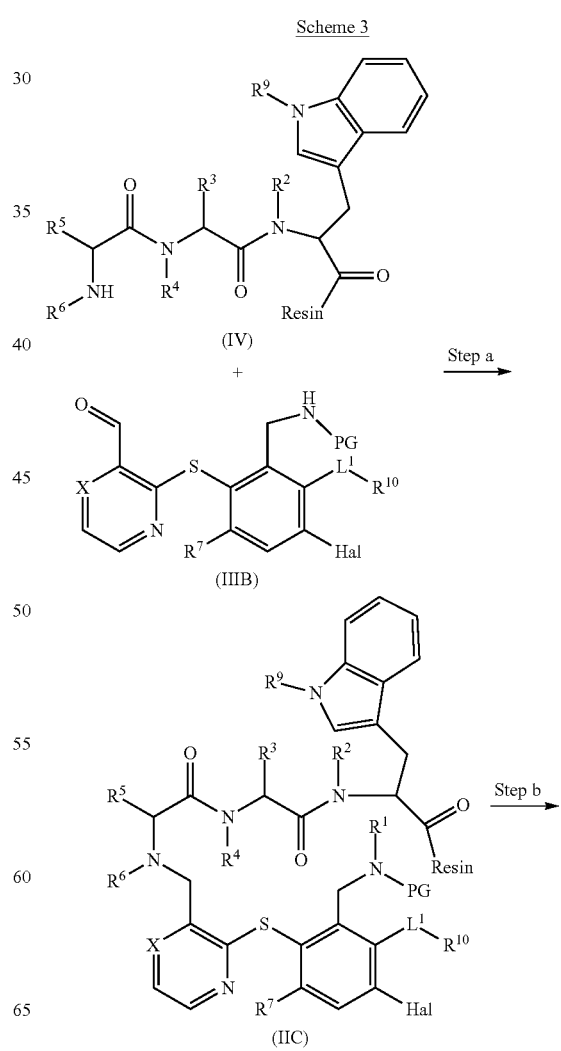

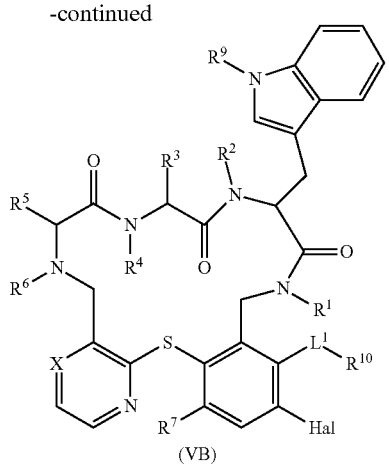

(VB)

Compounds of general formula (I) can also be produced from halo-macrocycles (VA) or (VB) using methods and reagents known in the art. In particular, the Suzuki cross-coupling reaction can be performed to achieve this transformation.

For instance, halo-macrocycle (VA) is reacted with boronic acid (VIAA) or dioxoborolane (VIAB) to produce compounds of formula (I).

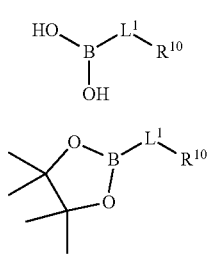

(VIAA)

(VIAB)

The reaction is performed in the presence of a suitable palladium catalyst, e.g., Pd(PPh$_3$)$_4$ or PdCl$_2$(PPh$_3$)$_2$, in a solvent such as water, 1,4-dioxane, N,N-dimethylacetamide, tetrahydrofuran, 2-methyltetrahydrofuran or mixtures thereof, in the presence of a base, e.g., sodium carbonate or potassium phosphate, at temperatures between 20° C. and 150° C., optionally under microwave irradiation.

Similarly, halo-macrocycle (VB) is reacted with boronic acid (VIBA) or dioxoborolane (VIBB) to produce compounds of formula (I).

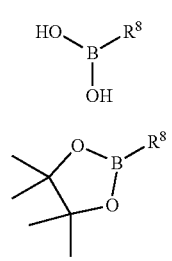

(VIBA)

(VIBB)

The reaction is performed in the presence of a suitable palladium catalyst, e.g., Pd(PPh$_3$)$_4$ or PdCl$_2$(PPh$_3$)$_2$, in a solvent such as water, 1,4-dioxane, N,N-dimethylacetamide, tetrahydrofuran, 2-methyltetrahydrofuran or mixtures thereof, in the presence of a base, e.g., sodium carbonate or potassium phosphate, at temperatures between 20° C. and 150° C., optionally under microwave irradiation.

In a particular embodiment, halomacrocycles (VA) or (VB) can undergo a Suzuki cross-coupling reaction with boronic acid NC—B(OH)$_2$ or NC-L$^1$-B(OH)$_2$ as described above, affording the nitriles (VITA) and (VIIB), respectively.

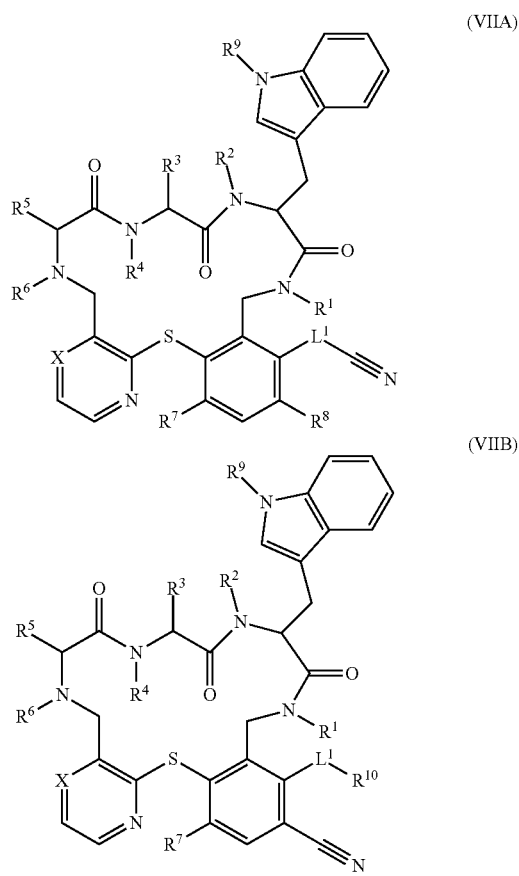

(VIIA)

(VIIB)

Subsequent reaction of nitrile (VITA) with sodium azide in the presence of a suitable catalyst (e.g., zinc bromide, phosphorus oxychloride in a solvent such as 1-methyl-2-pyrrolidone or N,N-dimethlyformamide) at temperatures between 20° C. and 200° C. produces a compound of formula (I), in which R$^{10}$ is 1H-tetrazol-5-yl. Similarly, reaction of nitrile (VIIB) with sodium azide produces a compound of formula (I), in which R$^8$ is 1H-tetrazol-5-yl.

In a particular embodiment, nitrile (VITA) is reacted with hydroxylamine, followed by treatment with 1,1'-thiocarbonyldiimidazole, followed by reaction with boron trifluoride diethyl etherate as described in the experimental section to produce compounds of formula (I), wherein R$^{10}$ is 5-oxo-4,5-dihydro-1,2,4-thiadiazol-3-yl. Similarly, nitrile (VIIB) can be converted into compounds of formula (I), wherein R$^8$ is 5-oxo-4,5-dihydro-1,2,4-thiadiazol-3-yl.

In a particular embodiment, reaction of nitrile (VITA) with hydroxylamine, followed by treatment with isobutyl chloroformate in the presence of pyridine as described in the experimental section produces compounds of formula (I), wherein R$^{10}$ is 5-oxo-4,5-dihydro-1,2,4-oxadiazol-3-yl.

Similarly, nitrile (VIIB) can be converted into compounds of formula (I), wherein $R^8$ is 5-oxo-4,5-dihydro-1,2,4-oxadiazol-3-yl.

Pharmaceutical Compositions

Another aspect of the invention provides pharmaceutical compositions or medicaments comprising the compounds of the invention and a therapeutically inert carrier, diluent or pharmaceutically acceptable excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a compound of the present invention and a carrier or excipient. Suitable carriers and excipients are well known to those skilled in the art and are described in detail in, e.g., Ansel H. C. et al., *Ansel's Pharmaceutical Dosage Forms and Drug Delivery Systems* (2004) Lippincott, Williams & Wilkins, Philadelphia; Gennaro A. R. et al., *Remington: The Science and Practice of Pharmacy* (2000) Lippincott, Williams & Wilkins, Philadelphia; and Rowe R. C, *Handbook of Pharmaceutical Excipients* (2005) Pharmaceutical Press, Chicago. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which compounds of the invention can be administered can vary within wide limits and will, of course, be fitted to the individual requirements in each particular case. In general, in the case of oral administration a daily dosage of about 0.01 to 1000 mg per person of a compound of general formula (I) should be appropriate, although the above upper limit can also be exceeded when necessary.

An example of a suitable oral dosage form is a tablet comprising about 100 mg to 500 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution may be filtered, e.g., using a 0.2 µm filter, to remove impurities and contaminants.

Uses

The compounds of formula (I), (Ia), (Ib), (Ic) and (Id) and their pharmaceutically acceptable salts possess valuable pharmacological properties for the treatment or prevention of infections and resulting diseases, particularly bacteremia, pneumonia, meningitis, urinary tract infection, and wound infection, caused by pathogens, particularly by bacteria, more particularly by *Acinetobacter* species, most particularly by *Acinetobacter baumannii*.

The compounds of formula (I), (Ia), (Ib), (Ic) and (Id) and their pharmaceutically acceptable salts exhibit activity as antibiotics, particularly as antibiotics against *Acinetobacter* species, more particularly as antibiotics against *Acinetobacter baumannii*, most particularly as pathogen-specific antibiotics against *Acinetobacter baumannii*.

The compounds of formula (I), (Ia), (Ib), (Ic) and (Id) and their pharmaceutically acceptable salts can be used as antibiotics, i.e. as antibacterial pharmaceutical ingredients suitable in the treatment and prevention of bacterial infections, particularly in the treatment and prevention of bacterial infections caused by *Acinetobacter* species, more particularly in the treatment and prevention of bacterial infections caused by *Acinetobacter baumannii*.

The compounds of the present invention can be used, either alone or in combination with other drugs, for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

One aspect of the present invention relates to pharmaceutical compositions comprising compounds of formula (I), (Ia), (Ib), (Ic) and (Id) as defined above or their pharmaceutically acceptable salts as defined above and one or more pharmaceutically acceptable excipients.

A further aspect of the present invention relates to pharmaceutical compositions comprising compounds of formula (I), (Ia), (Ib), (Ic) and (Id) or their pharmaceutically acceptable salts as defined above and one or more pharmaceutically acceptable excipients for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

A further aspect of the present invention relates to compounds of formula (I), (Ia), (Ib), (Ic) and (Id) or their pharmaceutically acceptable salts as defined above for use as therapeutically active substances, especially for use as therapeutically active substances for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

A further aspect of the present invention relates to compounds of formula (I), (Ia), (Ib), (Ic) and (Id) or their pharmaceutically acceptable salts as defined above for the use in the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

A further aspect of the present invention relates to a method for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*, which method comprises administering compounds of formula (I), (Ia), (Ib), (Ic) and (Id) or their pharmaceutically acceptable salts as defined above to a subject.

A further aspect of the present invention relates to the use of compounds of formula (I), (Ia), (Ib), (Ic) and (Id) or their pharmaceutically acceptable salts as defined above for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

A further aspect of the present invention relates to the use of compounds of formula (I), (Ia), (Ib), (Ic) and (Id) or their pharmaceutically acceptable salts as defined above for the preparation of medicaments for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*. Such medicaments comprise compounds of formula (I), (Ia), (Ib), (Ic) and (Id) or their pharmaceutically acceptable salts as defined above.

EXAMPLES

The invention will be more fully understood by reference to the following examples. They should however not be construed as limiting the scope of the invention.

All examples and intermediates were prepared under nitrogen atmosphere if not specified otherwise.

Abbreviations Used aq.=aqueous; CAS-RN=Chemical Abstracts Service Registry Number; HPLC=high performance liquid chromatography; MS=mass spectrum; sat.=saturated.

Example 1

4-[(11S,14S,17S)-14-(4-Aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(25),3,5,7,21,23-hexaen-22-yl]benzenesulfonic acid

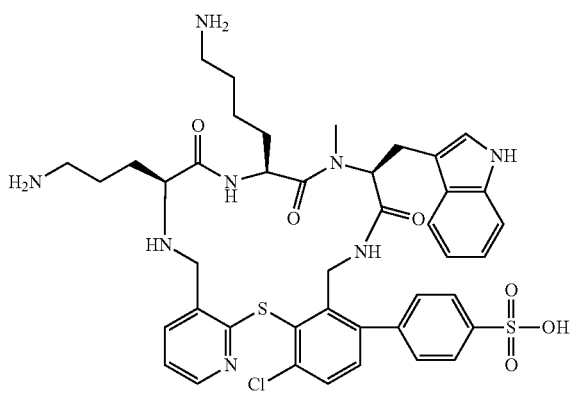

Step 1: 4-((7S,10S,13S)-13-((1-(tert-Butoxycarbonyl)-1H-indol-3-yl)methyl)-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-17-yl)benzenesulfonic acid A mixture of tert-butyl 3-(((7S,10S,13S)-17-bromo-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate (CAS-RN 2097294-18-1; 132 mg, 110 µmol, Eq: 1), 4-boronobenzenesulfonic acid (CAS-RN 913836-00-7; 33.9 mg, 164 µmol, Eq: 1.5) and potassium phosphate (58.1 mg, 274 µmol, Eq: 2.5) in 1,4-dioxane/water 6:1 (4 mL) was sparged with argon for 4 min in an ultrasound bath, then after addition of tetrakis(triphenylphosphine)palladium(0) (38 mg, 32.9 µmol) the mixture was heated at 130° C. for 10 min in a sealed vessel under microwave irradiation. The reaction was partitioned between ethyl acetate and water, the organic layer was washed with brine, dried over magnesium sulfate, filtered and evaporated. The material was purified by preparative reversed phase HPLC (column: Phenomenex Gemini-NX 5u 110A, 100×30 mm) using a gradient of from water (+0.05% trifluoroacetic acid) to acetonitrile as eluent. After lyophilisation a mixture of the title compound and the product with one t-butoxycarbonyl group less was obtained (115 mg, light yellow lyophilised powder). The material was directly used in the next step.

Step 2: 4-((7S,10S,13S)-13-((1H-Indol-3-yl)methyl)-10-(4-aminobutyl)-7-(3-aminopropyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-17-yl)benzenesulfonic acid To the product mixture obtained above (115 mg) in dichloromethane (4 mL) was added trifluoroacetic acid (1.69 g). The clear yellow solution was stirred at room temperature for 2.5 h. The reaction was concentrated under vacuum at 30° C. The residue was dissolved in acetonitrile/water 1:9 and stirred overnight. The material was purified by preparative reversed phase HPLC (column: Phenomenex Gemini-NX 5u 110A, 100×30 mm) using a gradient between water containing (+0.05% trifluoroacetic acid)/acetonitrile as eluent, followed by lyophilisation to produce the title compound as trifluoroacetate salt (72 mg, 58%). White lyophilised powder, MS: 861.3 [M+H]$^+$.

The following examples were produced in analogy to example 1, replacing 4-boronobenzenesulfonic acid by the appropriate organoboron reagent.

| Ex. | Systematic Name | Organoboron reagent | MS |
|---|---|---|---|
| 1.01 | 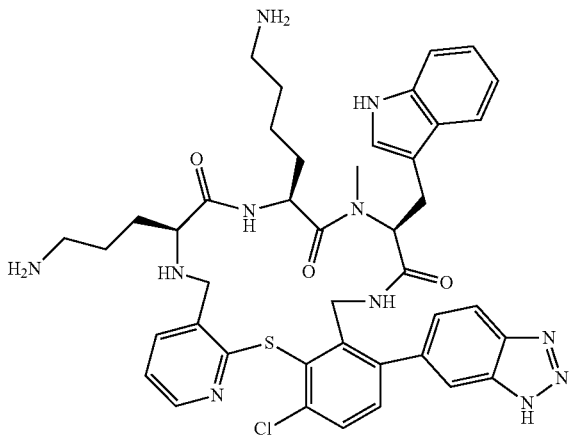<br>(11S,14S,17S)-14-(4-Aminobutyl)-11-(3-aminopropyl)-22-(3H-benzotriazol-5-yl)-25-chloro-17-(1H-indol-3-ylmethyl)-16-methyl-2-thia-4,10,13,16,19-pentazatricyclo[19.4.0.0$^{3,8}$]pentacosa-1(25),3,5,7,21,23-hexaene-12,15,18-trione | 1H-benzotriazol-5-ylboronic acid [CAS-RN 183282-45-3] | 822.6 [M + H]$^+$ |
| 1.02 | 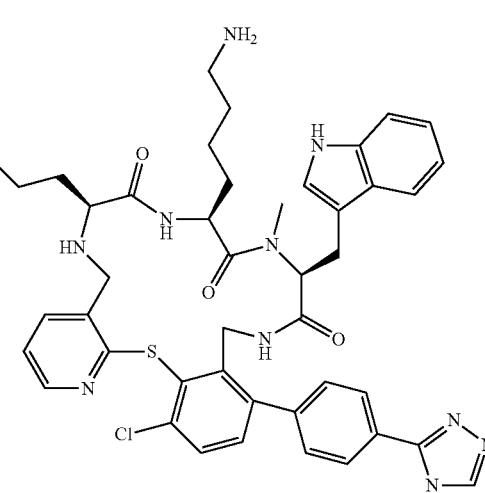<br>(11S,14S,17S)-14-(4-Aminobutyl)-11-(3-aminopropyl)-25-chloro-17-(1H-indol-3-ylmethyl)-16-methyl-22-[4-(1H-tetrazol-5-yl)phenyl]-2-thia-4,10,13,16,19-pentazatricyclo[19.4.0.0$^{3,8}$]pentacosa-1(25),3,5,7,21,23-hexaene-12,15,18-trione | (4-(1H-tetrazol-5-yl)phenyl)boronic acid [CAS-RN 179942-55-3] | 849.3 [M + H]$^+$ |

-continued

| Ex. | Systematic Name | Organoboron reagent | MS |
|---|---|---|---|
| 1.03 | 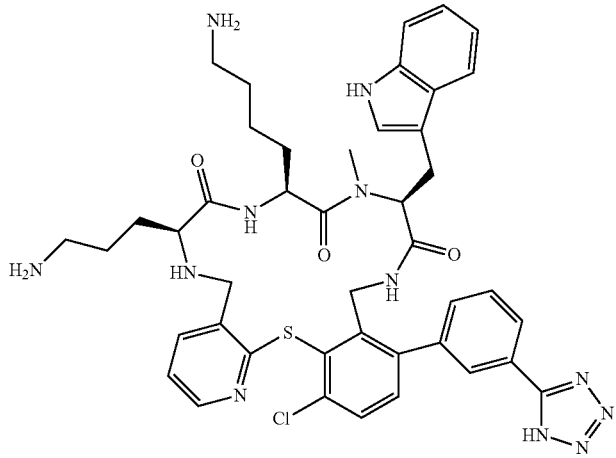<br>(11S,14S,17S)-14-(4-Aminobutyl)-11-(3-aminopropyl)-25-chloro-17-(1H-indol-3-ylmethyl)-16-methyl-22-[3-(1H-tetrazol-5-yl)phenyl]-2-thia-4,10,13,16,19-pentazatricyclo [19.4.0.0³,⁸]pentacosa-1(25),3,5,7,21,23-hexaene-12,15,18-trione | (3-(1H-tetrazol-5-yl)phenyl)boronic acid [CAS-RN 775351-30-9] | 849.4 $[M + H]^+$ |
| 1.04 | 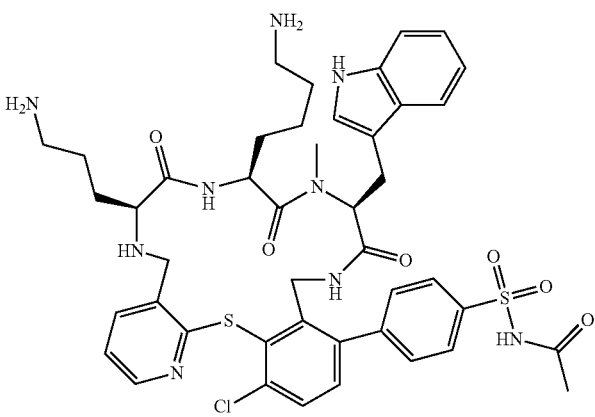<br>N-[4-[(11S,14S,17S)-14-(4-Aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.0³,⁸]pentacosa-1(21),3,5,7,22,24-hexaen-22-yl]phenyl]sulfonylacetamide | (4-(N-acetylsulfamoyl)phenyl)boronic acid [CAS-RN 913835-52-6] | 902.4 $[M + H]^+$ |

| Ex. | Systematic Name | Organoboron reagent | MS |
|---|---|---|---|
| 1.05 | 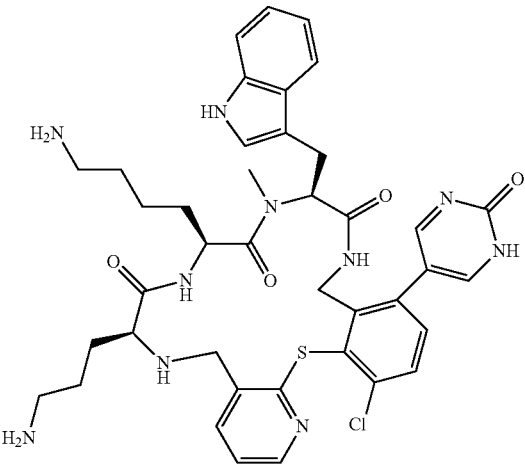

(11S,14S,17S)-14-(4-Aminobutyl)-11-(3-aminopropyl)-25-chloro-17-(1H-indol-3-ylmethyl)-16-methyl-22-(2-oxo-1H-pyrimidin-5-yl)-2-thia-4,10,13,16,19-pentazatricyclo[19.4.0.03,8]pentacosa-1(25),3,5,7,21,23-hexaene-12,15,18-trione | 5-(4,4,5,5-tetramethyl-1,3,2-dioxaborolan-2-yl)pyrimidin-2(1H)-one [CAS-RN 1073354-84-3] | 799.3 [M + H]$^+$ |

Example 2

(11S,14S,17S)-14-(4-Aminobutyl)-11-(3-aminopropyl)-25-chloro-17-(1H-indol-3-ylmethyl)-16-methyl-22-[2-oxo-1-(1H-tetrazol-5-ylmethyl)-4-pyridyl]-2-thia-4,10,13,16,19-pentazatricyclo[19.4.0.03,8]pentacosa-1(25), 3(8),4,6,21,23-hexaene-12,15,18-trione

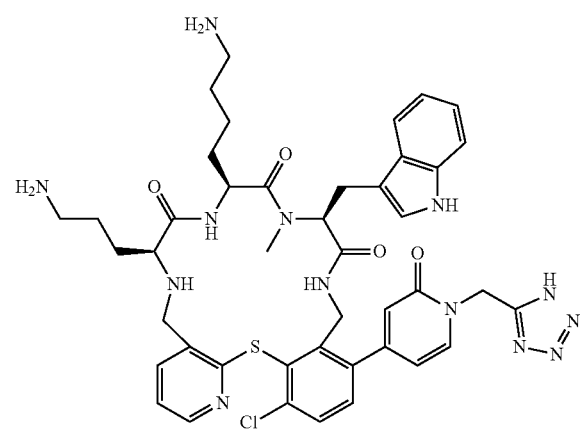

Step 1: (7S,10S,13S)-13-((1H-indol-3-yl)methyl)-10-(4-aminobutyl)-7-(3-aminopropyl)-20-chloro-12-methyl-17-(2-oxo-1,2-dihydropyridin-4-yl)-6,7,9,10,12,13,15,16-octahydrobenzo[b]pyrido[3,2-p][1]thia[5,8,11,14]tetraazacycloheptadecine-8,11,14(5H)-trione trihydrochloride A solution of (11S,14S,17S)-14-(4-amino-butyl)-11-(3-amino-propyl)-25-chloro-22-(2-fluoro-pyridin-4-yl)-17-(1H-indol-3-ylmethyl)-16-methyl-2-thia-4,10,13,16,19-pentaazatricyclo[19.4.0.0^3,8]pentacosa-1(25),3(8),4,6,21, 23hexaene-12,15,18-trione hydrochloride (CAS-RN 2097285-92-0; 300 mg, 0.26 mmol) in 2 M aq. HCl solution (30 mL) was stirred for 16 h at 80° C. After that the solvent was evaporated and the residue triturated in ether and ethyl acetate to produce the title compound (233 mg, 87%). Off-white solid. MS=798.2 [M+H]$^+$.

Step 2: tert-Butyl(4-((7S,10S,13S)-13-((1H-indol-3-yl)methyl)-7-(3-((tert-butoxycarbonyl)amino)propyl)-20-chloro-12-methyl-8,11,14-trioxo-17-(2-oxo-1,2-dihydropyridin-4-yl)-5,6,7,8,9,10,11,12,13,14,15,16-dodecahydrobenzo[b]pyrido[3,2-p][1]thia[5,8,11,14]tetraazacycloheptadecin-10-yl)butyl) carbamate Triethylamine (378 mg, 3.73 mmol) was added to a suspension of (7S,10S,13S)-13-((1H-indol-3-yl)methyl)-10-(4-aminobutyl)-7-(3-aminopropyl)-20-chloro-12-methyl-17-(2-oxo-1,2-dihydropyridin-4-yl)-6,7,9,10,12,13,15,16-octahydrobenzo[b]pyrido[3,2-p][1]thia[5,8,11,14]tetraazacycloheptadecine-8,11,14(5H)-trione trihydrochloride (226 mg, 249 µmol) in dichloromethane (15 mL). After addition of di-tert-butyl dicarbonate (326 mg, 1.49 mmol) and 4-dimethylaminopyridine (21.3 mg, 174 µmol) the reaction mixture was stirred for 2.5 h, then diluted with ethyl acetate and washed with 1 M aq. hydrochloric acid solution and with sat. aq. sodium hydrogencarbonate solution and brine, dried over magnesium sulfate, filtered and evaporated. The crude material was purified by reverse phase prep HPLC as described in example 1, step 1. After lyophilisation the title compound was isolated as a white lyophilised powder (149 mg, 58%). MS m/z: 998.7 [M+H]$^+$.

Step 3: tert-Butyl (3-((7S,10S,13S)-13-((1H-indol-3-yl)methyl)-10-(4-((tert-butoxycarbonyl)amino)butyl)-20-chloro-12-methyl-8,11,14-trioxo-17-(2-oxo-1-((1-trityl-1H-tetrazol-5-yl)methyl)-1,2-dihydropyridin-4-yl)-5,6,7,8,9,10,11,12,13,14,15,16-dodecahydrobenzo[b]pyrido[3,2-p][1]thia[5,8,11,14]tetraazacycloheptadecin-7-yl)propyl)carbamate Potassium carbonate (10.7 mg, 77 µmol) was added to a solution of tert-butyl (4-((7S,10S,13S)-13-((1H-indol-3-yl)methyl)-7-(3-((tert-butoxycarbonyl)amino)propyl)-20-chloro-12-methyl-8,11,14-trioxo-17-(2-oxo-1,2-dihydropyridin-4-yl)-5,6,7,8,9,10,11,12,13,14,15,16-dodecahydrobenzo[b]pyrido[3,2-p][1]thia[5,8,11,14]tetraazacycloheptadecin-10-yl)butyl)carbamate (40 mg, 39 µmol) and 5-(chloromethyl)-1-trityl-1H-tetrazole (CAS-RN 150802-48-5; 16.7 mg, 46.4 µmol, Eq: 1.2) in DMF (1 ml) and stirred at 60° C. for 24 h, then another portion of 5-(chloromethyl)-1-trityl-1H-tetrazole (7.0 mg, 19 µmol) was added, then after another 24 h at 60° C. the reaction mixture was diluted with ethyl acetate and washed with water and brine, dried over magnesium sulfate, filtered, and evaporated. The crude product was purified by preparative HPLC as described in example 1, step 1 to produce the title compound (23 mg, 44%). White lyophylised powder, MS: 1080.8 [M+H-Ph$_3$C]$^+$.

Step 4: (7S,10S,13S)-13-((1H-Indol-3-yl)methyl)-17-(1-((1H-tetrazol-5-yl)methyl)-2-oxo-1,2-dihydropyridin-4-yl)-10-(4-aminobutyl)-7-(3-aminopropyl)-20-chloro-12-methyl-6,7,9,10,12,13,15,16-octahydrobenzo[b]pyrido[3,2-p][1]thia[5,8,11,14]tetraazacycloheptadecine-8,11,14(5H)-trione Trifluoroacetic acid (300 mg) was added to a solution of tert-butyl (3-((7S,10S,13S)-13-((1H-indol-3-yl)methyl)-10-(4-((tert-butoxycarbonyl)amino)butyl)-20-chloro-12-methyl-8,11,14-trioxo-17-(2-oxo-1-((1-trityl-1H-tetrazol-5-yl)methyl)-1,2-dihydropyridin-4-yl)-5,6,7,8,9,10,11,12,13,14,15,16-dodecahydrobenzo[b]pyrido[3,2-p][1]thia[5,8,11,14]tetraazacycloheptadecin-7-yl)propyl)carbamate (23 mg, 17.4 µmol) and triisopropylsilane (27.5 mg, 174 µmol) in dichloromethane (1.2 mL) and stirred at 0° C. for 4 h, then the reaction mixture was concentrated and the crude product purified by preparative HPLC as described in example 1, step 2 to produce the title compound as the trifluoroacetate salt (11 mg, 54%). White lyophilised powder, MS: 880.4 [M+H]$^+$.

Example 3

(11S,14S,17S)-14-(4-Aminobutyl)-11-(3-aminopropyl)-25-chloro-17-(1H-indol-3-ylmethyl)-16-methyl-22-[4-(5-oxo-4H-1,2,4-thiadiazol-3-yl)phenyl]-2-thia-4,10,13,16,19-pentazatricyclo[19.4.0.03,8]pentacosa-1(25), 3(8),4,6,21,23-hexaene-12,15,18-trione

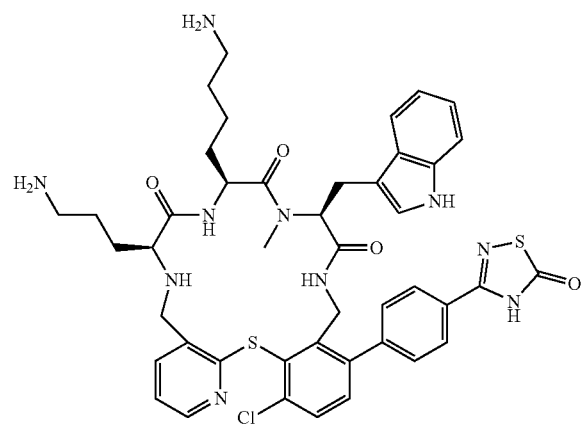

Step 1: tert-Butyl 3-(((7S,10S,13S)-10-(4-((tert-butoxycarbonyl)amino)butyl)-7-(3-((tert-butoxycarbonyl)amino)propyl)-20-chloro-17-(4-cyanophenyl)-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate The title compound was produced in analogy to example 1, step 1, replacing 4-boronobenzenesulfonic acid by (4-cyanophenyl)boronic acid [CAS-RN 126747-14-6]. White lyophilised powder, MS: 1106.5 [M+H]+.

Step 2: 4-((7S,10S,13S)-13-((1H-Indol-3-yl)methyl)-10-(4-aminobutyl)-7-(3-aminopropyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-17-yl)benzonitrile The title compound was produced in analogy to example 1, step 2 from tert-butyl 3-(((7S,10S,13S)-10-(4-((tert-butoxycarbonyl)amino)butyl)-7-(3-((tert-butoxycarbonyl)amino)propyl)-20-chloro-17-(4-cyanophenyl)-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate. White lyophilised poder, MS: 806.4 [M+H]$^+$.

Step 3: tert-Butyl 3-(((7S,10S,13S)-10-(4-((tert-butoxycarbonyl)amino)butyl)-7-(3-((tert-butoxycarbonyl)amino)propyl)-20-chloro-17-(4-cyanophenyl)-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate The title compound was produced in analogy to example 2, step 2 from 4-((7S,10S,13S)-13-((1H-indol-3-yl)methyl)-10-(4-aminobutyl)-7-(3-aminopropyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-17-yl)benzonitrile and di-tert-butyl dicarbonate. White lyophilised poder, MS: 1006.8 [M+H]$^+$.

Step 4: tert-Butyl (3-((7S,10S,13S)-13-((1H-indol-3-yl)methyl)-10-(4-((tert-butoxycarbonyl)amino)butyl)-20-chloro-17-(4-((Z)—N'-hydroxycarbamimidoyl)phenyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-7-yl)propyl)carbamate Hydroxylamine (41.3 mg, 0.63 mmol) was added to a solution of tert-butyl (4-((7S,10S,13S)-13-((1H-indol-3-yl)methyl)-7-(3-((tert-butoxycarbonyl)amino)propyl)-20-chloro-17-(4-cyanophenyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-10-yl)butyl)carbamate (140 mg, 125 µmol) in ethanol (7 mL). The reaction mixture was stirred at 75° C. for 48 h, then concentrated to produce the title compound (146 mg, which was used directly in the next step. White solid, MS: 1039.6 [M+H]$^+$.

Step 5: (7S,10S,13S)-13-((1H-Indol-3-yl)methyl)-10-(4-aminobutyl)-7-(3-aminopropyl)-20-chloro-12-methyl-17-(4-(5-oxo-4,5-dihydro-1,2,4-thiadiazol-3-yl)phenyl)-6,7,9,10,12,13,15,16-octahydrobenzo[b]pyrido[3,2-p][1]thia[5,8,11,14]tetraazacycloheptadecine-8,11,14(5H)-trione 1,1'-Thiocarbonyldiimidazole (9.3 mg, 52 µmol) was added to a solution of tert-butyl (3-((7S,10S,13S)-13-((1H-indol-3-yl)methyl)-10-(4-((tert-butoxycarbonyl)amino)butyl)-20-chloro-17-(4-((Z)—N'-hydroxycarbamimidoyl)phenyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-7-yl)propyl)carbamate (40 mg, 35 µmol) in tetrahydrofuran (1 mL) at room temperature, then after 40 min the reaction mixture was partitioned between dichloromethane and water. The organic layer was washed with brine, dried over magnesium sulfate, filtered, and evaporated. The residue was dissolved in tetrahydrofuran (1 mL), then boron trifluoride diethyl etherate (14.8 mg, 104 µmol) was added dropwise and the resulting mixture stirred for 3 h, then the product was purified by preparative HPLC as described in example 1, step 2 to produce the title compound as the trifluoroacetate salt (3.3 mg, 8%). White lyophilised powder, MS: 881.3 [M+H]+.

Example 4

(11S,14S,17S)-14-(4-Aminobutyl)-11-(3-aminopropyl)-25-chloro-17-(1H-indol-3-ylmethyl)-16-methyl-22-[4-(5-oxo-4H-1,2,4-oxadiazol-3-yl)phenyl]-2-thia-4,10,13,16,19-pentazatricyclo[19.4.0.0³,⁸]pentacosa-1(25), 3(8),4,6,21,23-hexaene-12,15,18-trione

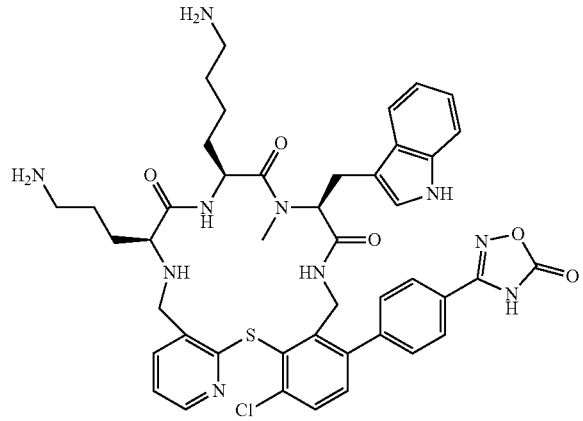 [SMILES: CN1C(=O)[C@H](CCCCN)NC(=O)[C@H](CCCN)NCc2cccnc2Sc2c(Cl)ccc(-c3ccc(-c4noc(=O)[nH]4)cc3)c2CNC(=O)[C@@H]1Cc1c[nH]c2ccccc12]

Step 1: tert-Butyl (4-(((7S,10S,13S)-13-((1H-indol-3-yl)methyl)-7-(3-((tert-butoxycarbonyl)amino)propyl)-20-chloro-12-methyl-8,11,14-trioxo-17-(4-(5-oxo-4,5-dihydro-1,2,4-oxadiazol-3-yl)phenyl)-5,6,7,8,9,10,11,12,13,14,15,16-dodecahydrobenzo[b]pyrido[3,2-p][1]thia[5,8,11,14]tetraazacycloheptadecin-10-yl)butyl)carbamate Isobutyl chloroformate (4.8 mg, 35 µmol) was added dropwise at 0° C. to a solution of tert-butyl (4-(((7S,10S,13S)-13-((1H-indol-3-yl)methyl)-7-(3-((tert-butoxycarbonyl)amino)propyl)-20-chloro-17-(4-((Z)—N'-hydroxycarbamimidoyl)phenyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-10-yl)butyl)carbamate (Example 3, step 4; 41 mg, 36 µmol) and pyridine (3 mg, 39 µmol) in N,N-dimethylformamide (1 mL). The solution was allowed to reach room temperature over 18 h, then partitioned between water and ethyl acetate. The organic layer was washed with brine, dried over magnesium sulfate, filtered, and evaporated. he reaction was diluted with water and extracted with EtOAc three times. The combined organic extracts were washed with water, brine, dried over magnesium sulfate, filtered and concentrated in vacuo. The residue was suspended in toluene (1.5 mL) and heated at 140° C. in a sealed tube for 24 h, then the reaction mixture was concentrated. The crude product was purified by preparative HPLC as described in Example 1 to produce the title compound (11 mg, 27%). White lyophilised powder, MS: 1065.7 [M+H]+.

Step 2: (7S,10S,13S)-13-((1H-Indol-3-yl)methyl)-10-(4-aminobutyl)-7-(3-aminopropyl)-20-chloro-12-methyl-17-(4-(5-oxo-4,5-dihydro-1,2,4-oxadiazol-3-yl)phenyl)-6,7,9,10,12,13,15,16-octahydrobenzo[b]pyrido[32-p][1]thia[5,8,11,14]tetraazacycloheptadecine-8,11,14(5H)-trione The title compound was produced in analogy to example 1, step 2 from tert-butyl (4-((7S,10S,13S)-13-((1H-indol-3-yl)methyl)-7-(3-((tert-butoxycarbonyl)amino)propyl)-20-chloro-12-methyl-8,11,14-trioxo-17-(4-(5-oxo-4,5-dihydro-1,2,4-oxadiazol-3-yl)phenyl)-5,6,7,8,9,10,11,12,13,14,15,16-dodecahydrobenzo[b]pyrido[3,2-p][1]thia[5,8,11,14]tetraazacycloheptadecin-10-yl)butyl)carbamate. White lyophilised powder, MS: 865.3 [M+H]+.

Example 5

(11S,14S,17S)-14-(4-Aminobutyl)-1-(3-aminopropyl)-17-(1H-indol-3-ylmethyl)-16-methyl-22-[4-(1H-tetrazol-5-yl)phenyl]-2-thia-4,10,13,16,19-pentazatricyclo[19.4.0.0³,⁸]pentacosa-1(25), 3(8),4,6, 21,23-hexaene-12,15,18-trione

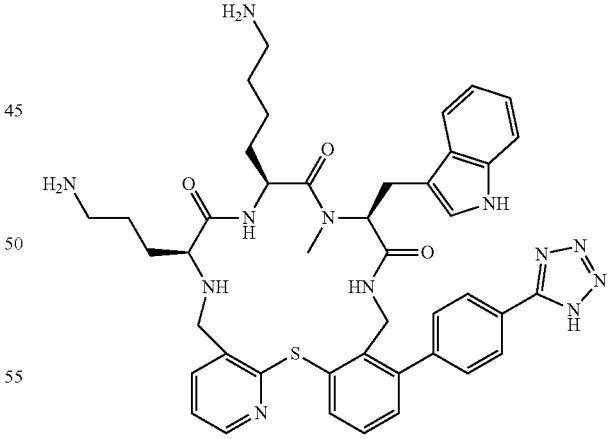

The title compound was produced in analogy to example 1.02, replacing tert-butyl 3-(((7S,10S,13S)-17-bromo-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate by tert-butyl 3-{[(11S,14S,17S)-22-bromo-14-(4-{[(tert-butoxy)carbonyl]amino}butyl)-11-(3-{[(tert-butoxy)carbonyl]

amino}propyl)-16-methyl-12,15,18-trioxo-2-thia-4,10,13,
16,19-pentaazatricyclo[19.4.0.0^{3,8}]pentacosa-1(25),3
(8),4,6,21,23-hexaen-17-yl]methyl}-1H-indole-1-carboxy-
late (intermediate 1). White solid, MS: 815.6 [M+H]⁺.

Example 6

4-[(11S,14S,17S)-14-(4-Aminobutyl)-1-(3-amino-
propyl)-25-chloro-17-(1H-indol-3-ylmethyl)-16-
methyl-12,15,18-trioxo-2-thia-4,7,10,13,16,19-
hexazatricyclo[19.4.0.03,8]pentacosa-1(25), 3(8),4,
6,21,23-hexaen-22-yl]benzenesulfonic acid

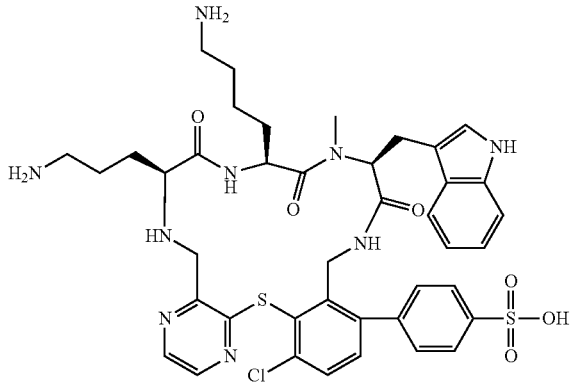 [SMILES: CN1C(=O)[C@H](CCCCN)NC(=O)[C@H](CCCN)NCc2nccnc2Sc2c(Cl)ccc(-c3ccc(S(=O)(=O)O)cc3)c2CNC(=O)[C@@H]1Cc1c[nH]c2ccccc12]

The title compound was produced in analogy to example
1, replacing tert-butyl 3-(((7S,10S,13S)-17-bromo-10-(4-
((tert-butoxycarbonyl)amino)butyl)-7-(3-((tert-butoxycar-
bonyl)amino)propyl)-20-chloro-12-methyl-8,11,14-trioxo-
5,6,7,8,9,10,11,12,13,14,15,16-dodecahydrobenzo[b]pyrido
[3,2-p][1,5,8,11,14]thiatetraazacycloheptadecin-13-yl)
methyl)-1H-indole-1-carboxylate by tert-butyl 3-(((7S,10S,
13S)-17-bromo-10-(4-((tert-butoxycarbonyl)amino)butyl)-
7-(3-((tert-butoxycarbonyl)amino)propyl)-20-chloro-12-
methyl-8,11,14-trioxo-5,6,7,8,9,10,11,12,13,14,15,16-
dodecahydrobenzo[b]pyrazino[2,3-p][1,5,8,11,14]
thiatetraazacycloheptadecin-13-yl)methyl)-1H-indole-1-
carboxylate (intermediate 1.01). White solid, MS: 862.3
[M+H]⁺.

Example 7

4-[(11S,14S,17S)-14-(4-Aminobutyl)-11-(3-amino-
propyl)-25-fluoro-17-(1H-indol-3-ylmethyl)-16-
methyl-12,15,18-trioxo-2-thia-4,10,13,16,19-pen-
tazatricyclo[19.4.0.03,8]pentacosa-1(25), 3(8),4,6,
21,23-hexaen-22-yl]benzenesulfonic acid

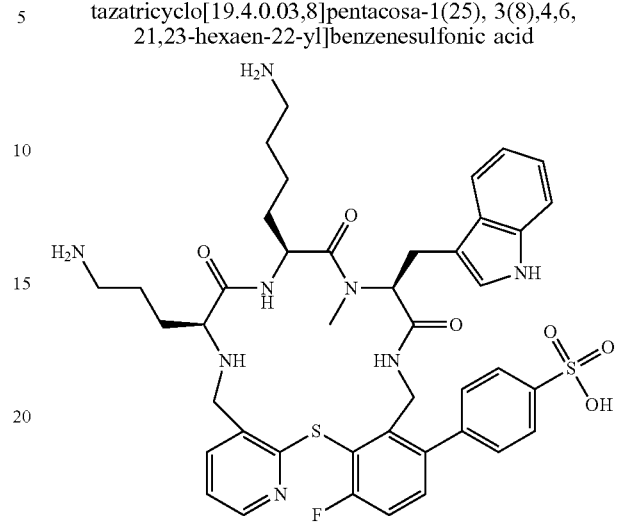

The title compound was produced in analogy to example
1, replacing tert-butyl 3-(((7S,10S,13S)-17-bromo-10-(4-
((tert-butoxycarbonyl)amino)butyl)-7-(3-((tert-butoxycar-
bonyl)amino)propyl)-20-chloro-12-methyl-8,11,14-trioxo-
5,6,7,8,9,10,11,12,13,14,15,16-dodecahydrobenzo[b]pyrido
[3,2-p][1,5,8,11,14]thiatetraazacycloheptadecin-13-yl)
methyl)-1H-indole-1-carboxylate by tert-butyl 3-(((7S,10S,
13S)-17-bromo-10-(4-((tert-butoxycarbonyl)amino)butyl)-
7-(3-((tert-butoxycarbonyl)amino)propyl)-20-fluoro-12-
methyl-8,11,14-trioxo-5,6,7,8,9,10,11,12,13,14,15,16-
dodecahydrobenzo[b]pyrido[3,2-p][1,5,8,11,14]
thiatetraazacycloheptadecin-13-yl)methyl)-1H-indole-1-
carboxylate (intermediate 1.02). White lyophilised powder,
MS: 845.6 [M+H]⁺.

The following examples were produced in analogy to
example 7, replacing 4-boronosulfonic acid with the appro-
priate organoboron reagent.

| Ex. | Systematic Name | Organoboron reagent | MS |
|---|---|---|---|
| 7.01 | ![structure] | (4-(1H-tetrazol-5-yl)phenyl)boronic acid [CAS-RN 179942-55-3] | 833.4 [M + H]⁺ |

(11S,14S,17S)-14-(4-aminobutyl)-11-(3-aminopropyl)-25-fluoro-17-(1H-indol-3-
ylmethyl)-16-methyl-22-[4-(1H-tetrazol-5-yl)phenyl]-2-thia-4,10,13,16,19-
pentazatricyclo[19.4.0.03,8]pentacosa-1(25),3(8),4,6,21,23-hexaene-12,15,18-trione -continued

| Ex. | Systematic Name | Organoboron reagent | MS |
|---|---|---|---|
| 7.02 | 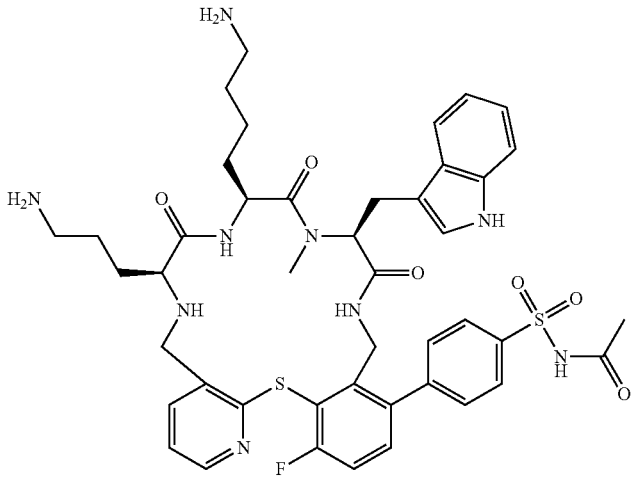 N-[4-[(11S,14S,17S)-14-(4-Aminobutyl)-11-(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]phenyl]sulfonylacetamide | (4-(N-acetylsulfamoyl)-phenyl)boronic acid [CAS-RN 913835-52-6] | 886.4 [M + H]+ |
| 7.03 | 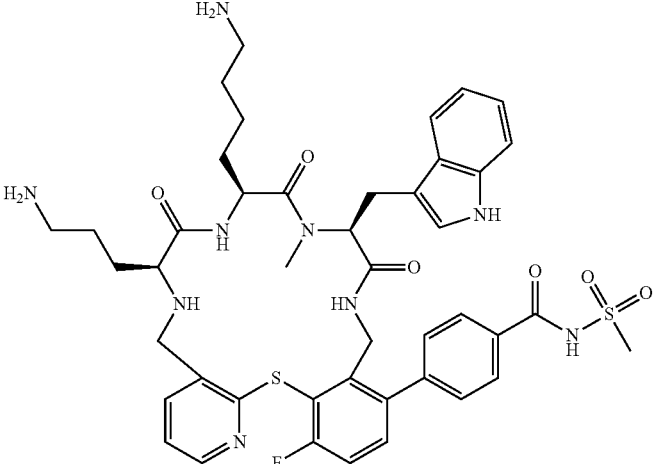 4-[(11S,14S,17S)-14-(4-Aminobutyl)-11-(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]-N-methylsulfonyl-benzamide | (4-(N-acetylsulfamoyl)-phenyl)boronic acid [CAS-RN 913835-52-6] | 886.4 [M + H]+ |

Example 8

4-[(11S,14S,17S)-11,14-Bis(3-aminopropyl)-25-chloro-17-(1H-indol-3-ylmethyl)-16-methyl-12,15,18-trioxo-2-thia-4,10,13,16,19-pentazatricyclo[19.4.0.0³,⁸]pentacosa-1(21),3,5,7,22,24-hexaen-22-yl]benzenesulfonic acid

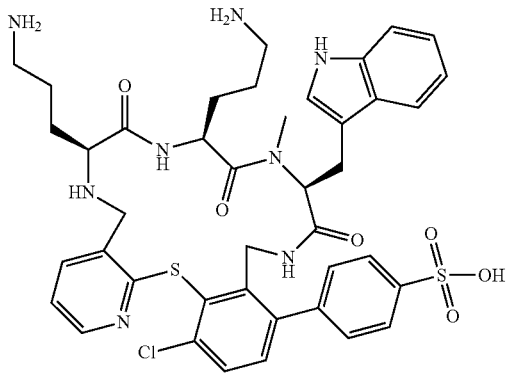 [SMILES: CN1C(=O)[C@H](CCCN)NC(=O)[C@H](CCCN)NCc2cccnc2Sc2c(Cl)ccc(-c3ccc(S(=O)(=O)O)cc3)c2CNC(=O)[C@@H]1Cc1c[nH]c2ccccc12]

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate by tert-butyl 3-{[(11S,14S,17S)-22-bromo-11,14-bis(3-{[(tert-butoxy)carbonyl]amino}propyl)-25-chloro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate (intermediate 1.3). White lyophilised powder, MS: 847.3 [M+H]⁺.

The following examples were produced in analogy to example 8, replacing 4-boronosulfonic acid with the appropriate organoboron reagent.

| Ex. | Systematic Name | Organoboron reagent | MS |
|---|---|---|---|
| 8.01 | (11S,14S,17S)-11,14-Bis(3-aminopropyl)-25-chloro-17-(1H-indol-3-ylmethyl)-16-methyl-22-[4-(1H-tetrazol-5-yl)phenyl]-2-thia-4,10,13,16,19-pentazatricyclo[19.4.0.03,8]pentacosa-1(21),3,5,7,22,24-hexaene-12,15,18-trione | (4-(1H-tetrazol-5-yl)phenyl)boronic acid [CAS-RN 179942-55-3] | 835.3 [M + H]⁺ |
| 8.02 | (11S,14S,17S)-11,14-Bis(3-aminopropyl)-25-chloro-17-(1H-indol-3-ylmethyl)-16-methyl-22-(2-oxo-1H-pyrimidin-5-yl)-2-thia-4,10,13,16,19-pentazatricyclo[19.4.0.03,8]pentacosa-1(21),3,5,7,22,24-hexaene-12,15,18-trione | 5-(4,4,5,5-tetramethyl-1,3,2-dioxaborolan-2-yl)pyrimidin-2(1H)-one [CAS-RN 1073354-84-3] | 785.3 [M + H]⁺ |

Example 9

4-[(11S,14S,17S)-11,14-Bis(3-aminopropyl)-25-fluoro-17-(1H-indol-3-ylmethyl)-16-methyl-12,15,18-trioxo-2-thia-4,10,13,16,19-pentazatricyclo[19.4.0.0³,⁸]pentacosa-1(25), 3(8),4,6,21,23-hexaen-22-yl]benzenesulfonic acid

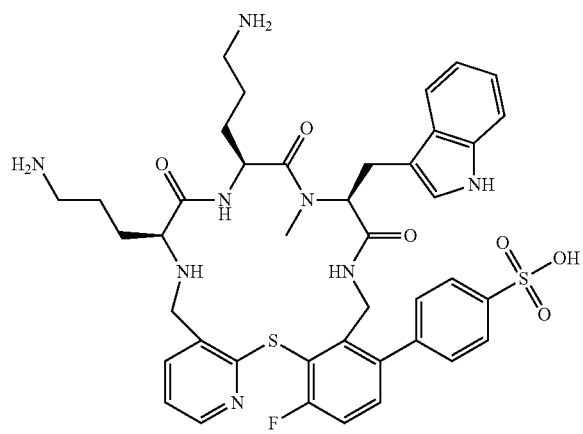 [SMILES: CN1C(=O)[C@H](CCCN)NC(=O)[C@H](CCCN)NCc2cccnc2Sc2c(F)ccc(-c3ccc(S(=O)(=O)O)cc3)c2CNC(=O)[C@@H]1Cc1c[nH]c2ccccc12]

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate by tert-butyl 3-{[(11S,14S,17S)-22-bromo-11,14-bis(3-{[(tert-butoxy)carbonyl]amino}propyl)-25-fluoro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate (intermediate 1.04). White lyophilised powder, MS: 831.3 [M+H]⁺.

Example 9.01

(11S,14S,17S)-11,14-Bis(3-aminopropyl)-25-fluoro-17-(1H-indol-3-ylmethyl)-16-methyl-22-[4-(1H-tetrazol-5-yl)phenyl]-2-thia-4,10,13,16,19-pentazatricyclo[19.4.0.03,8]pentacosa-1(25), 3(8),4,6,21,23-hexaene-12,15,18-trione

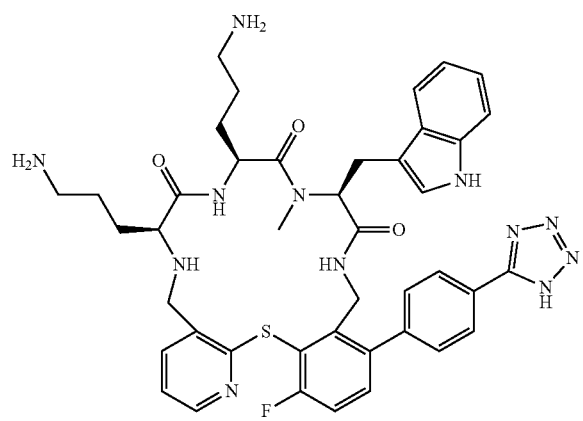 [SMILES: CN1C(=O)[C@H](CCCN)NC(=O)[C@H](CCCN)NCc2cccnc2Sc2c(F)ccc(-c3ccc(-c4nnn[nH]4)cc3)c2CNC(=O)[C@@H]1Cc1c[nH]c2ccccc12]

The title compound was produced in analogy to example 9, replacing 4-boronosulfonic acid by (4-(1H-tetrazol-5-yl)phenyl)boronic acid [CAS-RN 179942-55-3]. White solid, MS: 819.4 [M+H]⁺.

Example 10

[4-[(11S,14S,17S)-11,14-Bis(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25), 3(8),4,6,21,23-hexaen-22-yl]phenyl]phosphonic acid

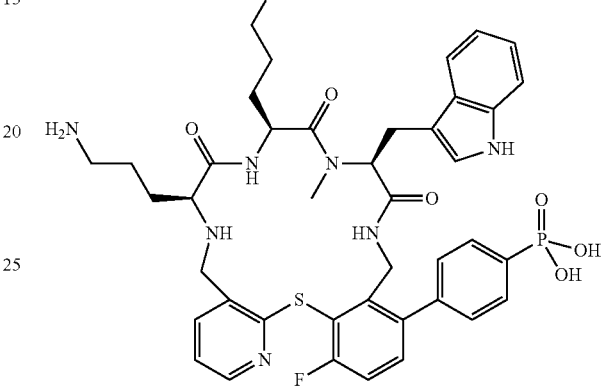

Step 1: tert-Butyl 3-(((7S,10lS,13S)-7,10-bis(3-((tert-butoxycarbonyl)amino)propyl)-17-(4-(dimethoxyphosphoryl)phenyl)-20-fluoro-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-13-yl)methyl)-1H-indole-1-carboxylate A solution of tert-butyl 3-(((7S,10S,13S)-17-bromo-7,10-bis(3-((tert-butoxycarbonyl)amino)propyl)-20-fluoro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate (intermediate 1.04; 80 mg, 75.9 µmol), dimethyl (4-(4,4,5,5-tetramethyl-1,3,2-dioxaborolan-2-yl)phenyl)phosphonate (CAS-RN 852204-67-2; 23.7 mg, 75.9 µmol) and sodium carbonate (20.1 mg, 190 µmol) in 1,4-dioxane/water 6:1 (1.25 mL) was sparged with argon for 2 minutes whilst sonicating the vessel in an ultrasound bath, then tetrakis(triphenylphosphine)palladium(0) (17.5 mg, 15.2 µmol) was added. The tube was sealed and heated at 130° C. for 10 min under microwave irradiation, then the reaction mixture was partitioned between ethyl acetate and 2 M aq. sodium carbonate solution. The organic layer was washed with brine, dried over magnesium sulfate, filtered and concentrated in vacuo. The residue was purified as described in example 1, step 1 to produce the title compound (78 mg, 89%). Off-white lyophilised powder, MS: 1159.7 [M+H]⁺.

Step 2: (4-((7S,10S,13S)-13-((1H-indol-3-yl)methyl)-7,10-bis(3-aminopropyl)-20-fluoro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-17-yl)phenyl)phosphonic acid Trifluoroacetic acid (1.15 g) was added to a solution of tert-butyl 3-(((7S,10S,13S)-7,10-bis(3-((tert-butoxycarbonyl)amino)propyl)-17-(4-(dimethoxyphosphoryl)phenyl)-20-fluoro-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-13-yl)methyl)-1H-indole-1-carboxylate (78 mg, 67.3 µmol) in dichloromethane (2 mL) and stirred at room temperature for 6 h, then volatiles were removed and the residue was dissolved in acetonitrile/water 1:9 and stirred overnight at room temperature, then lyophilised. The residue was dissolved in dichloromethane (2 mL), then bromotrimethylsilane (155 mg, 1.01 mmol), then after 24 h the crude product was purified by reverse phase preparative HPLC as described in example 1, step 2 to produce the title compound as the trifluoroacetate salt (35 mg, 44%). White lyophilised powder, MS: 831.3 [M+H]$^+$.

The following examples were produced in analogy to example 10, replacing tert-butyl 3-{[(11S,14S,17S)-22-bromo-11,14-bis(3-{[(tert-butoxy)carbonyl]amino}propyl)-25-fluoro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate by the appropriate starting material.

| Ex. | Systematic Name | Starting material | MS |
|---|---|---|---|
| 10.01 | 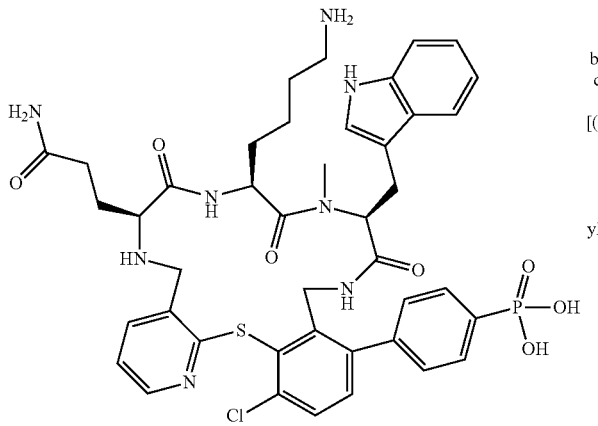<br>[4-[(11S,14S,17S)-14-(4-Aminobutyl)-11-(3-amino-3-oxo-propyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]phenyl]phosphonic acid | tert-butyl 3-{[(11S,14S,17S)-22-bromo-14-(4-{[(tert-butoxy)carbonyl]amino}-butyl)-25-chloro-16-methyl-12,15,18-trioxo-11-{2-[(triphenylmethyl)carbamoyl]ethyl}-2-thia-4,10,13,16,19-pentaazatricyclo-[19.4.0.0^{3,8}]pentacosa-1(25),3(8),4,6,21,23-hexaen-17-yl]methyl}-1H-indole-1-carboxylate (intermediate 1.05) | 875.6 [M + H]$^+$ |
| 10.02 | 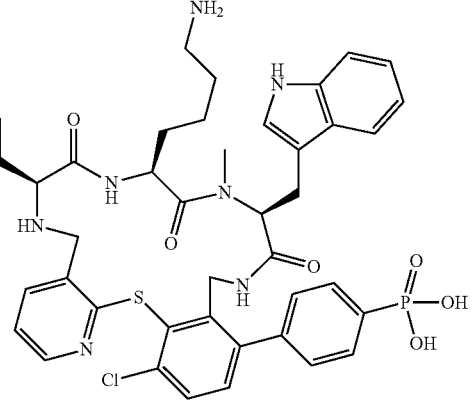<br>[4-[(11S,14S,17S)-14-(4-Aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]phenyl]phosphonic acid | tert-butyl 3-(((7S,10S,13S)-17-bromo-10-(4-((tert-butoxycarbonyl)amino)-butyl)-7-(3-((tert-butoxycarbonyl)amino)-propyl)-20-chloro-12-methyl-8,11,14-trioxo-5,6,7,8,9,10,11,12,13,14,15,16-dodecahydrobenzo[b]-pyrido[3,2-p][1,5,8,11,14]thiatetra-azacycloheptadecin-13-yl)methyl)-1H-indole-1-carboxylate [CAS-RN 2097294-18-1] | 861.4 [M + H]$^+$ |

Example 11

4-[(11S,14S,17S)-14-(4-Aminobutyl)-11-(3-aminopropyl)-17-(1H-indol-3-ylmethyl)-16,25-dimethyl-12,15,18-trioxo-2-thia-4,10,13,16,19-pentazatricyclo[19.4.0.0^3,8]pentacosa-1(25), 3(8),4,6,21,23-hexaen-22-yl]benzenesulfonic acid

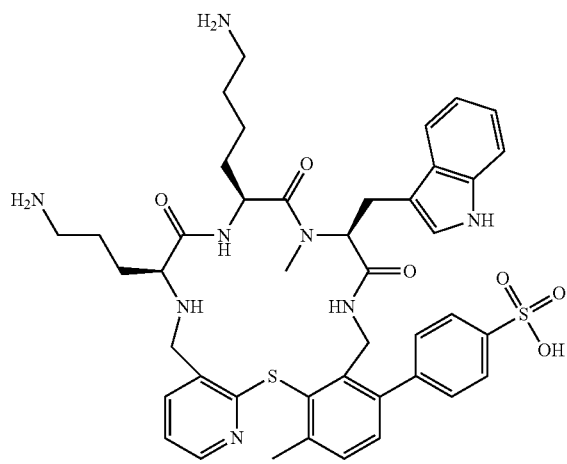 [SMILES: Cc1ccc(-c2ccc(S(=O)(=O)O)cc2)c2c1Sc1ncccc1CN[C@@H](CCCN)C(=O)N[C@@H](CCCCN)C(=O)N(C)[C@@H](Cc1c[nH]c3ccccc13)C(=O)NC2]

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate by tert-butyl 3-(((7S,10S,13S)-17-bromo-10-(4-((tert-butoxycarbonyl)amino)butyl)-7-(3-((tert-butoxycarbonyl)amino)propyl)-12,20-dimethyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate (intermediate 1.06). White lyophilised powder, MS: 841.4 [M+H]$^+$.

Example 11.01

(11S,14S,17S)-14-(4-Aminobutyl)-11-(3-aminopropyl)-17-(1H-indol-3-ylmethyl)-16,25-dimethyl-22-[4-(1H-tetrazol-5-yl)phenyl]-2-thia-4,10,13,16,19-pentazatricyclo[19.4.0.0^3,8]pentacosa-1(25), 3(8),4,6,21,23-hexaene-12,15,18-trione

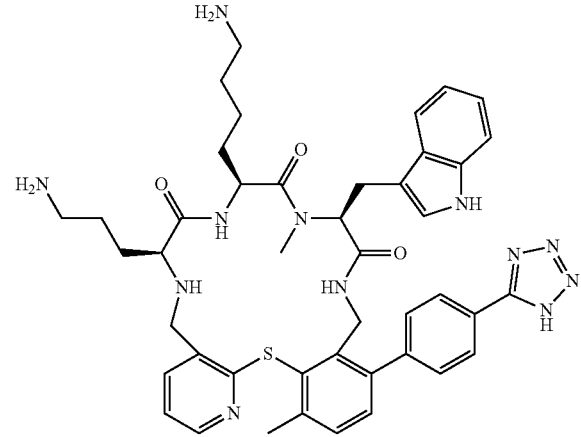 [SMILES: Cc1ccc(-c2ccc(-c3nnn[nH]3)cc2)c2c1Sc1ncccc1CN[C@@H](CCCN)C(=O)N[C@@H](CCCCN)C(=O)N(C)[C@@H](Cc1c[nH]c3ccccc13)C(=O)NC2]

The title compound was produced in analogy to example 11, replacing 4-boronosulfonic acid by (4-(1H-tetrazol-5-yl)phenyl)boronic acid [CAS-RN 179942-55-3]. White lyophilised powder, MS: 829.4 [M+H]$^+$.

Example 12

4-[(11S,14S,17S)-14-(4-Aminobutyl)-11-(2-aminoethyl)-25-chloro-17-(1H-indol-3-ylmethyl)-16-methyl-12,15,18-trioxo-2-thia-4,10,13,16,19-pentazatricyclo[19.4.0.0^3,8]pentacosa-1(25), 3(8),4,6,21,23-hexaen-22-yl]benzenesulfonic acid

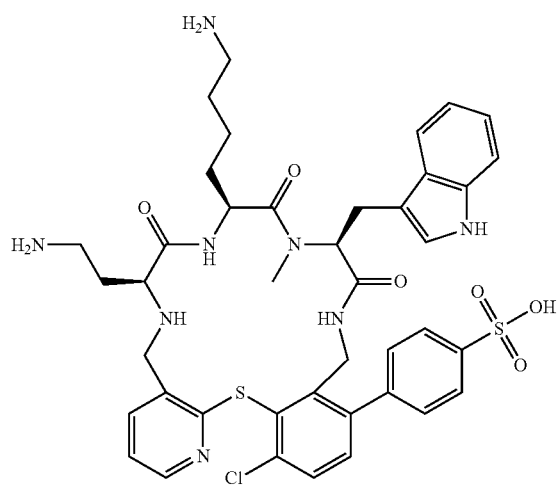 [SMILES: CN1C(=O)[C@H](CCCCN)NC(=O)[C@H](CCN)NCc2cccnc2Sc2c(Cl)ccc(-c3ccc(S(=O)(=O)O)cc3)c2CNC(=O)[C@@H]1Cc1c[nH]c2ccccc12]

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate by tert-butyl 3-{[(11S,14S,17S)-22-bromo-14-(4-{[(tert-butoxy)carbonyl]amino}butyl)-11-(2-{[(tert-butoxy)carbonyl]amino}ethyl)-25-chloro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate (intermediate 1.07). White lyophilised powder, MS: 848.5 [M+H]$^+$.

Example 13

4-[(11S,14S,17S)-11-(2-Aminoethyl)-14-(3-aminopropyl)-25-chloro-17-(1H-indol-3-ylmethyl)-16-methyl-12,15,18-trioxo-2-thia-4,10,13,16,19-pentazatricyclo[19.4.0.0^3,8]pentacosa-1(25), 3(8),4,6,21,23-hexaen-22-yl]benzenesulfonic acid

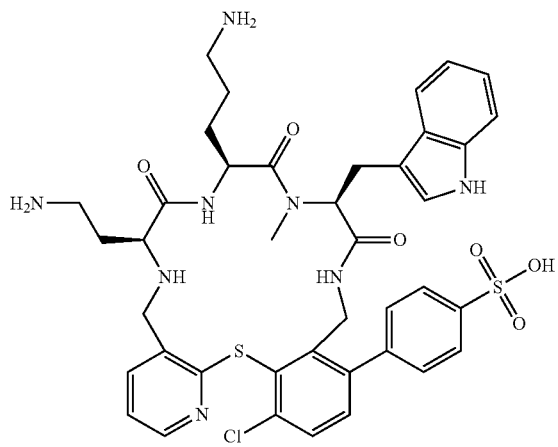 [SMILES: CN1C(=O)[C@H](CCCN)NC(=O)[C@H](CCN)NCc2cccnc2Sc2c(Cl)ccc(-c3ccc(S(=O)(=O)O)cc3)c2CNC(=O)[C@@H]1Cc1c[nH]c2ccccc12]

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate by tert-butyl 3-{[(11S,14S,17S)-22-bromo-11-(2-{[(tert-butoxy)carbonyl]amino}ethyl)-14-(3-{[(tert-butoxy)carbonyl]amino}propyl)-25-chloro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate (intermediate 1.08). White lyophilised powder, MS: 833.6 [M+H]⁺.

Example 14

4-[(11S,14S,17S)-14-(3-Aminopropyl)-25-chloro-17-(1H-indol-3-ylmethyl)-11,16-dimethyl-12,15,18-trioxo-2-thia-4,10,13,16,19-pentazatricyclo[19.4.0.03,8]pentacosa-1(25), 3(8),4,6,21,23-hexaen-22-yl]benzenesulfonic acid

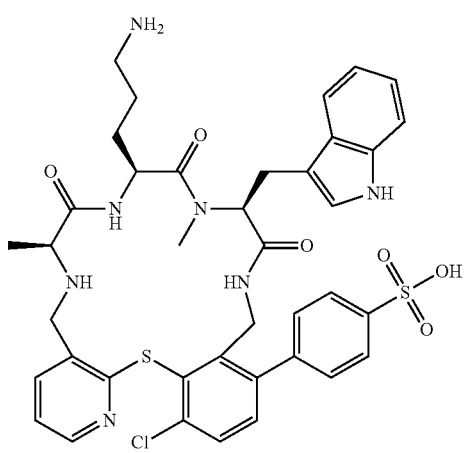 [SMILES: C[C@@H]1NCc2cccnc2Sc2c(Cl)ccc(-c3ccc(S(=O)(=O)O)cc3)c2CNC(=O)[C@H](Cc2c[nH]c3ccccc23)N(C)C(=O)[C@H](CCCN)NC1=O]

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate by tert-butyl 3-{[(11S,14S,17S)-22-bromo-14-(3-{[(tert-butoxy)carbonyl]amino}propyl)-25-chloro-11,16-dimethyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate (intermediate 1.09). White lyophilised powder, MS: 804.5 [M+H]⁺.

Example 15

4-[(11S,14S,17S)-14-(4-Aminobutyl)-11-(3-aminopropyl)-17-(1H-indol-3-ylmethyl)-25-methoxy-16-methyl-12,15,18-trioxo-2-thia-4,10,13,16,19-pentazatricyclo[19.4.0.03,8]pentacosa-1(25), 3(8),4,6,21,23-hexaen-22-yl]benzenesulfonic acid

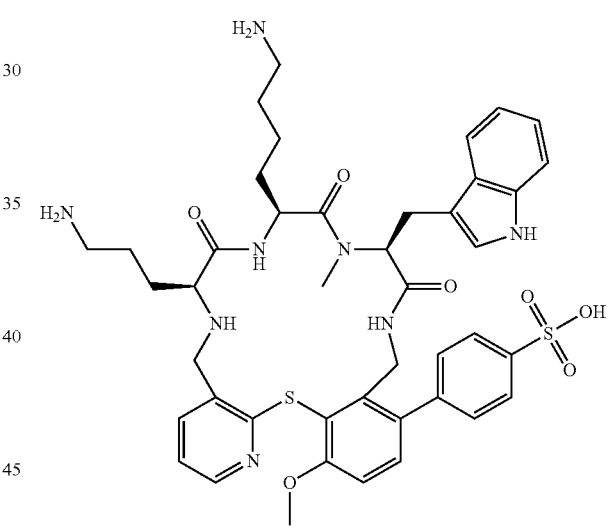

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate by tert-butyl 3-{[(11S,14S,17S)-22-bromo-14-(4-{[(tert-butoxy)carbonyl]amino}butyl)-11-(3-{[(tert-butoxy)carbonyl]amino}propyl)-25-methoxy-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate (intermediate 1.10). White lyophilised powder, MS: 857.7 [M+H]⁺.

Example 15.01

(11S,14S,17S)-14-(4-Aminobutyl)-1-(3-aminopropyl)-17-(1H-indol-3-ylmethyl)-25-methoxy-16-methyl-22-[4-(1H-tetrazol-5-yl)phenyl]-2-thia-4,10,13,16,19-pentazatricyclo[19.4.0.0³,⁸]pentacosa-1(25),3(8),4,6,21,23-hexaene-12,15,18-trione

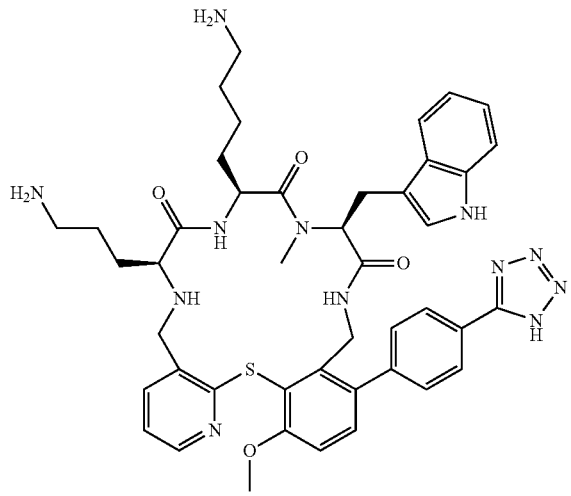 [SMILES: COc1ccc(-c2ccc(-c3nnn[nH]3)cc2)c2c1Sc1ncccc1CN[C@@H](CCCN)C(=O)N[C@@H](CCCCN)C(=O)N(C)[C@@H](Cc1c[nH]c3ccccc13)C(=O)NC2]

The title compound was produced in analogy to example 15, replacing 4-boronosulfonic acid by (4-(1H-tetrazol-5-yl)phenyl)boronic acid [CAS-RN 179942-55-3]. White lyophilised powder, MS: 845.6 $[M+H]^+$.

Example 16

N-[4-[(11S,14S,7S)-14-(4-aminobutyl)-25-chloro-11-(3-hydroxypropyl)-17-(1H-indol-3-ylmethyl)-16-methyl-12,15,18-trioxo-2-thia-4,10,13,16,19-pentazatricyclo[19.4.0.0³,⁸]pentacosa-1(21),3,5,7,22,24-hexaen-22-yl]phenyl]sulfonylacetamide

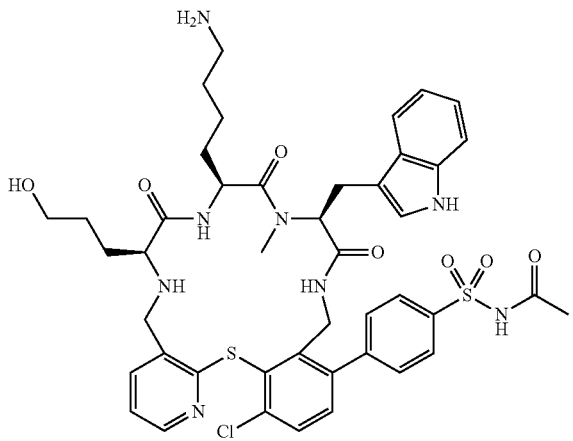 [SMILES: CC(=O)NS(=O)(=O)c1ccc(-c2ccc(Cl)c3c2CNC(=O)[C@H](Cc2c[nH]c4ccccc24)N(C)C(=O)[C@H](CCCCN)NC(=O)[C@H](CCCO)NCc2cccnc2S3)cc1]

The title compound was produced in analogy to example 1.04, replacing tert-butyl 3-(((7S,10S,13S)-17-bromo-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate by tert-butyl 3-(((7S,10S,13S)-17-bromo-10-(4-(((tert-butoxycarbonyl)amino)butyl)-20-chloro-7-(3-hydroxypropyl)-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate (intermediate 1.11). White lyophilised powder, MS: 903.4 $[M+H]^+$.

Example 16.01

(11S,14S,17S)-14-(4-Aminobutyl)-25-chloro-11-(3-hydroxypropyl)-22-(2-hydroxypyrimidin-5-yl)-17-(1H-indol-3-ylmethyl)-16-methyl-2-thia-4,10,13,16,19-pentazatricyclo[19.4.0.0³,⁸]pentacosa-1(21),3,5,7,22,24-hexaene-12,15,18-trione

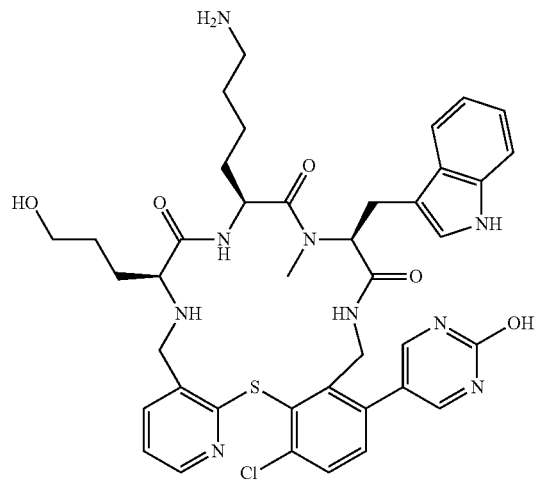 [SMILES: CN1C(=O)[C@H](CCCCN)NC(=O)[C@H](CCCO)NCc2cccnc2Sc2c(Cl)ccc(-c3cnc(O)nc3)c2CNC(=O)[C@@H]1Cc1c[nH]c2ccccc12]

The title compound was produced in analogy to example 16, replacing (4-(N-acetylsulfamoyl)phenyl)boronic acid by 5-(4,4,5,5-tetramethyl-1,3,2-dioxaborolan-2-yl)pyrimidin-2(1H)-one [CAS-RN 1073354-84-3]. Off-white lyophilised powder, MS: 800.6 $[M+H]^+$.

Example 17

N-[4-[(11S,14S,7S)-25-Chloro-14-[4-(2,2-difluoroethylamino)butyl]-11-(3-hydroxypropyl)-17-(1H-indol-3-ylmethyl)-16-methyl-12,15,18-trioxo-2-thia-4,10,13,16,19-pentazatricyclo[19.4.0.0³,⁸]pentacosa-1(21),3,5,7,22,24-hexaen-22-yl]phenyl]sulfonylacetamide

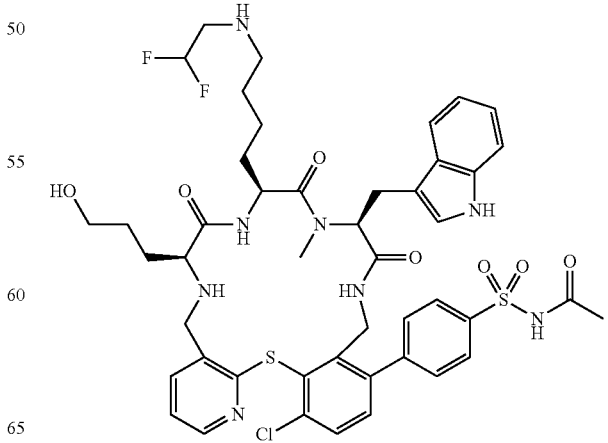

The title compound was produced in analogy to example 1.04, replacing tert-butyl 3-(((7S,10S,13S)-17-bromo-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate by tert-butyl 3-(((7S,10S,13S)-17-bromo-10-(4-((tert-butoxycarbonyl)(2,2-difluoroethyl)amino)butyl)-20-chloro-7-(3-hydroxypropyl)-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate (intermediate 1.12). Light yellow lyophilised powder, MS:967.6 [M+H]+.

Example 18

N-[4-[(11S,14S,17S)-25-Chloro-11-(3-hydroxypropyl)-17-(1H-indol-3-ylmethyl)-16-methyl-14-[4-(methylamino)butyl]-12,15,18-trioxo-2-thia-4,10,13,16,19-pentazatricyclo[19.4.0.03,8]pentacosa-1(21),3,5,7,22,24-hexaen-22-yl]phenyl]sulfonylacetamide

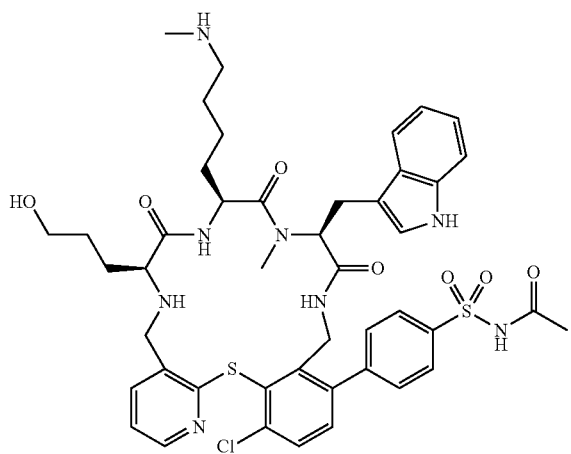 [SMILES: CNCCCC[C@@H]1NC(=O)[C@H](CCCO)NCc2cccnc2Sc2c(Cl)ccc(-c3ccc(S(=O)(=O)NC(C)=O)cc3)c2CNC(=O)[C@H](Cc2c[nH]c3ccccc23)N(C)C1=O]

The title compound was produced in analogy to example 1.04, replacing tert-butyl 3-(((7S,10S,13S)-17-bromo-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate by tert-butyl 3-(((7S,10S,13S)-17-bromo-10-(4-((tert-butoxycarbonyl)(methyl)amino)butyl)-7-(3-((tert-butyldimethylsilyl)oxy)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate (intermediate 1.13). White lyophilised powder, MS: 917.3 [M+H]+.

Example 19

(11S,14S,17S)-11-(3-Aminopropyl)-25-chloro-14-[4-(2,2-difluoroethylamino)butyl]-22-(2-hydroxypyrimidin-5-yl)-17-(1H-indol-3-ylmethyl)-16-methyl-2-thia-4,10,13,16,19-pentazatricyclo[19.4.0.03,8]pentacosa-1(21),3,5,7,22,24-hexaene-12,15,18-trione

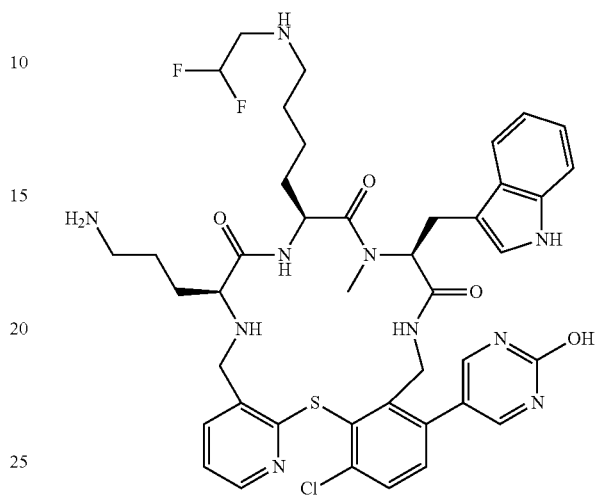

The title compound was produced in analogy to example 1.05, replacing tert-butyl 3-(((7S,10S,13S)-17-bromo-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate by tert-butyl 3-(((7S,10S,13S)-17-bromo-10-(4-((tert-butoxycarbonyl)(2,2-difluoroethyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate (intermediate 1.14). Off-white lyophilised powder, MS: 863.6 [M+H]+.

Example 20

3-[3-[(11S,14S,17S)-22-[4-(Acetylsulfamoyl)phenyl]-14-(4-aminobutyl)-25-chloro-17-(H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-11-yl]propylamino]propanoic acid

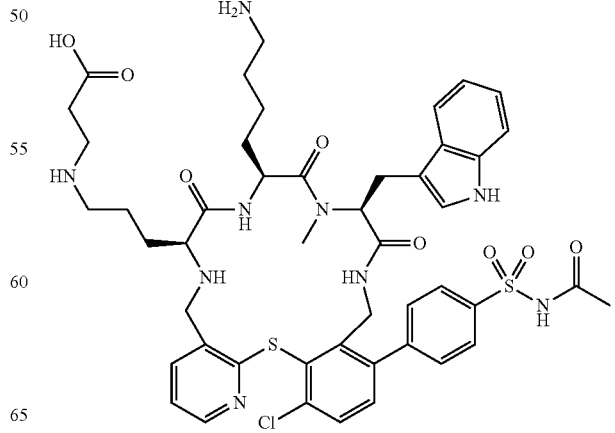

Step 1: tert-Butyl 3-((((7S,10S,13S)-17-(4-(N-acetylsulfamoyl)phenyl)-7-(3-((tert-butoxycarbonyl)(3-methoxy-3-oxopropyl)amino)propyl)-10-(4-((tert-butoxycarbonyl)amino)butyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate The title compound was produced in analogy to example 1, step 1 from tert-butyl 3-((((7S,10S,13S)-17-bromo-7-(3-((tert-butoxycarbonyl)(3-methoxy-3-oxopropyl)amino)propyl)-10-(4-((tert-butoxycarbonyl)amino)butyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate (intermediate 1.15) and (4-(N-acetylsulfamoyl)phenyl)boronic acid [CAS-RN 913835-52-6].

Step 2: 3-((3-(((7S,10S,13S)-17-(4-(N-Acetylsulfamoyl)phenyl)-13-((1-(tert-butoxycarbonyl)-1H-indol-3-yl)methyl)-10-(4-((tert-butoxycarbonyl)amino)butyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-7-yl)propyl)(tert-butoxycarbonyl)amino)propanoic acid To a solution of tert-butyl 3-((((7S,10S,13S)-17-(4-(N-acetylsulfamoyl)phenyl)-7-(3-((tert-butoxycarbonyl)(3-methoxy-3-oxopropyl)amino)propyl)-10-(4-((tert-butoxycarbonyl)amino)butyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate (120 mg, 93.1 μmol) in tetrahydrofuran (1 mL) was added 2 M aq lithium hydroxide solution (1 mL, 2 mmol). The reaction mixture was stirred at room temperature for 2 hours, then neutralized to pH 7 with 1 M aq. hydrochloric acid HCl solution. The mixture was extracted with ethyl acetate, the organic layer was washed with water, dried over sodium sulfate, filtered and concentrated. The residue was purified by preparative HPLC as described in example 1 to produce the title compound (60 mg, 51%) as a white lyophilised powder.

Step 3: 3-((3-(((7S,10S,13S)-13-((1H-indol-3-yl)methyl)-17-(4-(N-acetylsulfamoyl)phenyl)-10-(4-aminobutyl)-20-chloro-12-methyl-8,11,14-trioxo-5,6,7,8,9,10,11,12,13,14,15,16-dodecahydrobenzo[b]pyrido[3,2-p][1]thia[5,8,11,114]tetraazacycloheptadecin-7-yl)propyl)amino)propanoic acid The title compound was produced in analogy to example 1, step 2 from 3-((3-(((7S,10S,13S)-17-(4-(N-acetylsulfamoyl)phenyl)-13-((1-(tert-butoxycarbonyl)-1H-indol-3-yl)methyl)-10-(4-((tert-butoxycarbonyl)amino)butyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-7-yl)propyl)(tert-butoxycarbonyl)amino)propanoic acid. White lyophilised powder, MS: 974.4 [M+H]$^+$.

Example 21

(11S,14S,17S)-14-(4-Aminobutyl)-11-(3-aminopropyl)-25-chloro-17-(1H-indol-3-ylmethyl)-16-methyl-23-(1H-tetrazol-5-yl)-2-thia-4,10,13,16,19-pentazatricyclo[19.4.0.0³,⁸]pentacosa-1(21),3,5,7,22,24-hexaene-12,15,18-trione

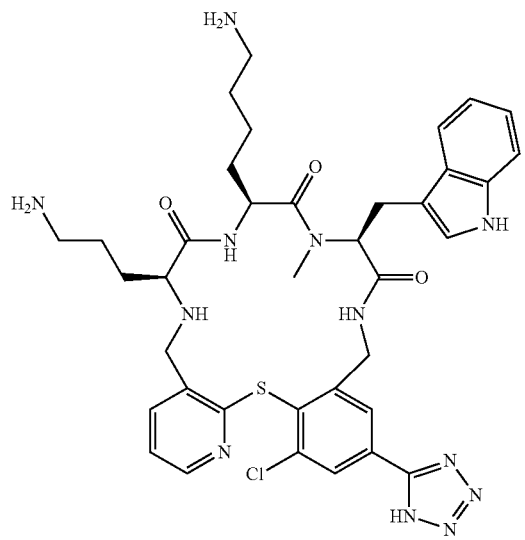 [SMILES: CN1C(=O)[C@H](CCCCN)NC(=O)[C@H](CCCN)NCc2cccnc2Sc2c(Cl)cc(-c3nnn[nH]3)cc2CNC(=O)[C@@H]1Cc1c[nH]c2ccccc12]

The title compound was produced in analogy to example 1, step 2 from tert-butyl 3-((((7S,10S,13S)-18-(2H-tetrazol-5-yl)-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate (intermediate 1.16). White lyophilised powder, MS: 773.4 [M+H]$^+$.

Example 22

(11S,14S,17S)-14-(4-Aminobutyl)-1-(3-aminopropyl)-25-chloro-17-(1H-indol-3-ylmethyl)-16-methyl-23-(1H-triazol-5-yl)-2-thia-4,10,13,16,19-pentazatricyclo[19.4.0.0³,⁸]pentacosa-1(21),3,5,7,22,24-hexaene-12,15,18-trione

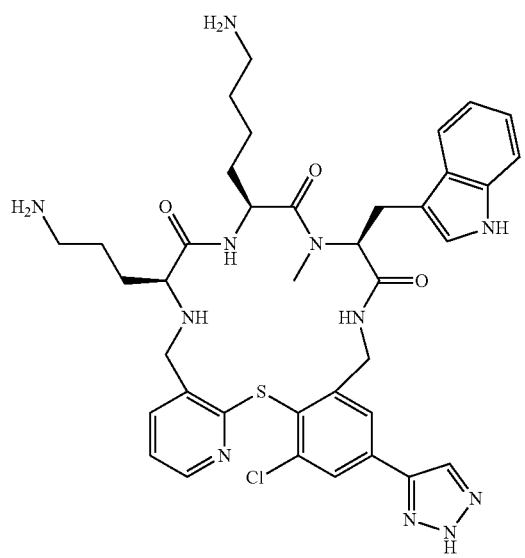 [SMILES: CN1C(=O)[C@H](CCCCN)NC(=O)[C@H](CCCN)NCc2cccnc2Sc2c(Cl)cc(-c3cn[nH]n3)cc2CNC(=O)[C@@H]1Cc1c[nH]c2ccccc12]

The title compound was produced in analogy to example 1, step 2 from tert-butyl 3-(((7S,10S,13S)-18-(2H-triazol-4-yl)-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate (intermediate 1.17). White lyophilised powder, MS: 772.2 [M+H]⁺.

INTERMEDIATES

General Procedure for Peptide Macrocycle Synthesis

1. Solid Phase Peptide Synthesis

The tripeptide sequence was synthesized manually via state-of-the-art solid phase synthesis protocols (Fmoc-chemistry) as referenced by e.g.: Kates and Albericio, Eds., "Solid Phase Synthesis: A practical guide", Marcel Dekker, New York, Basel, 2000.

As a solid support 2-chloro-tritylchloride resin (1.6 meq/g, 100-200 mesh) was used. This resin was loaded with 1-[(1,1-dimethylethoxy)carbonyl]-N-[(9H-fluoren-9-ylmethoxy)carbonyl]-N-methyl-L-tryptophan (CAS-RN 197632-75; 0.6 equivalents) and diisopropylethylamine (8 equivalents) in dry dichloromethane overnight at room temperature. After extensive washing with N,N-dimethylformamide and dichloromethane, the 9-fluorenylmethoxycarbonyl protective group was cleaved off with a mixture of 50% piperidine in dichlormethane/N,N-dimethylformamide (1:1) in N,N-dimethylformamide for 30 min at room temperature. After washing with N,N-dimethylformamide, dichloromethane and methanol the resin was dried under vacuum at room temperature overnight. The resin loading was determined via weight increase.

The second amino acid was coupled with 4 equivalents of 2-chloro-1-methylpyridinium iodide as coupling reagent, 6 equivalents of N,N-diisopropylethylamine in dichlormethane/N,N-dimethylformamide (1:1) overnight at room temperature. The resin was extensively washed with N,N-dimethylformamide and dichloromethane and the coupling rate was controlled by a test-cleavage.

The 9-fluorenylmethoxycarbonyl-group from the dipeptide was cleaved with a mixture of piperidine/dichloromethane/N,N-dimethylformamide (2:1:1) for maximally 5 min followed by washings with N,N-dimethylformamide and dichloromethane. The cleavage rates were again controlled by test-cleavage.

The third amino acid was coupled using 4 equivalents of O-(7-azabenzotriazol-1-yl)-N,N,N',N'-tetramethyluronium-hexafluorophosphate as coupling reagent and 6 equivalents diisopropylethylamine. Complete couplings were accomplished at room temperature for 2-4 hours with the coupling rate again controlled by a test-cleavage.

The 9-fluorenylmethoxycarbonyl-group from the tripeptide was cleaved with a mixture of 20% piperidine in N,N-dimethylformamide for 2×15-20 min at room temperature followed by washings with N,N-dimethylformamide and dichloromethane (test-cleavage).

2. Reductive Amination:

Resin with tripeptide was washed with dichloromethane, the corresponding tether dissolved in a mixture of 1-methyl-2-pyrrolidone/trimethyl orthoformate/acetic acid (49.7/49.7/0.6) and the solution was added to the resin. The mixture was shaken at room temperature for 30 min up to 3 h, then 10 equivalents of sodium cyanoborohydride were added and the reaction mixture was shaken at room temperature overnight. Finally, the resin was washed with N,N-dimethylformamide, dichloromethane, methanol/dichloromethane (1:1) and N,N-dimethylformamide.

The 9-fluorenylmethoxycarbonyl-group on the tether was cleaved with a mixture of 20% piperidine in N,N-dimethylformamide for 2× 15-20 min at room temperature followed by washings with N,N-dimethylformamide and dichloromethane (test-cleavage).

3. Cleavage:

A cleavage-cocktail of 20% hexafluoroisopropanol in dichloromethane was added to the resin and the mixture was stirred for 2 h at room temperature. The resin was filtered off and the solution was evaporated to dryness. The residue was dissolved in water/acetonitrile and lyophilized.

4. Cyclisation:

The obtained crude linear compound was cyclized by dissolving the powder in N,N-dimethylformamide. 1.2 equivalents of O-(7-azabenzotriazol-1-yl)-N,N,N',N'-tetramethyluronium-hexafluorophosphate and 5 equivalents diisopropylethylamine were added and the reaction mixture stirred at room temperature. Progress of the reaction was monitored by HPLC. After completion, the reaction mixture was diluted with ethyl acetate, washed with water and brine, dried over magnesium sulfate, filtered, and evaporated. The residue was chromatographed with silica gel using a heptane-ethyl acetate gradient as the eluent. yielding the crude product.

5. Purification:

The crude product was purified by reversed phase high-performance liquid chromatography (RP-HPLC) using a Phenomenex Gemini-NX 5u 110A column (100×30 mm) as the stationary phase and a gradient from water (+0.05% trifluoroacetic acid) to acetonitrile as the eluent. Fractions were collected and analyzed by LC/MS. Pure product samples were combined and lyophilized. Product identification was obtained via mass spectrometry.

Intermediate 1 tert-Butyl 3-{[(11S,14S,17S)-22-bromo-14-(4-{[(tert-butoxy)carbonyl]amino}butyl)-11-(3-{[(tert-butoxy)carbonyl]amino}propyl)-16-methyl-12,15,18-trioxo-2-thia-4,10,13,6,19-pentaazatricyclo[19.4.0.0ˆ{3,8}]pentacosa-1(25),3(8),4,6,21,23-hexaen-17-yl]methyl}-1H-indole-1-carboxylate

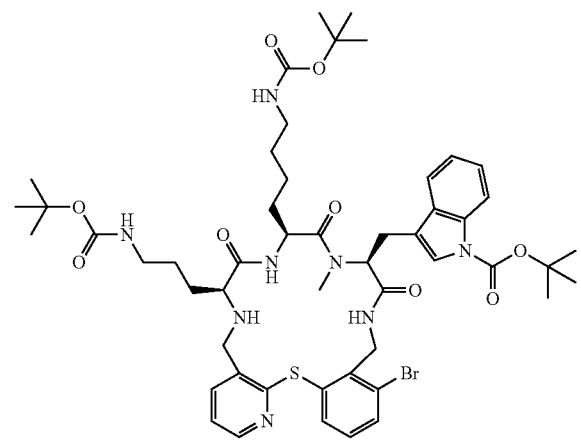

The title compound was produced according to the General procedure for Peptide Macrocycle Synthesis, using N⁶-[(1,1-dimethylethoxy)carbonyl]-N²-[(9H-fluoren-9-ylmethoxy)carbonyl]-L-lysine [CAS-RN 71989-26-9] as the second amino acid, N⁵-[(1,1-dimethylethoxy)carbonyl]-N²-[(9H-fluoren-9-ylmethoxy)carbonyl]-L-ornithine [CAS-RN 109425-55-0] as the third amino acid, and 9H-fluoren-9-ylmethyl N-[[2-bromo-6-[(3-formyl-2-pyridyl)sulfanyl]

phenyl]methyl]carbamate (intermediate 2) as the tether. White solid, MS: 1051.7 [M+H]⁺.

Intermediate 1.01 tert-Butyl 3-(((7S,10S,13S)-17-bromo-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrazino[2,3-p][1,5,8,11,14]thiatetraazacycloheptadecin-13-yl)methyl)-1H-indole-1-carboxylate

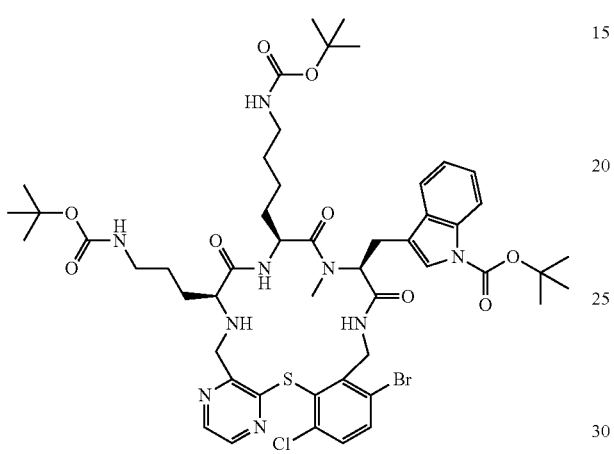

The title compound was produced in analogy to intermediate 1, replacing 9H-fluoren-9-ylmethyl N-[[2-bromo-6-[(3-formyl-2-pyridyl)sulfanyl]phenyl]methyl]carbamate by 9H-fluoren-9-ylmethyl N-[[6-bromo-3-chloro-2-(3-formylpyrazin-2-yl)sulfanyl-phenyl]methyl]carbamate (intermediate 3). Off-white solid, MS: 1084.6 [M+H]⁺.

Intermediate 1.02 tert-butyl 3-{[(11S,14S,17S)-22-bromo-11,14-bis(3-{[(tert-butoxy)carbonyl]amino}propyl)-25-fluoro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate

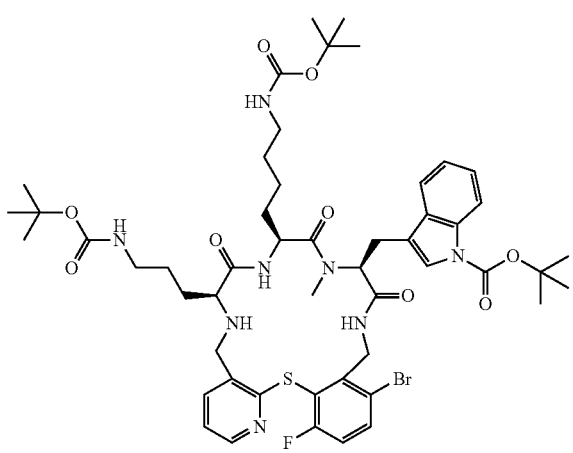 [SMILES: CN1C(=O)[C@H](CCCCNC(=O)OC(C)(C)C)NC(=O)[C@H](CCCNC(=O)OC(C)(C)C)NCc2cccnc2Sc2c(F)ccc(Br)c2CNC(=O)[C@@H]1Cc1cn(C(=O)OC(C)(C)C)c2ccccc12]

The title compound was produced in analogy to intermediate 1, replacing 9H-fluoren-9-ylmethyl N-[[2-bromo-6-[(3-formyl-2-pyridyl)sulfanyl]phenyl]methyl]carbamate by (9H-fluoren-9-yl)methyl 6-bromo-3-fluoro-2-((3-formylpyridin-2-yl)thio)benzylcarbamate (intermediate 2.01). White solid, MS: 1067.7 [M+H]⁺.

Intermediate 1.03 tert-Butyl 3-{[(1S,14S,17S)-22-bromo-11,14-bis(3-{[(tert-butoxy)carbonyl]amino}propyl)-25-chloro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate

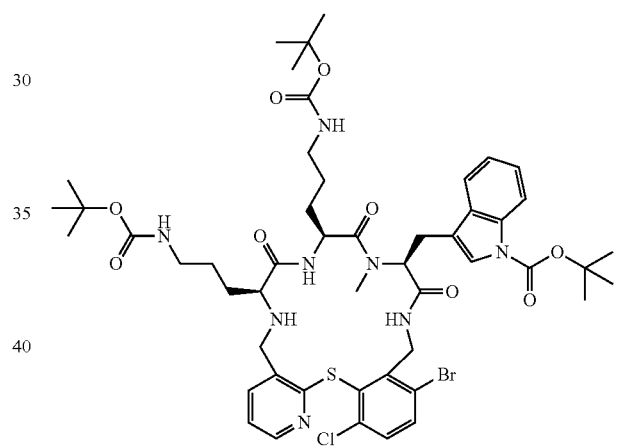

The title compound was produced according to the General procedure for Peptide Macrocycle Synthesis, using N⁵-[(1,1-dimethylethoxy)carbonyl]-N²-[(9H-fluoren-9-ylmethoxy)carbonyl]-L-ornithine [CAS-RN 109425-55-0] as the second amino acid, N⁵-[(1,1-Dimethylethoxy)carbonyl]-N²-[(9H-fluoren-9-ylmethoxy)carbonyl]-L-ornithine (CAS-RN 109425-55-0) as the third amino acid, and 9H-fluoren-9-ylmethyl N-[[6-bromo-3-chloro-2-[(3-formyl-2-pyridyl)sulfanyl]phenyl]methyl]carbamate [CAS-RN 2097290-48-5] as the tether.

White solid, MS: 1069.8 [M+H]⁺.

Intermediate 1.04 tert-Butyl 3-{[(11S,14S,17S)-22-bromo-11,14-bis(3-{[(tert-butoxy)carbonyl]amino}propyl)-25-fluoro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate

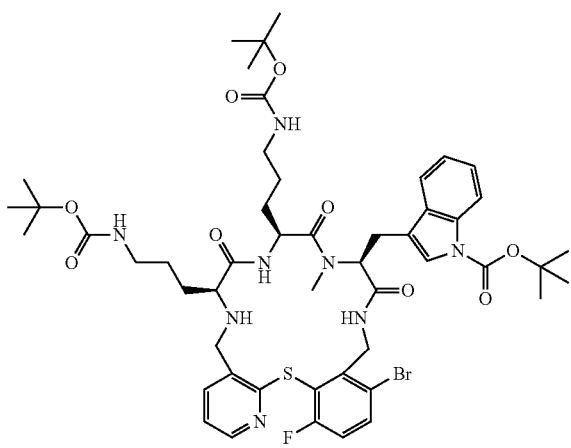 [SMILES: CN1C(=O)[C@H](CCCNC(=O)OC(C)(C)C)NC(=O)[C@H](CCCNC(=O)OC(C)(C)C)NCc2cccnc2Sc2c(F)ccc(Br)c2CNC(=O)[C@@H]1Cc1cn(C(=O)OC(C)(C)C)c2ccccc12]

The title compound was produced in analogy to intermediate 1.03, replacing 9H-fluoren-9-ylmethyl N-[[6-bromo-3-chloro-2-[(3-formyl-2-pyridyl)sulfanyl]phenyl]methyl]carbamate by (9H-fluoren-9-yl)methyl 6-bromo-3-fluoro-2-((3-formylpyridin-2-yl)thio)benzylcarbamate (intermediate 2.01). White solid, MS: 1053.7 [M+H]$^+$.

Intermediate 1.05 tert-Butyl 3-{[(11S,14S,17S)-22-bromo-14-(4-{[(tert-butoxy)carbonyl]amino}butyl)-25-chloro-16-methyl-12,15,18-trioxo-11-{2-[(triphenylmethyl)carbamoyl]ethyl}-2-thia-4,10,13,16,19-pentaazatricyclo[19.4.0.0^{3,8}]pentacosa-1(25),3(8),4,6,21,23-hexaen-17-yl]methyl}-1H-indole-1-carboxylate

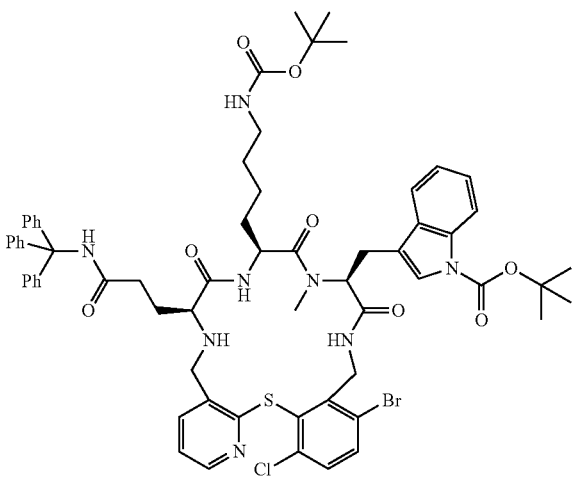 [SMILES: CN1C(=O)[C@H](CCCCNC(=O)OC(C)(C)C)NC(=O)[C@H](CCC(=O)NC(c2ccccc2)(c2ccccc2)c2ccccc2)NCc2cccnc2Sc2c(Cl)ccc(Br)c2CNC(=O)[C@@H]1Cc1cn(C(=O)OC(C)(C)C)c2ccccc12]

The title compound was produced according to the General procedure for Peptide Macrocycle Synthesis, using N$^6$-[(1,1-dimethylethoxy)carbonyl]-N$^2$-[(9H-fluoren-9-ylmethoxy)carbonyl]-L-lysine (CAS-RN 71989-26-9) as the second amino acid, N-(1,1-dimethylethyl)-N$^2$-[(9H-fluoren-9-ylmethoxy)carbonyl]-L-glutamine [CAS-RN 318996-13-3] as the third amino acid, and 9H-fluoren-9-ylmethyl N-[[6-bromo-3-chloro-2-[(3-formyl-2-pyridyl)sulfanyl]phenyl]methyl]carbamate [CAS-RN 2097290-48-5] as the tether. White solid, MS: 1239.9 [M+H]$^+$.

Intermediate 1.06 tert-butyl 3-(((7S,10S,13S)-17-bromo-1 O-(4-((tert-butoxycarbonyl)amino)butyl)-7-(3-((tert-butoxycarbonyl)amino)propyl)-12,20-dimethyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate

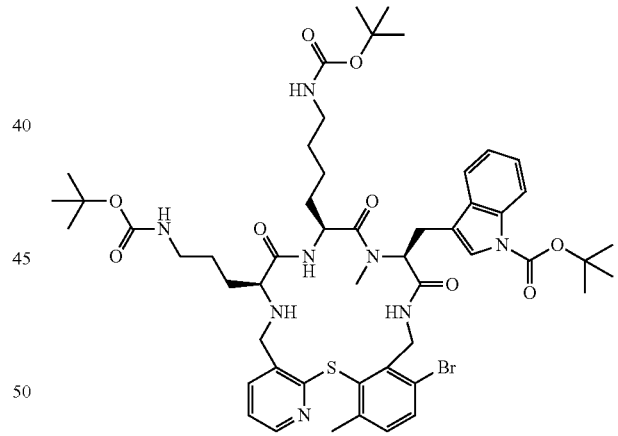

The title compound was produced in analogy to intermediate 1, replacing 9H-fluoren-9-ylmethyl N-[[2-bromo-6-[(3-formyl-2-pyridyl)sulfanyl]phenyl]methyl]carbamate by 9H-fluoren-9-ylmethyl N-[[6-bromo-2-[(3-formyl-2-pyridyl)sulfanyl]-3-methyl-phenyl]methyl]carbamate (intermediate 2.02). White solid, MS: 1063.6 [M+H]$^+$.

Intermediate 1.07 tert-Butyl 3-{[(11S,14S,17S)-22-bromo-14-(4-{[(tert-butoxy)carbonyl]amino}butyl)-1-(2-{[(tert-butoxy)carbonyl]amino}ethyl)-25-chloro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate

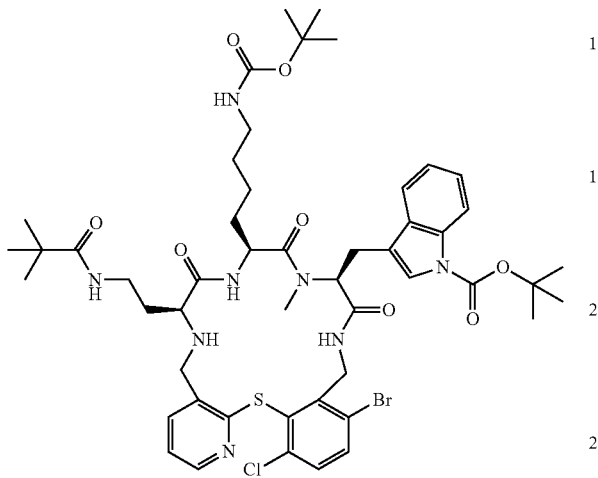

The title compound was produced according to the General procedure for Peptide Macrocycle Synthesis, using $N^6$-[(1,1-dimethylethoxy)carbonyl]-$N^2$-[(9H-fluoren-9-ylmethoxy)carbonyl]-L-lysine [CAS-RN 71989-26-9] as the second amino acid, (S)-4-[[(1,1-dimethylethoxy)carbonyl]amino]-2-[[(9H-fluoren-9-ylmethoxy)carbonyl]amino]-butanoic acid [CAS-RN 125238-99-5] as the third amino acid, and 9H-fluoren-9-ylmethyl N-[[6-bromo-3-chloro-2-[(3-formyl-2-pyridyl)sulfanyl]phenyl]methyl]carbamate [CAS-RN 2097290-48-5] as the tether. White solid, MS: 1069.8 [M+H]$^+$.

Intermediate 1.08 tert-Butyl 3-{[(11S,14S,17S)-22-bromo-11-(2-{[(tert-butoxy)carbonyl]amino}ethyl)-14-(3-{[(tert-butoxy)carbonyl]amino}propyl)-25-chloro-16-methyl-12,15,18-trioxo-2-thia-4,10,13,16,19-pentaazatricyclo[19.4.0.0^{3,8}]pentacosa-1(21), 3,5,7,22,24-hexaen-17-yl]methyl}-1H-indole-1-carboxylate

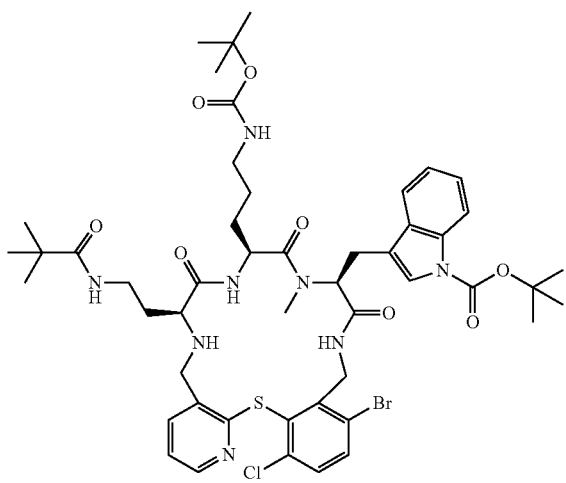 [SMILES: CN1C(=O)[C@H](CCCNC(=O)OC(C)(C)C)NC(=O)[C@H](CCNC(=O)C(C)(C)C)NCc2cccnc2Sc2c(Cl)ccc(Br)c2CNC(=O)[C@@H]1Cc1cn(C(=O)OC(C)(C)C)c2ccccc12]

The title compound was produced according to the General procedure for Peptide Macrocycle Synthesis, using $N^5$-[(1,1-dimethylethoxy)carbonyl]-$N^2$-[(9H-fluoren-9-ylmethoxy)carbonyl]-L-ornithine [CAS-RN 109425-55-0] as the second amino acid, (S)-4-[[(1,1-dimethylethoxy)carbonyl]amino]-2-[[(9H-fluoren-9-ylmethoxy)carbonyl]amino]-butanoic acid [CAS-RN 125238-99-5] as the third amino acid, and 9H-fluoren-9-ylmethyl N-[[6-bromo-3-chloro-2-[(3-formyl-2-pyridyl)sulfanyl]phenyl]methyl]carbamate [CAS-RN 2097290-48-5] as the tether. White solid, MS: 1055.8 [M+H]$^+$.

Intermediate 1.09 tert-Butyl 3-{[(11S,14S,17S)-22-bromo-14-(3-{[(tert-butoxy)carbonyl]amino}propyl)-25-chloro-11,16-dimethyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate

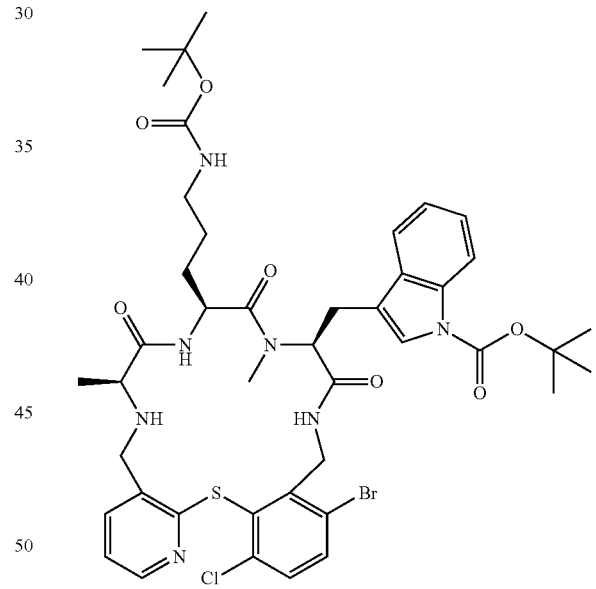

The title compound was produced according to the General procedure for Peptide Macrocycle Synthesis, using $N^5$-[(1,1-dimethylethoxy)carbonyl]-$N^2$-[(9H-fluoren-9-ylmethoxy)carbonyl]-L-ornithine [CAS-RN 109425-55-0] as the second amino acid, (9-fluorenylmethoxycarbonyl)-L-alanine [CAS 35661-39-3] as the third amino acid, and 9H-fluoren-9-ylmethyl N-[[6-bromo-3-chloro-2-[(3-formyl-2-pyridyl)sulfanyl]phenyl]methyl]carbamate [CAS-RN 2097290-48-5] as the tether. White solid, MS: 926.6 [M+H]$^+$.

Intermediate 1.10 tert-Butyl 3-{[(11S,14S,17S)-22-bromo-14-(4-{[(tert-butoxy)carbonyl]amino}butyl)-11-(3-{[(tert-butoxy)carbonyl]amino}propyl)-25-methoxy-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate

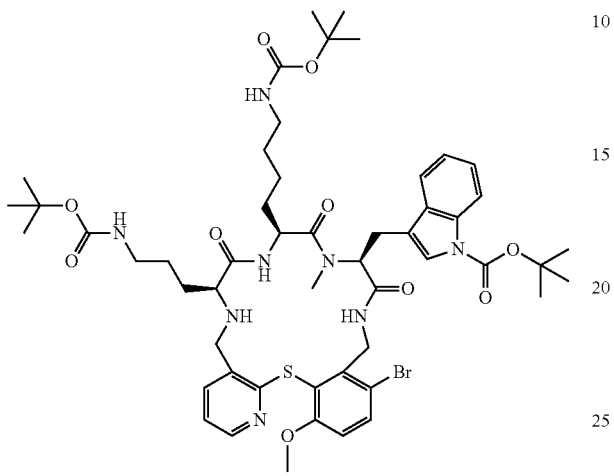

The title compound was produced in analogy to intermediate 1, replacing 9H-fluoren-9-ylmethyl N-[[2-bromo-6-[(3-formyl-2-pyridyl)sulfanyl]phenyl]methyl]carbamate by 9H-fluoren-9-ylmethyl N-[[6-bromo-2-[(3-formyl-2-pyridyl)sulfanyl]-3-methoxy-phenyl]methyl]carbamate (intermediate 2.03). Off-white solid, MS: 1079.8 [M+H]$^+$.

Intermediate 1.11 tert-butyl 3-(((7S,10S,13S)-17-bromo-10-(4-(((tert-butoxycarbonyl)amino)butyl)-20-chloro-7-(3-hydroxypropyl)-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate

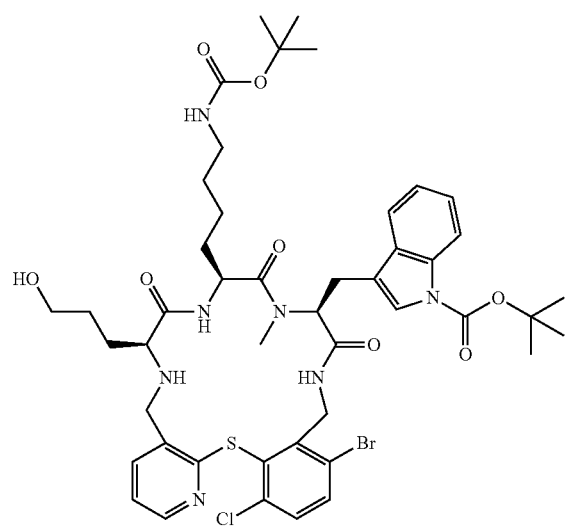 [SMILES: CN1C(=O)[C@H](CCCCNC(=O)OC(C)(C)C)NC(=O)[C@H](CCCO)NCc2cccnc2Sc2c(Cl)ccc(Br)c2CNC(=O)[C@@H]1Cc1cn(C(=O)OC(C)(C)C)c2ccccc12]

The title compound was produced according to the General procedure for Peptide Macrocycle Synthesis, using N$^6$-[(1,1-dimethylethoxy)carbonyl]-N$^2$-[(9H-fluoren-9-ylmethoxy)carbonyl]-L-lysine [CAS-RN 71989-26-9] as the second amino acid, 5-[[(1,1-dimethylethyl)dimethylsilyl]oxy]-N-[(9H-fluoren-9-ylmethoxy)carbonyl]-L-norvaline [CAS-RN 212388-38-0] as the third amino acid, and 9H-fluoren-9-ylmethyl N-[[6-bromo-3-chloro-2-[(3-formyl-2-pyridyl)sulfanyl]phenyl]methyl]carbamate [CAS-RN 2097290-48-5] as the tether. White solid, MS: 984.2 [M+H]$^+$.

Intermediate 1.12 tert-Butyl 3-(((7S,10S,13S)-17-bromo-10-(4-((tert-butoxycarbonyl) (2,2-difluoroethyl)amino)butyl)-20-chloro-7-(3-hydroxypropyl)-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate

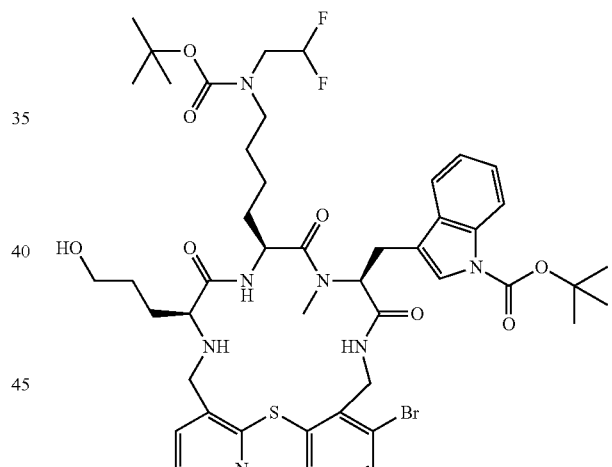

The title compound was produced according to the General procedure for Peptide Macrocycle Synthesis, using 6-[tert-butoxycarbonyl(2,2,2-trifluoroethyl)amino]-2-(9H-fluoren-9-ylmethoxycarbonylamino)hexanoic acid (intermediate 6) as the second amino acid, 5-[[(1,1-dimethylethyl)dimethylsilyl]oxy]-N-[(9H-fluoren-9-ylmethoxy)carbonyl]-L-norvaline [CAS-RN 212388-38-0] as the third amino acid, and 9H-fluoren-9-ylmethyl N-[[6-bromo-3-chloro-2-[(3-formyl-2-pyridyl)sulfanyl]phenyl]methyl]carbamate [CAS-RN 2097290-48-5] as the tether. White solid, MS: 1047.9 [M+H]$^+$.

Intermediate 1.13 tert-Butyl 3-(((7S,10S,13S)-17-bromo-10-(4-((tert-butoxycarbonyl)(methyl)amino)butyl)-7-(3-((tert-butyldimethylsilyl)oxy)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate

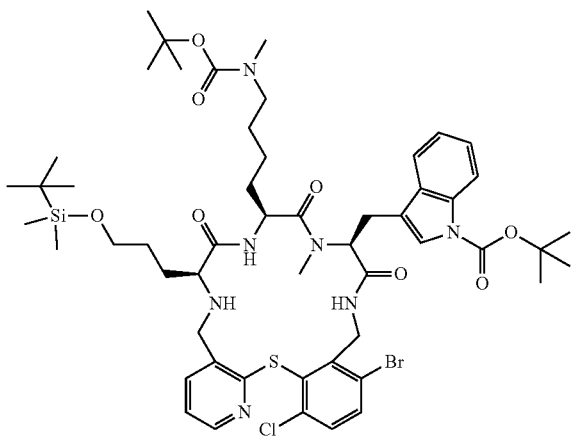 [SMILES: CN(CCCC[C@@H]1NC(=O)[C@H](CCCO[Si](C)(C)C(C)(C)C)NCc2cccnc2Sc2c(Cl)ccc(Br)c2CNC(=O)[C@H](Cc2cn(C(=O)OC(C)(C)C)c3ccccc23)N(C)C1=O)C(=O)OC(C)(C)C]

The title compound was produced according to the General procedure for Peptide Macrocycle Synthesis, using $N^6$-[(1,1-dimethylethoxy)carbonyl]-$N^2$-[(9H-fluoren-9-ylmethoxy)carbonyl]-$N^6$-methyl-L-lysine [CAS-RN 951695-85-5] as the second amino acid, 5-[[(1,1-dimethylethyl)dimethylsilyl]oxy]-N-[(9H-fluoren-9-ylmethoxy)carbonyl]-L-norvaline [CAS-RN 212388-38-0] as the third amino acid, and 9H-fluoren-9-ylmethyl N-[[6-bromo-3-chloro-2-[(3-formyl-2-pyridyl)sulfanyl]phenyl]methyl]carbamate [CAS-RN 2097290-48-5] as the tether. White powder, MS: 1112.1 [M+H]$^+$.

Intermediate 1.14 tert-Butyl 3-(((7S,10S,13S)-17-bromo-10-(4-((tert-butoxycarbonyl) (2,2-difluoroethyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate

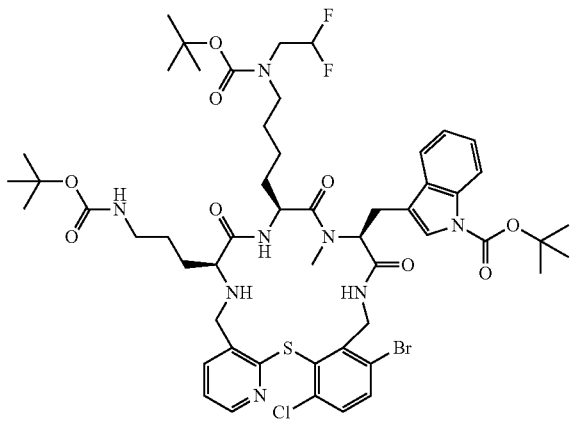 [SMILES: CN1C(=O)[C@H](CCCCN(CC(F)F)C(=O)OC(C)(C)C)NC(=O)[C@H](CCCNC(=O)OC(C)(C)C)NCc2cccnc2Sc2c(Cl)ccc(Br)c2CNC(=O)[C@@H]1Cc1cn(C(=O)OC(C)(C)C)c2ccccc12]

The title compound was produced according to the General procedure for Peptide Macrocycle Synthesis, using 6-[tert-butoxycarbonyl(2,2,2-trifluoroethyl)amino]-2-(9H-fluoren-9-ylmethoxycarbonylamino)hexanoic acid (intermediate 6) as the second amino acid, $N^5$-[(1,1-dimethylethoxy)carbonyl]-$N^2$-[(9H-fluoren-9-ylmethoxy)carbonyl]-L-ornithine [CAS-RN 109425-55-0] as the third amino acid, and 9H-fluoren-9-ylmethyl N-[[6-bromo-3-chloro-2-[(3-formyl-2-pyridyl)sulfanyl]phenyl]methyl]carbamate [CAS-RN 2097290-48-5] as the tether. White powder, MS: 1148.7 [M+H]$^+$.

Intermediate 1.15 tert-Butyl 3-(((7S,10S,13S)-17-bromo-7-(3-((tert-butoxycarbonyl) (3-methoxy-3-oxopropyl)amino)propyl)-10-(4-((tert-butoxycarbonyl)amino)butyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate

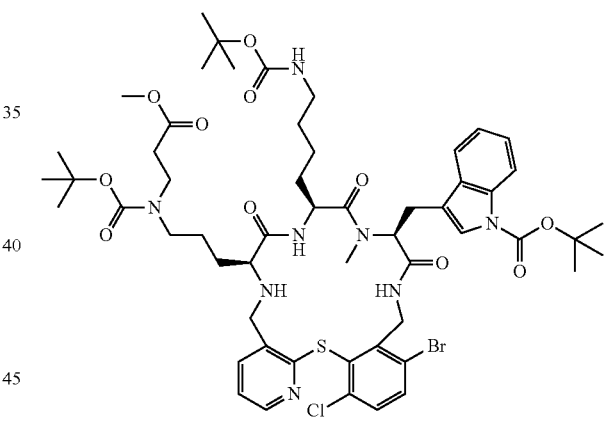

The title compound was produced according to the General procedure for Peptide Macrocycle Synthesis, using 6-[tert-butoxycarbonyl(2,2,2-trifluoroethyl)amino]-2-(9H-fluoren-9-ylmethoxycarbonylamino)hexanoic acid (intermediate 6) as the second amino acid, (S)-5-[tert-butoxycarbonyl-(3-methoxy-3-oxo-propyl)amino]-2-(9H-fluoren-9-ylmethoxycarbonylamino)pentanoic acid (intermediate 7) as the third amino acid, and 9H-fluoren-9-ylmethyl N-[[6-bromo-3-chloro-2-[(3-formyl-2-pyridyl)sulfanyl]phenyl]methyl]carbamate [CAS-RN 2097290-48-5] as the tether. White powder, MS: 1169.4 [M+H]$^+$.

Intermediate 1.16 tert-Butyl 3-(((7S,10S,13S)-18-(2H-tetrazol-5-yl)-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate

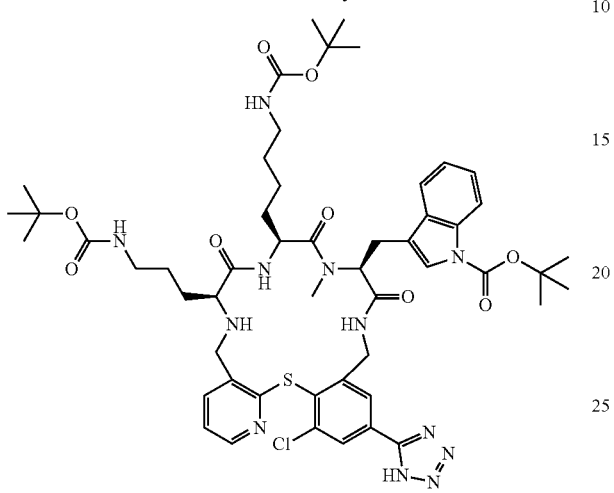

The title compound was produced in analogy to intermediate 1, replacing 9H-fluoren-9-ylmethyl N-[[2-bromo-6-[(3-formyl-2-pyridyl)sulfanyl]phenyl]methyl]carbamate 9H-fluoren-9-ylmethyl N-[[3-chloro-2-[(3-formyl-2-pyridyl)sulfanyl]-5-(2H-tetrazol-5-yl)phenyl]methyl]carbamate (intermediate 4). Off-white solid, MS: 1073.7 [M+H]$^+$.

Intermediate 1.17 tert-Butyl 3-(((7S,10S,13S)-18-(2H-triazol-4-yl)-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate

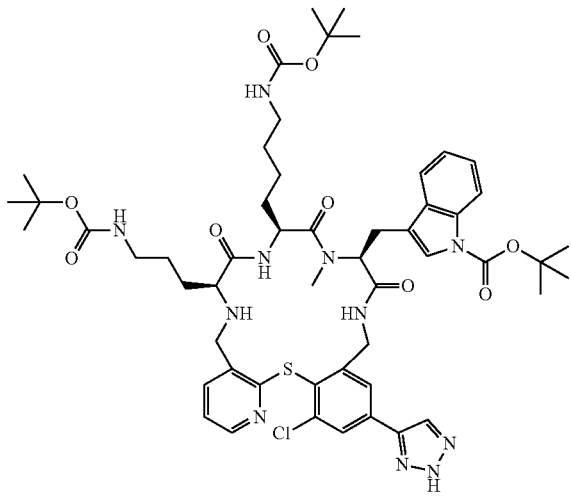 [SMILES: CN1C(=O)[C@H](CCCCNC(=O)OC(C)(C)C)NC(=O)[C@H](CCCNC(=O)OC(C)(C)C)NCc2cccnc2Sc2c(Cl)cc(-c3cn[nH]n3)cc2CNC(=O)[C@@H]1Cc1cn(C(=O)OC(C)(C)C)c2ccccc12]

The title compound was produced in analogy to intermediate 1, replacing 9H-fluoren-9-ylmethyl N-[[2-bromo-6-[(3-formyl-2-pyridyl)sulfanyl]phenyl]methyl]carbamate by 9H-fluoren-9-ylmethyl N-[[3-chloro-2-[(3-formyl-2-pyridyl)sulfanyl]-5-(2H-tetrazol-5-yl)phenyl]methyl] carbamat9H-fluoren-9-ylmethyl N-[[3-chloro-2-[(3-formyl-2-pyridyl)sulfanyl]-5-(2H-triazol-4-yl)phenyl]methyl] carbamate (intermediate 5). Off-white solid, MS: 1073.7 [M+H]$^+$.

Intermediate 2

9H-fluoren-9-ylmethyl N-[[2-bromo-6-[(3-formyl-2-pyridyl)sulfanyl]phenyl]methyl]carbamate

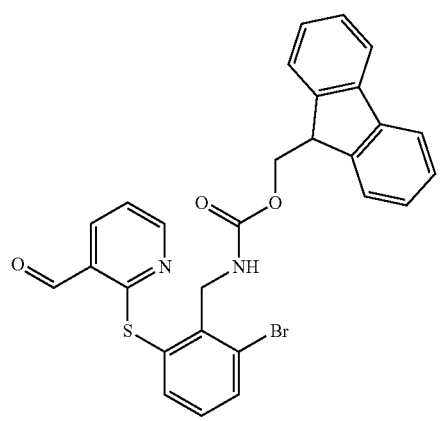 [SMILES: O=Cc1cccnc1Sc1cccc(Br)c1CNC(=O)OCC1c2ccccc2-c2ccccc21]

Step 1: Methyl 2-(3-bromo-2-formyl-phenyl)sulfanylpyridine-3-carboxylate

To a stirred solution of 2-bromo-6-fluorobenzaldehyde (37.0 g, 182 mmol) in N,N-dimethylformamide (370 mL) was added potassium tert-butylate (40.9 g, 365 mmol) and reaction mass was stirred at 25° C. for 30 min. Then, 2-mercaptonicotinic acid (CAS-RN38521-46-9; 31.1 g, 200 mmol) was added and reaction mixture was stirred at 80° C. for 4 h. After cooling to room temperature potassium carbonate (75.5 g, 547 mmol) was added followed by addition of iodomethane (77.6 g, 547 mmol), then after 16 h the reaction mixture was partitioned between ethyl acetate and water. The separated organic layer was washed with brine, dried over sodium sulfate, filtered, and evaporated under reduced pressure. Chromatography (silica gel; hexane/dichlormethane 85:15) produced the title compound (27.5 g, 43%). Yellow solid, MS: 351.9 [M+H]$^+$.

Step 2: Ethyl 2-[3-bromo-2-[(E)-tert-butylsulfinyliminomethyl]phenyl]sulfanylpyridine-3-carboxylate To a stirred solution of methyl 2-(3-bromo-2-formyl-phenyl)sulfanylpyridine-3-carboxylate (27.0 g, 76.7 mmol) in tetrahydrofuran (270 mL) was added 2-methyl-2-propanesulfinamide (CAS-RN 146374-27-8; 9.29 g, 76.7 mmol), titanium ethoxide (73.9 g, 384 mmol), and the reaction mixture was heated at 70° C. for 4 h. After cooling the reaction mixture was treated with brine, then insoluble material was removed by filtration through diatomaceous earth. The filtrate was extracted with ethyl acetate, the separated organic layer was washed with water, dried over sodium sulfate and evaporated under reduced pressure to afford the title compound (28.5 g, 79%) as yellow gum.

Step 3: N-[[2-Bromo-6-[[3-(hydroxymethyl)-2-pyridyl]sulfanyl]phenyl]methyl]-2-methyl-propane-2-sulfinamide To a stirred solution of ethyl 2-[3-bromo-2-[(E)-tert-butylsulfinyliminomethyl]phenyl]sulfanylpyridine-3-carboxylate (28.4 g, 60.5 mmol) in tetrahydrofuran (284 mL) was added lithium aluminumhydride solution (2.5 M in tetrahydrofuran, 48.4 mL, 121 mmol) at −40° C. and reaction mixture was stirred at −40° C. for 2 h, then excess reagent was destroyed by addition of saturated aq. sodium sulfate solution. The reaction mixture was extracted with ethyl acetate, the organic layer was washed with brine, dried over sodium sulfate, filtered, and evaporated to produce the title compound (22.6 g, 87%) as a yellow semisolid.

bamate (16.0 g, 29.2 mmol) in dichloromethane (160 mL) was added 1,1,1-tris(acetyloxy)-1,1-dihydro-1,2-benziodoxol-3(1H)-one (CAS-RN 87413-09-0; 18.6 g, 43.8 mmol) at 0° C., then the reaction mixture was allowed to reach room temperature over 1 h. The reaction mixture was partitioned between sat. aq. sodium hydrogencarbonate and dichloromethane. The organic layer was washed with water and brine, dried over sodium sulfate, filtered, and concentrated. Chromatographic (silica gel; dichloromethane/ethyl acetate 19:1) produced the title compound (11.9 g, 68% yield). Off-white solid, MS: 545.2 [M+H]$^+$.

The following intermediates were produced in analogy to intermediate 2, replacing 2-bromo-6-fluorobenzaldehyde by the appropriate aldehyde

| Ex. | Systematic Name | Aldehyde | MS (m/e) |
|---|---|---|---|
| 2.00 | 9H-fluoren-9-ylmethyl N-[[2-bromo-6-[(3-formyl-2-pyridyl)sulfanyl]phenyl]methyl]carbamate | 2-bromo-6-fluoro-5-methylbenzaldehyde | 545.2 [M + H]$^+$ |
| 2.01 | (9H-fluoren-9-yl)methyl 6-bromo-3-fluoro-2-((3-formylpyridin-2-yl)thio)benzylcarbamate | 5-bromo-2,3-difluorobenzaldehyde | 563.1 [M + H]$^+$ |
| 2.02 | 9H-fluoren-9-ylmethyl N-[[6-bromo-2-[(3-formyl-2-pyridyl)sulfanyl]-3-methyl-phenyl]methyl]carbamate | 6-bromo-2-fluoro-3-methylbenzaldehyde | 559.2 [M + H]$^+$ |
| 2.03 | 9H-fluoren-9-ylmethyl N-[[6-bromo-2-[(3-formyl-2-pyridyl)sulfanyl]-3-methoxy-phenyl]methyl]carbamate | 6-bromo-2-fluoro-3-methoxy-benzaldehyde | 575.1 [M + H]$^+$ |

Step 4: [2-[2-(Aminomethyl)-3-bromo-phenyl]sulfanyl-3-pyridyl]methanol hydrochloride To a stirred solution of N-[[2-bromo-6-[[3-(hydroxymethyl)-2-pyridyl]sulfanyl]phenyl]methyl]-2-methyl-propane-2-sulfinamide (58.0 g, 135 mmol) in tetrahydrofuran (550 mL) and methanol (10 mL) was added hydrogen chloride solution (4 M in 1,4-dioxane, 67.5 mL, 270 mmol) at room temperature, then after 2 h the reaction mixture was concentrated to produce the title compound (46.1 g, 94%) as an off-white solid.

Step 5: 9H-Fluoren-9-ylmethyl N-[[2-bromo-6-[[3-(hydroxymethyl)-2-pyridyl]sulfanyl]phenyl]methyl]carbamate To a stirred suspension of [2-[2-(aminomethyl)-3-bromo-phenyl]sulfanyl-3-pyridyl]methanol hydrochloride (46 g, 127 mmol) in 5% aq. sodium hydrogencarbonate solution (150 mL) was added (fluorenylmethoxycarbonyl)hydroxysuccinimide ester (CAS-RN 82911-69-1; 51.5 g, 153 mmol) in 1,4-dioxane (25 mL) at room temperature, then after 15 h the reaction mixture was partitioned between water and dichloromethane/methanol 9:1. The organic layer was washed with brine, dried over sodium sulfate, filtered, and evaporated. Chromatography (silica gel; dichloromethane/ethyl acetate 19:1) produced the title compound (34.3 g, 49% yield) as off-white solid.

Step 6: 9H-Fluoren-9-ylmethyl N-[[2-bromo-6-[(3-formyl-2-pyridyl)sulfanyl]phenyl]-methyl]carbamate To a solution of 9H-fluoren-9-ylmethyl N-[[2-bromo-6-[[3-(hydroxymethyl)-2-pyridyl]sulfanyl]phenyl]methyl]car- Intermediate 3

9H-fluoren-9-ylmethyl N-[[6-bromo-3-chloro-2-(3-formylpyrazin-2-yl)sulfanyl-phenyl]methyl]carbamate

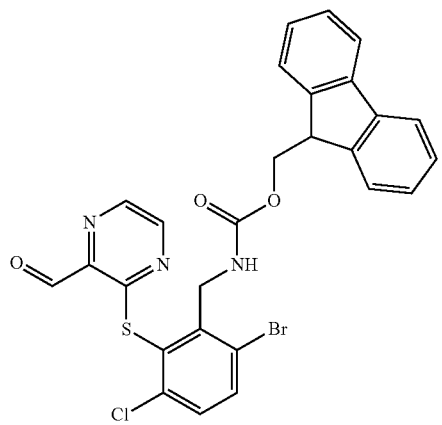 [SMILES: O=Cc1nccnc1Sc1c(Cl)ccc(Br)c1CNC(=O)OCC1c2ccccc2-c2ccccc21]

The title compound was produced in analogy to intermediate 2, replacing 2-bromo-6-fluorobenzaldehyde in step 1 by 6-bromo-3-chloro-2-fluorobenzaldehyde and 2-mercaptonicotinic acid in step 1 by 3,4-dihydro-3-thioxo-2-pyrazinecarboxylic acid [CAS-RN 36931-81-4]. White solid, MS: 580.0 [M+H]$^+$.

Intermediate 4

9H-Fluoren-9-ylmethyl N-[[3-chloro-2-[(3-formyl-2-pyridyl)sulfanyl]-5-(2H-tetrazol-5-yl)phenyl]methyl]carbamate

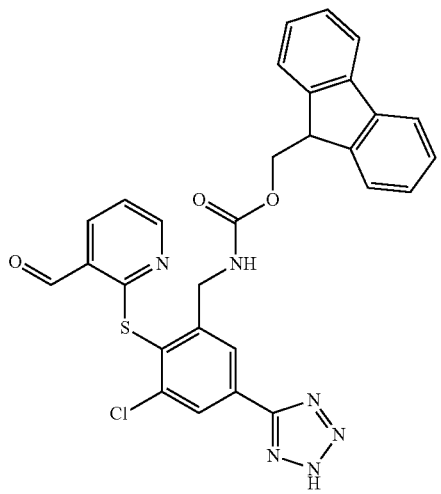 [SMILES: O=Cc1cccnc1Sc1c(Cl)cc(-c2nn[nH]n2)cc1CNC(=O)OCC1c2ccccc2-c2ccccc21]

Step 1: N-[[2-[[3-[[tert-Butyl(dimethyl)silyl]oxymethyl]-2-pyridyl]sulfanyl]-3-chloro-5-cyano-phenyl]methyl]-2-methyl-propane-2-sulfinamide To a stirred solution of N-[[5-bromo-2-[[3-[[tert-butyl(dimethyl)silyl]oxymethyl]-2-pyridyl]sulfanyl]-3-chloro-phenyl]methyl]-2-methyl-propane-2-sulfinamide (CAS-RN 2097290-65-6; 5.0 g, 8.65 mmol, 1 eq) in N,N-dimethylformamide (40 mL) was added zinc(II) cyanide (1.02 g, 8.65 mmol) and sparged with argon for 5 min. Then 4,5-bis(diphenylphosphino)-9,9-dimethylxanthene (CAS-RN 161265-03-8; 200 mg, 0.35 mmol) and tris(dibenzylideneacetone)dipalladium (CAS-RN 51364-51-3; 317 mg, 0.35 mmol, 0.040 eq) were added the reaction mixture was heated at 130° C. for 2 h. After cooling the reaction mixture was partitioned between water and ethyl acetate. The separated organic layer was washed with brine, dried over sodium sulfate, filtered, and evaporated. Chromatography (silica gel; hexane-ethyl acetate gradient) produced the title compound (3.6 g, 78%). Light brown gum, MS: 524.2 [M+H]$^+$.

Step 2: N-[[2-[[3-[[tert-Butyl(dimethyl)silyl]oxymethyl]-2-pyridyl]sulfanyl]-3-chloro-5-(1H-tetrazol-5-yl)phenyl]methyl]-2-methyl-propane-2-sulfinamide To the stirred solution of N-[[2-[[3-[[tert-butyl(dimethyl)silyl]oxymethyl]-2-pyridyl]sulfanyl]-3-chloro-5-cyano-phenyl]methyl]-2-methyl-propane-2-sulfinamide (3.6 g, 6.87 mmol) in 2-propanol (15 mL) and water (45 mL) was added zinc(II) bromide (1.55 g, 6.87 mmol) and sodium azide (670 mg, 10.3 mmol). The reaction mixture was heated at 100° C. for 12 h, then partitioned between water and ethyl acetate. The organic layer was washed with brine, dried over sodium sulfate, filtered, and evaporated to produce the title compound (3.6 g). Light brown solid, MS: 567.2 [M+H]$^+$.

Step 3: [2-[2-(Aminomethyl)-6-chloro-4-(1H-tetrazol-5-yl)phenyl]sulfanyl-3-pyridyl]methanol hydrochloride The title compound was produced in analogy to intermediate 2, step 4 from N-[[2-[[3-[[tert-butyl(dimethyl)silyl]oxymethyl]-2-pyridyl]sulfanyl]-3-chloro-5-(1H-tetrazol-5-yl)phenyl]methyl]-2-methyl-propane-2-sulfinamide. Off-white solid, MS: 349.1 [M+H]$^+$.

Step 4: 9H-Fluoren-9-ylmethyl N-[[3-chloro-2-[[3-(hydroxymethyl)-2-pyridyl]sulfanyl]-5-(1H-tetrazol-5-yl)phenyl]methyl]carbamate The title compound was produced in analogy to intermediate 2, step 5 from [2-[2-(aminomethyl)-6-chloro-4-(1H-tetrazol-5-yl)phenyl]sulfanyl-3-pyridyl]methanol. Light brown solid, MS: 571.1 [M+H]$^+$.

Step 5: 9H-Fluoren-9-ylmethyl N-[[3-chloro-2-[(3-formyl-2-pyridyl)sulfanyl]-5-(1H-tetrazol-5-yl)phenyl]methyl]carbamate The title compound was produced in analogy to intermediate 2, step 6 from 9H-fluoren-9-ylmethyl N-[[3-chloro-2-[[3-(hydroxymethyl)-2-pyridyl]sulfanyl]-5-(1H-tetrazol-5-yl)phenyl]methyl]carbamate. Light brown solid, MS: 569.2 [M+H]$^+$.

Intermediate 5

9H-Fluoren-9-ylmethyl N-[[3-chloro-2-[(3-formyl-2-pyridyl)sulfanyl]-5-(2H-triazol-4-yl)phenyl]methyl]carbamate

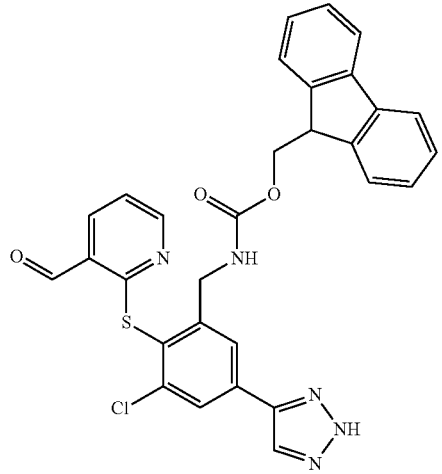 [SMILES: O=Cc1cccnc1Sc1c(Cl)cc(-c2cn[nH]n2)cc1CNC(=O)OCC1c2ccccc2-c2ccccc21]

Step 1: N-[[2-[[3-[[tert-Butyl(dimethyl)silyl]oxymethyl]-2-pyridyl]sulfanyl]-3-chloro-5-(2-trimethylsilylethynyl)phenyl]methyl]-2-methyl-propane-2-sulfinamide To a stirred and degassed suspension of N-[[5-bromo-2-[[3-[[tert-butyl(dimethyl)silyl]oxymethyl]-2-pyridyl]sulfanyl]-3-chloro-phenyl]methyl]-2-methyl-propane-2-sulfinamide (CAS-RN 2097290-65-6; 10.0 g, 17.3 mmol) and trimethylsilylacetylene (3.33 g, 34.6 mmol) in triethylamine (100 mL) were added copper(I) iodide (66 mg, 0.35 mmol), palladium(II) acetate (39 mg, 0.17 mmol), triphenylphosphine (91 mg, 0.35 mmol). The reaction mixture was heated at 80° C. for 6 h, then evaporated, and the residue was purified by chromatography (silica gel; hexane-ethyl acetate gradient) to produce the title compound (8.0 g, 76%). Light brown gum, MS: 595.0 [M+H]⁺.

Step 2: N-[[2-[[3-[[tert-Butyl(dimethyl)silyl]oxymethyl]-2-pyridyl]sulfanyl]-3-chloro-5-ethynyl-phenyl]methyl]-2-methyl-propane-2-sulfinamide To a stirred solution of N-[[2-[[3-[[tert-butyl(dimethyl) silyl]oxymethyl]-2-pyridyl]sulfanyl]-3-chloro-5-(2-trimethylsilylethynyl)phenyl]methyl]-2-methyl-propane-2-sulfinamide (8.0 g, 13.4 mmol) methanol (40 mL) and dichloromethane (40 mL) was added potassium carbonate (2.79 g, 20.2 mmol). The reaction mixture was stirred at room temperature for 16 h, then partitioned between water and dichlormethane. The organic layer was washed with brine, dried over sodium sulfate, filtered, and evaporated to produce the title compound (6.5 g). Grey solid, MS: 523.1 [M+H]⁺.

Step 3: N-[[2-[[3-[[tert-Butyl(dimethyl)silyl]oxymethyl]-2-pyridyl]sulfanyl]-3-chloro-5-(2H-triazol-4-yl)phenyl]methyl]-2-methyl-propane-2-sulfinamide To a stirred solution of N-[[2-[[3-[[tert-butyl(dimethyl) silyl]oxymethyl]-2-pyridyl]sulfanyl]-3-chloro-5-ethynyl-phenyl]methyl]-2-methyl-propane-2-sulfinamide (6.5 g, 12.4 mmol) in N,N-dimethylformamide (60 mL) was added sodium azide (8.08 g, 124 mmol). The reaction mixture was heated at 90° C. for 8 h, then partitioned between ethyl acetate and water. The organic layer was washed with brine, dried over sodium sulfate, filtered, and evaporated. Chromatography (silica gel; hexane-ethyl acetate gradient) produced the title compound (1.95 g, 28%). Light yellow solid, MS: 566.1 [M+H]⁺.

Step 4: [2-[2-(Aminomethyl)-6-chloro-4-(2H-triazol-4-yl)phenyl]sulfanyl-3-pyridyl]methanol hydrochloride The title compound was produced in analogy to intermediate 2, step 4 from N-[[2-[[3-[[tert-butyl(dimethyl)silyl] oxymethyl]-2-pyridyl]sulfanyl]-3-chloro-5-(2H-triazol-4-yl)phenyl]methyl]-2-methyl-propane-2-sulfinamide. Off white solid, MS: 348.1 [M+H]+.

Step 5: 9H-Fluoren-9-ylmethyl N-[[3-chloro-2-[[3-(hydroxymethyl)-2-pyridyl]sulfanyl]-5-(2H-triazol-4-yl)phenyl]methyl]carbamate The title compound was produced in analogy to intermediate 2, step 5 from [2-[2-(aminomethyl)-6-chloro-4-(2H-triazol-4-yl)phenyl]sulfanyl-3-pyridyl]methanol hydrochloride. Off-white solid, MS: 570.3 [M+H]⁺.

Step 6: 9H-Fluoren-9-ylmethyl N-[[3-chloro-2-[(3-formyl-2-pyridyl)sulfanyl]-5-(2H-triazol-4-yl)phenyl]methyl]carbamate The title compound was produced in analogy to intermediate 2, step 6 from 9H-fluoren-9-ylmethyl N-[[3-chloro-2-[[3-(hydroxymethyl)-2-pyridyl]sulfanyl]-5-(2H-triazol-4-yl)phenyl]methyl]carbamate. Off-white solid, MS: 568.0 [M+H]⁺.

Intermediate 6

6-[tert-Butoxycarbonyl(2,2,2-trifluoroethyl)amino]-2-(9H-fluoren-9-ylmethoxycarbonylamino)hexanoic acid

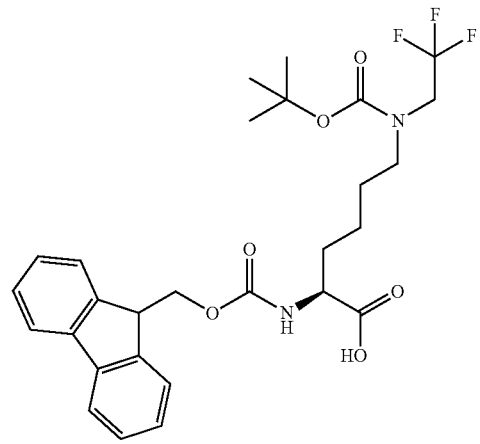 [SMILES: CC(C)(C)OC(=O)N(CCCC[C@H](NC(=O)OCC1c2ccccc2-c2ccccc21)C(=O)O)CC(F)(F)F]

Step 1: (S)-2,2,2-Trifluoroethyl 2-((((9H-fluoren-9-yl)methoxy)carbonyl)amino)-6-((2,2,2-trifluoroethyl)amino)hexanoate A suspension of N²-[(9H-fluoren-9-ylmethoxy)carbonyl]-L-lysine, hydrochloride (CAS-RN 139262-23-0; 4.05 g, 10 mmol, Eq: 1), 2,2,2-trifluoroethyl trifluoromethanesulfonate (23.2 g, 100 mmol) and sodium hydrogencarbonate (4.2 g, 50 mmol) in 2-Propanol (100 ml) was heated at 85° C. for 20 hours, then the solvent was removed in vacuo. The residue was acidified to pH 2 with 1 M aq. hydrochloric acid solution and extracted with ethyl acetate. The organic layer was dried over sodium sulfate, filtered, and evaporated to produce the title compound (5.0 g) as a colourless oil, which was used directly in the next step.

Step 2: (S)-2,2,2-Trifluoroethyl 2-((((9H-fluoren-9-yl)methoxy)carbonyl)amino)-6-((tert-butoxycarbonyl)(2,2,2-trifluoroethyl)amino)hexanoate A solution of (S)-2,2,2-trifluoroethyl 2-((((9H-fluoren-9-yl)methoxy)carbonyl)amino)-6-((2,2,2-trifluoroethyl) amino)hexanoate (5 g, 5.63 mmol), di-tert-butyl dicarbonate (3.69 g, 16.9 mmol), 4-(dimethylamino)pyridine (68.8 mg, 563 μmol) and diisopropylethylamine (3.64 g, 28.2 mmol) were combined in dichloromethane (50 mL) was stirred at room temperature for 3 h, then partitioned between 1 M aq. hydrochloric acid solution and ethyl acetate. The organic layer was concentrated under vacuum and the residue was purified by chromatography (silica gel, 80 g, hexane-ethyl acetate gradient) to produce the title compound (3.0 g, 76%) as a colourless oil.

Step 3: 6-[tert-butoxycarbonyl(2,2,2-trifluoroethyl) amino]-2-(9H-fluoren-9-ylmethoxycarbonylamino) hexanoic acid To a solution of (S)-2,2,2-trifluoroethyl 2-((((9H-fluoren-9-yl)methoxy)carbonyl)amino)-6-((tert-butoxycarbonyl)(2, 2,2-trifluoroethyl)amino)hexanoate (3.0 g, 4.74 mmol) in tetrahydrofuran (20 mL) was added calcium chloride solution (1 M in 2-propanol/water 2:1 80 ml, 80 mmol), followed by adding a solution of sodium hydroxide (948 mg, 23.7 mmol) in water (10 mL). The reaction mixture was stirred at room temperature for 2 hours, then acidified to pH 5 by addition of 1 M aq. hydrochloric acid solution and extracted with ethyl acetate. The organic layer was dried over sodium sulfate, filtered, and evaporated to produce the title compound (2.5 g, 86%). Off-white solid, MS: 573.0 [M+Na]$^+$.

Intermediate 7

(S)-5-[tert-Butoxycarbonyl-(3-methoxy-3-oxo-propyl)amino]-2-(9H-fluoren-9-ylmethoxycarbonylamino)pentanoic acid

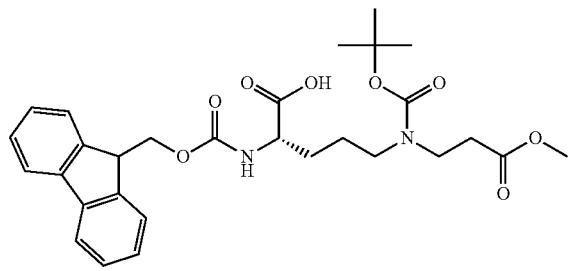 [SMILES: COC(=O)CCN(CCC[C@H](NC(=O)OCC1c2ccccc2-c2ccccc21)C(=O)O)C(=O)OC(C)(C)C]

To a mixture of 2,2,2-trifluoroacetic acid (6 mL) and water (6 mL) was added a solution of methyl 3,3-dimethoxypropanoate (3.14 g, 21.2 mmol) in dichloromethane (6 mL). The reaction mixture was stirred at room temperature overnight, then partitioned between dichloromethane and water. The organic layer was dried over sodium sulfate and filtered—To the filtrate was added N$^2$-[(9H-fluoren-9-ylmethoxy)carbonyl]-L-ornithine hydrochloride (CAS-RN 201046; 1.17 g, 3.00 mmol) and diisopropylethylamine (582 mg, 4.50 mmol), methanol (50 mL), and molecular sieves (4 Å) at room temperature, then after 10 min sodium cyanoborohydride (377 mg, 6.00 mmol) was added and the reaction mixture was stirred at 35° C. for 3 h, then cooled to room temperature and treated with water (30 mL), sodium carbonate (954 mg, 9.00 mmol) and di-tert-butyl dicarbonate (1.31 g, 6.00 mmol). The reaction mixture was stirred at room temperature overnight, then extracted with dichloromethane. The organic layer was dried over sodium sulfate, filtered and evaporated. The residue was purified by chromatography (heptane-ethyl acetate/methanol (9:1) gradient to produce the title compound (811 mg, 50%). White solid, MS: 563.2 [M+Na]$^+$.

Example 23

Antimicrobial Susceptibility Testing: 50% Growth Inhibitory Concentration (IC50) Determination The in vitro antimicrobial activity of the compounds was alternatively determined according to the following procedure:

The assay used a 10-points Iso-Sensitest broth medium to measure quantitatively the in vitro activity of the compounds against *A. baumannii* ATCC 17978.

Stock compounds in DMSO were serially twofold diluted (e.g. range from 10 to 0.02 μM final concentration) in 384 wells microtiter plates and inoculated with 49 μl the bacterial suspension in Iso-Sensitest medium to have a final cell concentration of ~5×10$^{(5)}$ CFU/ml in a final volume/well of 50 Microtiter plates were incubated at 35±2° C.

Bacterial cell growth was determined by the measurement of optical density at λ=600 nm each 20 minutes over a time course of 16 h.

Growth inhibition was calculated during the logarithmic growth of the bacterial cells by determination of the concentration inhibiting 50% (IC50) and 90% (IC90) of the growth.

Table 1 provides the 50% growth inhibitory concentrations (IC50) in micromoles per liter of the compounds of present invention obtained against the *A. baumannnii* strain ATCC17978.

Particular compounds of the present invention exhibit an IC50 (ATCC17978)≤10 μmol/l.

More particular compounds of the present invention exhibit an IC50 (ATCC17978)≤1 μmol/l.

Most particular compounds of the present invention exhibit an IC50 (ATCC17978)≤0.5 μmol/l.

TABLE 1

50% growth inhibition concentrations (IC50) in micromoles per liter of the compounds of present invention obtained against *A. baumannii* strain ATCC17978.

| Example | IC50 ATCC17978 [μmol/l] |
|---|---|
| 1.00 | 0.02 |
| 1.01 | 0.02 |
| 1.02 | 0.10 |
| 1.03 | 0.36 |
| 1.04 | 0.02 |
| 1.05 | 0.02 |
| 2.00 | 0.08 |
| 3.00 | 0.08 |
| 4.00 | 0.02 |
| 5.00 | 0.02 |
| 6.00 | 0.02 |
| 7.00 | 0.02 |
| 7.01 | 0.02 |
| 7.02 | 0.03 |
| 7.03 | 0.04 |
| 8.00 | 0.02 |
| 8.01 | 0.02 |
| 8.02 | 0.08 |
| 9.00 | 0.02 |
| 9.01 | 0.02 |
| 10.00 | 0.62 |
| 10.01 | 3.03 |
| 10.02 | 0.15 |
| 11.00 | 0.02 |
| 11.01 | 0.02 |
| 12.00 | 0.02 |
| 13.00 | 0.02 |
| 14.00 | 0.72 |
| 15.00 | 0.08 |
| 15.01 | 0.04 |
| 16.00 | 0.31 |
| 16.01 | 1.84 |
| 17.00 | 5.22 |
| 18.00 | 0.63 |
| 19.00 | 0.30 |
| 20.00 | 0.52 |
| 21.00 | 10.04 |
| 22.00 | 0.18 |

The invention claimed is:
1. A compound of formula (I):

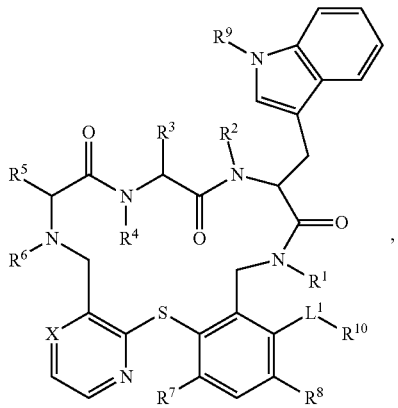

or a pharmaceutically acceptable salt thereof, wherein:
X is C-$L^2$-$R^{11}$ or N;
$R^1$, $R^2$, $R^4$, $R^6$ and $R^9$ are each individually selected from hydrogen and $C_{1-7}$-alkyl;
$R^3$ and $R^5$ are each independently selected from $C_{1-7}$-alkyl, hydroxy-$C_{1-7}$-alkyl, —$(CH_2)_m$—$NR^{20}R^{21}$ and —$(CH_2)_n$—$C(O)$—$NR^{22}R^{23}$;
$R^7$, $R^8$, $R^{10}$ and $R^{11}$ are each individually selected from hydrogen, halogen, $C_{1-7}$-alkyl, $C_{1-7}$-alkoxy and a carboxylic acid bioisostere, wherein at least one of $R^7$, $R^8$, $R^{10}$ and $R^{11}$ is a carboxylic acid bioisostere;
$R^{20}$, $R^{21}$, $R^{22}$ and $R^{23}$ are each individually selected from hydrogen, $C_{1-7}$-alkyl, $C_{1-7}$-haloalkyl and carboxy-$C_{1-7}$-alkyl;
$L^1$ and $L^2$ are each individually selected from a covalent bond, a group

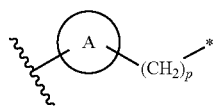

and a group

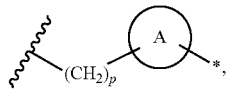

wherein:
A is selected from aryl, heteroaryl, cycloalkyl and heterocycloalkyl;
p is 0, 1, 2, 3, or 4;
the wavy line indicates the point of attachment of $L^1$ to the rest of formula (I) or of $L^2$ to "C" in "C-$L^2$-$R^{11}$"; and
* indicates the point of attachment of $L^1$ to $R^{10}$ or of $L^2$ to $R^{11}$;
m and n are each independently an integer selected from 1, 2, 3, and 4; and
each carboxylic acid bioisostere is individually selected from 3H-benzotriazol-5-yl, methylsulfonylcarbamoyl, acetylsulfamoyl, 1H-tetrazol-5-yl, 2-oxo-1H-pyrimidin-5-yl, 5-oxo-4H-1,2,4-thiadiazol-3-yl, 5-oxo-4H-1,2,4-oxadiazol-3-yl, —$S(O)_2$—OH, —$P(O)(OH)_2$ and 2-hydroxypyrimidin-5-yl.

2. The compound of formula (I) according to claim 1, or a pharmaceutically acceptable salt thereof, wherein X is C-$L^2$-$R^{11}$ or N, wherein:
$L^2$ is a covalent bond; and
$R^{11}$ is hydrogen.

3. The compound of formula (I) according to claim 1, or a pharmaceutically acceptable salt thereof, wherein X is C-$L^2$-$R^{11}$, wherein:
$L^2$ is a covalent bond; and
$R^{11}$ is hydrogen.

4. The compound of formula (I) according to claim 1, or a pharmaceutically acceptable salt thereof, wherein $R^1$ is hydrogen.

5. The compound of formula (I) according to claim 1, or a pharmaceutically acceptable salt thereof, wherein $R^2$ is $C_{1-7}$-alkyl.

6. The compound of formula (I) according to claim 1, or a pharmaceutically acceptable salt thereof, wherein $R^2$ is methyl.

7. The compound of formula (I) according to claim 1, or a pharmaceutically acceptable salt thereof, wherein $R^3$ is —$(CH_2)_m$—$NR^{20}R^{21}$, wherein:
$R^{20}$ is selected from hydrogen, $C_{1-7}$-alkyl and $C_{1-7}$-haloalkyl;
$R^{21}$ is hydrogen; and
m is 3 or 4.

8. The compound of formula (I) according to claim 1, or a pharmaceutically acceptable salt thereof, wherein $R^3$ is —$(CH_2)_m$—$NR^{20}R^{21}$, wherein:
$R^{20}$ and $R^{21}$ are both hydrogen; and
m is 3 or 4.

9. The compound of formula (I) according to claim 1, or a pharmaceutically acceptable salt thereof, wherein $R^4$ is hydrogen.

10. The compound of formula (I) according to claim 1, or a pharmaceutically acceptable salt thereof, wherein $R^5$ is selected from $C_{1-7}$-alkyl, hydroxy-$C_{1-7}$-alkyl, —$(CH_2)_m$—$NR^{20}R^{21}$ and —$(CH_2)_n$—$C(O)$—$NR^{22}R^{23}$, wherein:
$R^{20}$ is hydrogen or carboxy-$C_{1-7}$-alkyl;
each of $R^{21}$, $R^{22}$ and $R^{23}$ is hydrogen;
m is 2 or 3; and
n is 2.

11. The compound of formula (I) according to claim 1, or a pharmaceutically acceptable salt thereof, wherein $R^5$ is —$(CH_2)_m$—$NR^{20}R^{21}$, wherein:
$R^{20}$ and $R^{21}$ are both hydrogen; and
m is 2 or 3.

12. The compound of formula (I) according to claim 1, or a pharmaceutically acceptable salt thereof, wherein $R^6$ is hydrogen.

13. The compound of formula (I) according to claim 1, or a pharmaceutically acceptable salt thereof, wherein $R^7$ is selected from hydrogen, halogen, $C_{1-7}$-alkyl and $C_{1-7}$-alkoxy.

14. The compound of formula (I) according to claim 1, or a pharmaceutically acceptable salt thereof, wherein $R^8$ is selected from hydrogen and a carboxylic acid bioisostere.

15. The compound of formula (I) according to claim 1, or a pharmaceutically acceptable salt thereof, wherein $R^9$ is hydrogen.

16. The compound of formula (I) according to claim 1, or a pharmaceutically acceptable salt thereof, wherein $R^{10}$ is hydrogen or a carboxylic acid bioisostere.

17. The compound of formula (I) according to claim 1, or a pharmaceutically acceptable salt thereof, wherein $L^1$ is a covalent bond or a group

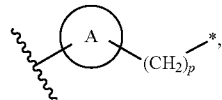

A is aryl or heterocycloalkyl;
p is 0 or 1;
the wavy line indicates the point of attachment of $L^1$ to the rest of formula (I); and
* indicates the point of attachment of $L^1$ to $R^{10}$.

18. The compound of formula (I) according to claim 1, or a pharmaceutically acceptable salt thereof,
wherein $L^1$ is a group

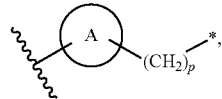

wherein:
A is aryl;
p is 0;
the wavy line indicates the point of attachment of $L^1$ to the rest of formula (I); and
* indicates the point of attachment of $L^1$ to $R^{10}$.

19. The compound of formula (I) according to claim 1, or a pharmaceutically acceptable salt thereof wherein:
X is $C-L^2-R^{11}$ or N;
$R^1$ is hydrogen;
$R^2$ is $C_{1-7}$-alkyl;
$R^3$ is $-(CH_2)_m-NR^{20}R^{21}$, wherein:
  $R^{20}$ is selected from hydrogen, $C_{1-7}$-alkyl and $C_{1-7}$-haloalkyl;
  $R^{21}$ is hydrogen; and
  m is 3 or 4;
$R^4$ is hydrogen;
$R^5$ is selected from $C_{1-7}$-alkyl, hydroxy-$C_{1-7}$-alkyl, $-(CH_2)_m-NR^{20}R^{21}$ and $-(CH_2)_n-C(O)-NR^{22}R^{23}$, wherein:
  $R^{20}$ is hydrogen or carboxy-$C_{1-7}$-alkyl;
  each of $R^{21}$, $R^{22}$ and $R^{23}$ is hydrogen;
  m is 2 or 3; and
  n is 2;
$R^6$ is hydrogen;
$R^7$ is selected from hydrogen, halogen, $C_{1-7}$-alkyl and $C_{1-7}$-alkoxy;
$R^8$ is selected from hydrogen and a carboxylic acid bioisostere;
$R^9$ is hydrogen;
$R^{10}$ is hydrogen or a carboxylic acid bioisostere;
$R^{11}$ is hydrogen;
$L^1$ is a covalent bond or a group

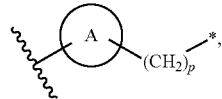

wherein:
A is aryl or heterocycloalkyl;
p is 0 or 1;
the wavy line indicates the point of attachment of $L^1$ to the rest of formula (I); and
* indicates the point of attachment of $L^1$ to $R^{10}$; and
$L^2$ is a covalent bond;
provided that at least one of $R^8$ and $R^{10}$ is a carboxylic acid bioisostere.

20. The compound of formula (I) according to claim 1, or a pharmaceutically acceptable salt thereof, wherein:
X is $C-L^2-R^{11}$;
$R^1$ is hydrogen;
$R^2$ is $C_{1-7}$-alkyl;
$R^3$ is $-(CH_2)_m-NR^{20}R^{21}$, wherein:
  $R^{20}$ and $R^{21}$ are both hydrogen; and
  m is 3 or 4;
$R^4$ is hydrogen;
$R^5$ is $-(CH_2)_m-NR^{20}R^{21}$, wherein:
  $R^{20}$ and $R^{21}$ are both hydrogen; and
  m is 2 or 3;
$R^6$ is hydrogen;
$R^7$ is selected from hydrogen, halogen, $C_{1-7}$-alkyl and $C_{1-7}$-alkoxy;
$R^8$ is hydrogen;
$R^9$ is hydrogen;
$R^{10}$ is a carboxylic acid bioisostere;
$R^{11}$ is hydrogen;
$L^1$ is a group

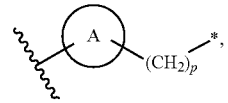

wherein:
A is aryl;
p is 0;
the wavy line indicates the point of attachment of $L^1$ to the rest of formula (I); and
* indicates the point of attachment of $L^1$ to $R^{10}$; and
$L^2$ is a covalent bond.

21. The compound of formula (I) according to claim 1, or a pharmaceutically acceptable salt thereof wherein:
X is $C-L^2-R^{11}$;
$R^1$ is hydrogen;
$R^2$ is methyl;
$R^3$ is $-(CH_2)_m-NR^{20}R^{21}$, wherein:
  $R^{20}$ and $R^{21}$ are both hydrogen; and
  m is 3 or 4;
$R^4$ is hydrogen;
$R^5$ is $-(CH_2)_m-NR^{20}R^{21}$, wherein:
  $R^{20}$ and $R^{21}$ are both hydrogen; and
  m is 2 or 3;
$R^6$ is hydrogen;
$R^7$ is selected from hydrogen, chloro, fluoro, methyl and methoxy;
$R^8$ is hydrogen;
$R^9$ is hydrogen;
$R^{10}$ is a carboxylic acid bioisostere selected from 1H-tetrazol-5-yl and $-S(O)_2-OH$;
$R^{11}$ is hydrogen;
$L^1$ is a group

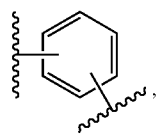

wherein the wavy lines indicate the points of attachment; and

L² is a covalent bond.

22. The compound of formula (I) according to claim 1, wherein the compound is selected from the group consisting of:

- 4-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(25),3,5,7,21,23-hexaen-22-yl]benzenesulfonic acid;
- (11S,14S,17S)-14-(4-aminobutyl)-11-(3-aminopropyl)-22-(3H-benzotriazol-5-yl)-25-chloro-17-(1H-indol-3-ylmethyl)-16-methyl-2-thia-4,10,13,16,19-pentazatricyclo[19.4.0.03,8]pentacosa-1(25),3,5,7,21,23-hexaene-12,15,18-trione;
- (11S,14S,17S)-14-(4-aminobutyl)-11-(3-aminopropyl)-25-chloro-17-(1H-indol-3-ylmethyl)-16-methyl-22-[4-(1H-tetrazol-5-yl)phenyl]-2-thia-4,10,13,16,19-pentazatricyclo[19.4.0.03,8]pentacosa-1(25),3,5,7,21,23-hexaene-12,15,18-trione;
- (11S,14S,17S)-14-(4-aminobutyl)-11-(3-aminopropyl)-25-chloro-17-(1H-indol-3-ylmethyl)-16-methyl-22-[3-(1H-tetrazol-5-yl)phenyl]-2-thia-4,10,13,16,19-pentazatricyclo[19.4.0.03,8]pentacosa-1(25),3,5,7,21,23-hexaene-12,15,18-trione;
- N-[4-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]phenyl]sulfonylacetamide;
- (11S,14S,17S)-14-(4-aminobutyl)-11-(3-aminopropyl)-25-chloro-17-(1H-indol-3-ylmethyl)-16-methyl-22-(2-oxo-1H-pyrimidin-5-yl)-2-thia-4,10,13,16,19-pentazatricyclo[19.4.0.03,8]pentacosa-1(25),3,5,7,21,23-hexaene-12,15,18-trione;
- (11S,14S,17S)-14-(4-aminobutyl)-11-(3-aminopropyl)-25-chloro-17-(1H-indol-3-ylmethyl)-16-methyl-22-[2-oxo-1-(1H-tetrazol-5-ylmethyl)-4-pyridyl]-2-thia-4,10,13,16,19-pentazatricyclo[19.4.0.03,8]pentacosa-1(25),3(8),4,6,21,23-hexaene-12,15,18-trione;
- (11S,14S,17S)-14-(4-aminobutyl)-11-(3-aminopropyl)-25-chloro-17-(1H-indol-3-ylmethyl)-16-methyl-22-[4-(5-oxo-4H-1,2,4-thiadiazol-3-yl)phenyl]-2-thia-4,10,13,16,19-pentazatricyclo[19.4.0.03,8]pentacosa-1(25),3(8),4,6,21,23-hexaene-12,15,18-trione;
- (11S,14S,17S)-14-(4-aminobutyl)-11-(3-aminopropyl)-25-chloro-17-(1H-indol-3-ylmethyl)-16-methyl-22-[4-(5-oxo-4H-1,2,4-oxadiazol-3-yl)phenyl]-2-thia-4,10,13,16,19-pentazatricyclo[19.4.0.03,8]pentacosa-1(25),3(8),4,6,21,23-hexaene-12,15,18-trione;
- (11S,14S,17S)-14-(4-aminobutyl)-11-(3-aminopropyl)-17-(1H-indol-3-ylmethyl)-16-methyl-22-[4-(1H-tetrazol-5-yl)phenyl]-2-thia-4,10,13,16,19-pentazatricyclo[19.4.0.03,8]pentacosa-1(25),3(8),4,6,21,23-hexaene-12,15,18-trione;
- 4-[(11S,14S,17S)-14-(4-aminobutyl)-11-(3-aminopropyl)-25-chloro-17-(1H-indol-3-ylmethyl)-16-methyl-12,15,18-trioxo-2-thia-4,7,10,13,16,19-hexazatricyclo[19.4.0.03,8]pentacosa-1(25),3(8),4,6,21,23-hexaen-22-yl]benzenesulfonic acid;
- 4-[(11S,14S,17S)-14-(4-aminobutyl)-11-(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzenesulfonic acid;
- (11S,14S,17S)-14-(4-aminobutyl)-11-(3-aminopropyl)-25-fluoro-17-(1H-indol-3-ylmethyl)-16-methyl-22-[4-(1H-tetrazol-5-yl)phenyl]-2-thia-4,10,13,16,19-pentazatricyclo[19.4.0.03,8]pentacosa-1(25),3(8),4,6,21,23-hexaene-12,15,18-trione;
- N-[4-[(11S,14S,17S)-14-(4-aminobutyl)-11-(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]phenyl]sulfonylacetamide;
- 4-[(11S,14S,17S)-14-(4-aminobutyl)-11-(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]-N-methylsulfonyl-benzamide;
- 4-[(11S,14S,17S)-11,14-bis(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]benzenesulfonic acid;
- (11S,14S,17S)-11,14-bis(3-aminopropyl)-25-chloro-17-(1H-indol-3-ylmethyl)-16-methyl-22-[4-(1H-tetrazol-5-yl)phenyl]-2-thia-4,10,13,16,19-pentazatricyclo[19.4.0.03,8]pentacosa-1(21),3,5,7,22,24-hexaene-12,15,18-trione;
- (11S,14S,17S)-11,14-bis(3-aminopropyl)-25-chloro-17-(1H-indol-3-ylmethyl)-16-methyl-22-(2-oxo-1H-pyrimidin-5-yl)-2-thia-4,10,13,16,19-pentazatricyclo[19.4.0.03,8]pentacosa-1(21),3,5,7,22,24-hexaene-12,15,18-trione;
- 4-[(11S,14S,17S)-11,14-bis(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzenesulfonic acid;
- (11S,14S,17S)-11,14-bis(3-aminopropyl)-25-fluoro-17-(1H-indol-3-ylmethyl)-16-methyl-22-[4-(1H-tetrazol-5-yl)phenyl]-2-thia-4,10,13,16,19-pentazatricyclo[19.4.0.03,8]pentacosa-1(25),3(8),4,6,21,23-hexaene-12,15,18-trione;
- [4-[(11S,14S,17S)-11,14-bis(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]phenyl]phosphonic acid;
- [4-[(11S,14S,17S)-14-(4-aminobutyl)-11-(3-amino-3-oxo-propyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]phenyl]phosphonic acid;
- [4-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]phenyl]phosphonic acid;
- 4-[(11S,14S,17S)-14-(4-aminobutyl)-11-(3-aminopropyl)-17-(1H-indol-3-ylmethyl)-16,25-dimethyl-12,15,18-trioxo-2-thia-4,10,13,16,19-pentazatricyclo[19.4.0.03,8]pentacosa-1(25),3(8),4,6,21,23-hexaen-22-yl]benzenesulfonic acid;

(11S,14S,17S)-14-(4-aminobutyl)-11-(3-aminopropyl)-17-(1H-indol-3-ylmethyl)-16,25-dimethyl-22-[4-(1H-tetrazol-5-yl)phenyl]-2-thia-4,10,13,16,19-pentazatricyclo[19.4.0.0³,⁸]pentacosa-1(25),3(8),4,6,21,23-hexaene-12,15,18-trione;

4-[(11S,14S,17S)-14-(4-aminobutyl)-11-(2-aminoethyl)-25-chloro-17-(1H-indol-3-ylmethyl)-16-methyl-12,15,18-trioxo-2-thia-4,10,13,16,19-pentazatricyclo[19.4.0.0³,⁸]pentacosa-1(25),3(8),4,6,21,23-hexaen-22-yl]benzenesulfonic acid;

4-[(11S,14S,17S)-11-(2-aminoethyl)-14-(3-aminopropyl)-25-chloro-17-(1H-indol-3-ylmethyl)-16-methyl-12,15,18-trioxo-2-thia-4,10,13,16,19-pentazatricyclo[19.4.0.0³,⁸]pentacosa-1(25),3(8),4,6,21,23-hexaen-22-yl]benzenesulfonic acid;

4-[(11S,14S,17S)-14-(3-aminopropyl)-25-chloro-17-(1H-indol-3-ylmethyl)-11,16-dimethyl-12,15,18-trioxo-2-thia-4,10,13,16,19-pentazatricyclo[19.4.0.0³,⁸]pentacosa-1(25),3(8),4,6,21,23-hexaen-22-yl]benzenesulfonic acid;

4-[(11S,14S,17S)-14-(4-aminobutyl)-11-(3-aminopropyl)-17-(1H-indol-3-ylmethyl)-25-methoxy-16-methyl-12,15,18-trioxo-2-thia-4,10,13,16,19-pentazatricyclo[19.4.0.0³,⁸]pentacosa-1(25),3(8),4,6,21,23-hexaen-22-yl]benzenesulfonic acid;

(11S,14S,17S)-14-(4-aminobutyl)-11-(3-aminopropyl)-17-(1H-indol-3-ylmethyl)-25-methoxy-16-methyl-22-[4-(1H-tetrazol-5-yl)phenyl]-2-thia-4,10,13,16,19-pentazatricyclo[19.4.0.0³,⁸]pentacosa-1(25),3(8),4,6,21,23-hexaene-12,15,18-trione;

N-[4-[(11S,14S,17S)-14-(4-aminobutyl)-25-chloro-11-(3-hydroxypropyl)-17-(1H-indol-3-ylmethyl)-16-methyl-12,15,18-trioxo-2-thia-4,10,13,16,19-pentazatricyclo[19.4.0.0³,⁸]pentacosa-1(21),3,5,7,22,24-hexaen-22-yl]phenyl]sulfonylacetamide;

(11S,14S,17S)-14-(4-aminobutyl)-25-chloro-11-(3-hydroxypropyl)-22-(2-hydroxypyrimidin-5-yl)-17-(1H-indol-3-ylmethyl)-16-methyl-2-thia-4,10,13,16,19-pentazatricyclo[19.4.0.0³,⁸]pentacosa-1(21),3,5,7,22,24-hexaene-12,15,18-trione;

N-[4-[(11S,14S,17S)-25-chloro-14-[4-(2,2-difluoroethylamino)butyl]-11-(3-hydroxypropyl)-17-(1H-indol-3-ylmethyl)-16-methyl-12,15,18-trioxo-2-thia-4,10,13,16,19-pentazatricyclo[19.4.0.0³,⁸]pentacosa-1(21),3,5,7,22,24-hexaen-22-yl]phenyl]sulfonylacetamide;

N-[4-[(11S,14S,17S)-25-chloro-11-(3-hydroxypropyl)-17-(1H-indol-3-ylmethyl)-16-methyl-14-[4-(methylamino)butyl]-12,15,18-trioxo-2-thia-4,10,13,16,19-pentazatricyclo[19.4.0.0³,⁸]pentacosa-1(21),3,5,7,22,24-hexaen-22-yl]phenyl]sulfonylacetamide;

(11S,14S,17S)-11-(3-aminopropyl)-25-chloro-14-[4-(2,2-difluoroethylamino)butyl]-22-(2-hydroxypyrimidin-5-yl)-17-(1H-indol-3-ylmethyl)-16-methyl-2-thia-4,10,13,16,19-pentazatricyclo[19.4.0.0³,⁸]pentacosa-1(21),3,5,7,22,24-hexaene-12,15,18-trione;

3-[3-[(11S,14S,17S)-22-[4-(acetylsulfamoyl)phenyl]-14-(4-aminobutyl)-25-chloro-17-(1H-indol-3-ylmethyl)-16-methyl-12,15,18-trioxo-2-thia-4,10,13,16,19-pentazatricyclo[19.4.0.0³,⁸]pentacosa-1(21),3,5,7,22,24-hexaen-11-yl]propylamino]propanoic acid;

(11S,14S,17S)-14-(4-aminobutyl)-11-(3-aminopropyl)-25-chloro-17-(1H-indol-3-ylmethyl)-16-methyl-23-(1H-tetrazol-5-yl)-2-thia-4,10,13,16,19-pentazatricyclo[19.4.0.0³,⁸]pentacosa-1(21),3,5,7,22,24-hexaene-12,15,18-trione; and (11S,14S,17S)-14-(4-aminobutyl)-11-(3-aminopropyl)-25-chloro-17-(1H-indol-3-ylmethyl)-16-methyl-23-(1H-triazol-5-yl)-2-thia-4,10,13,16,19-pentazatricyclo[19.4.0.0³,⁸]pentacosa-1(21),3,5,7,22,24-hexaene-12,15,18-trione;

or a pharmaceutically acceptable salt thereof.

23. The compound of formula (I) according to claim 1, wherein the compound is selected from the group consisting of:

(11S,14S,17S)-14-(4-aminobutyl)-11-(3-aminopropyl)-25-chloro-17-(1H-indol-3-ylmethyl)-16-methyl-22-[4-(1H-tetrazol-5-yl)phenyl]-2-thia-4,10,13,16,19-pentazatricyclo[19.4.0.0³,⁸]pentacosa-1(25),3,5,7,21,23-hexaene-12,15,18-trione (11S,14S,17S)-14-(4-aminobutyl)-11-(3-aminopropyl)-17-(1H-indol-3-ylmethyl)-16-methyl-22-[4-(1H-tetrazol-5-yl)phenyl]-2-thia-4,10,13,16,19-pentazatricyclo[19.4.0.0³,⁸]pentacosa-1(25),3(8),4,6,21,23-hexaene-12,15,18-trione 4-[(11S,14S,17S)-14-(4-aminobutyl)-11-(3-aminopropyl)-25-fluoro-17-(1H-indol-3-ylmethyl)-16-methyl-12,15,18-trioxo-2-thia-4,10,13,16,19-pentazatricyclo[19.4.0.0³,⁸]pentacosa-1(25),3(8),4,6,21,23-hexaen-22-yl]benzenesulfonic acid;

4-[(11S,14S,17S)-11,14-bis(3-aminopropyl)-25-chloro-17-(1H-indol-3-ylmethyl)-16-methyl-12,15,18-trioxo-2-thia-4,10,13,16,19-pentazatricyclo[19.4.0.0³,⁸]pentacosa-1(21),3,5,7,22,24-hexaen-22-yl]benzenesulfonic acid;

4-[(11S,14S,17S)-14-(4-aminobutyl)-11-(3-aminopropyl)-17-(1H-indol-3-ylmethyl)-16,25-dimethyl-12,15,18-trioxo-2-thia-4,10,13,16,19-pentazatricyclo[19.4.0.0³,⁸]pentacosa-1(25),3(8),4,6,21,23-hexaen-22-yl]benzenesulfonic acid;

4-[(11S,14S,17S)-14-(4-aminobutyl)-11-(2-aminoethyl)-25-chloro-17-(1H-indol-3-ylmethyl)-16-methyl-12,15,18-trioxo-2-thia-4,10,13,16,19-pentazatricyclo[19.4.0.0³,⁸]pentacosa-1(25),3(8),4,6,21,23-hexaen-22-yl]benzenesulfonic acid;

4-[(11S,14S,17S)-11-(2-aminoethyl)-14-(3-aminopropyl)-25-chloro-17-(1H-indol-3-ylmethyl)-16-methyl-12,15,18-trioxo-2-thia-4,10,13,16,19-pentazatricyclo[19.4.0.0³,⁸]pentacosa-1(25),3(8),4,6,21,23-hexaen-22-yl]benzenesulfonic acid; and 4-[(11S,14S,17S)-14-(4-aminobutyl)-11-(3-aminopropyl)-17-(1H-indol-3-ylmethyl)-25-methoxy-16-methyl-12,15,18-trioxo-2-thia-4,10,13,16,19-pentazatricyclo[19.4.0.0³,⁸]pentacosa-1(25),3(8),4,6,21,23-hexaen-22-yl]benzenesulfonic acid;

or a pharmaceutically acceptable salt thereof.

24. A pharmaceutical composition comprising a compound according to claim 1, or a pharmaceutically acceptable salt thereof, and one or more pharmaceutically acceptable excipients.

25. A process for the manufacture of a compound according to claim 1, or a pharmaceutically acceptable salt thereof, the process comprising the steps of:

a) reductive amination of a compound of formula (III), wherein X, $L^1$, $R^1$, $R^7$, $R^8$, $R^{10}$ and PG are as defined herein, with a compound of formula (IV), wherein $R^2$, $R^3$, $R^4$, $R^5$, $R^6$, $R^9$ and resin are as defined herein, to provide a compound of formula (II), wherein X, $L^1$, $R^1$, $R^2$, $R^3$, $R^4$, $R^5$, $R^6$, $R^7$, $R^8$, $R^9$, $R^{10}$, PG and resin are as defined herein;

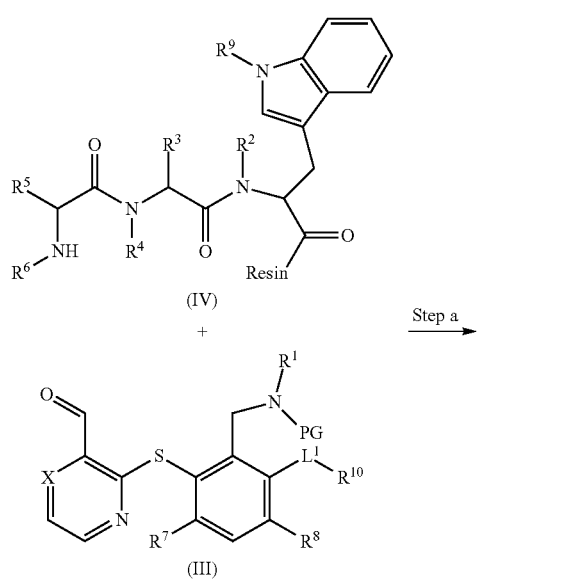

(IV)

+

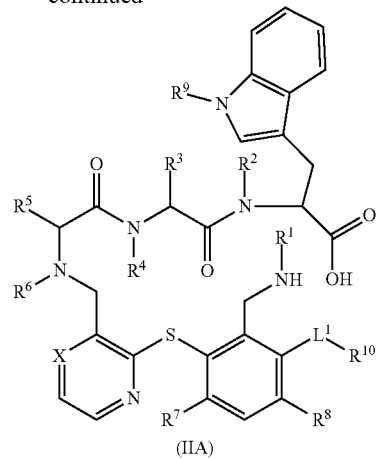

(III)

Step a b) removal of the protective group (PG) and the resin from the compound of formula (II) to provide a compound of formula (IIA), wherein X, $L^1$, $R^1$, $R^2$, $R^3$, $R^4$, $R^5$, $R^6$, $R^7$, $R^8$, $R^9$ and $R^{10}$ are as defined herein; and

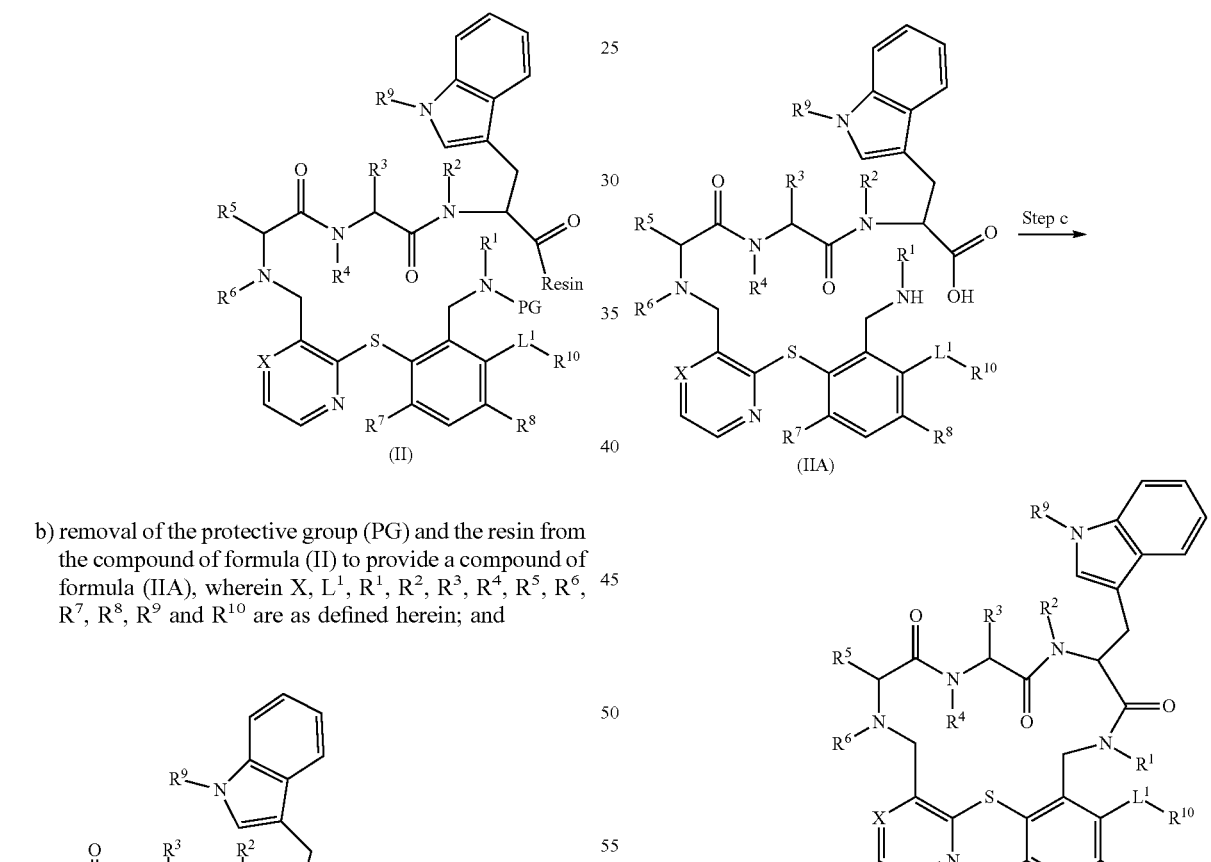

c) cyclisation of the compound of formula (IIA) using a coupling reagent in the presence of a base to afford said compound of formula (I).

26. A method for the treatment or prevention of infections and resulting diseases caused by *Acinetobacter baumannii*, the method comprising administering a compound according to claim 1, or a pharmaceutically acceptable salt thereof, or a pharmaceutical composition according to claim 24 to a human being or an animal in need thereof.

* * * * *